US011065280B2

(12) United States Patent
Font-Burgada et al.

(10) Patent No.: US 11,065,280 B2
(45) Date of Patent: Jul. 20, 2021

(54) HEPATOCYTES WITH HIGH REGENERATIVE CAPACITY FOR LIVER REPAIR

(71) Applicant: THE REGENTS OF THE UNIVERSITY OF CALIFORNIA, Oakland, CA (US)

(72) Inventors: Joan Font-Burgada, San Diego, CA (US); Michael Karin, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 564 days.

(21) Appl. No.: 15/571,680

(22) PCT Filed: May 3, 2016

(86) PCT No.: PCT/US2016/030520
§ 371 (c)(1),
(2) Date: Nov. 3, 2017

(87) PCT Pub. No.: WO2016/179148
PCT Pub. Date: Nov. 10, 2016

(65) Prior Publication Data
US 2018/0369291 A1    Dec. 27, 2018

Related U.S. Application Data

(60) Provisional application No. 62/156,592, filed on May 4, 2015.

(51) Int. Cl.
| | |
|---|---|
| *G01N 33/567* | (2006.01) |
| *C12N 5/071* | (2010.01) |
| *C07K 16/28* | (2006.01) |
| *A61K 35/407* | (2015.01) |
| *C07K 16/30* | (2006.01) |

(52) U.S. Cl.
CPC .......... *A61K 35/407* (2013.01); *C07K 16/28* (2013.01); *C07K 16/303* (2013.01); *C12N 5/067* (2013.01); *G01N 33/567* (2013.01); *G01N 2800/08* (2013.01)

(58) Field of Classification Search
None
See application file for complete search history.

(56) References Cited

U.S. PATENT DOCUMENTS

| | | | |
|---|---|---|---|
| 6,004,810 A | 12/1999 | Tateno et al. ................ | 435/353 |
| 10,683,484 B2 * | 6/2020 | Hu ....................... | C12N 5/0672 |
| 2015/0175962 A1 * | 6/2015 | Zhu ....................... | A61K 31/19 |
| | | | 424/85.2 |

OTHER PUBLICATIONS

Dorrell et al, "Prospective isolation of a bipotential clonogenic liver progenitor cell in adult mice" Genes and Development, 2011, vol. 25, pp. 1193-1203. (Year: 2011).*
Akhurst, et al., "A Modified Choline-Deficient, Ethionine-Supplemented Diet Protocol Effectively Induces Oval Cells in Mouse Liver." *Hepatology*, 34(3):519-522 (2001).
Alison, et al., "Stem Cells in Liver Regeneration, Fibrosis and Cancer: The Good, the Bad and the Ugly." *The Journal of Pathology*, 217(2):282-298 (2009).
Basu, et al., "Purification of Specific Cell Population by Fluorescence Activated Cell Sorting (Facs)." *J Vis Exp*(41) (2010).
Benhamouche, et al., "Apc Tumor Suppressor Gene Is the "Zonation-Keeper" of Mouse Liver." *Developmental Cell*, 10(6):759-770 (2006).
Bissig, et al., "Repopulation of Adult and Neonatal Mice with Human Hepatocytes: A Chimeric Animal Model." *Proceedings of the National Academy of Sciences of the United States of America*, 104(51):20507-20511 (2007).
Blanpain and Fuchs "Stem Cell Plasticity. Plasticity of Epithelial Stem Cells in Tissue Regeneration." *Science (New York, N.Y.)*, 344(6189):1242281 (2014).
Boulter, et al., "Differentiation of Progenitors in the Liver: A Matter of Local Choice." *The Journal of Clinical Investigation*, 123(5):1867-1873 (2013).
Carpentier, et al., "Embryonic Ductal Plate Cells Give Rise to Cholangiocytes, Periportal Hepatocytes, and Adult Liver Progenitor Cells." *Gastroenterology*, 141(4):1432-1438, 1438 e1431-1434 (2011).
Cheung and Rando "Molecular Regulation of Stem Cell Quiescence." *Nature Reviews. Molecular Cell Biology*, 14(6):329-340 (2013).
Chung, et al., "Structural and Molecular Interrogation of Intact Biological Systems." *Nature*, 497(7449):332-337 (2013a).
Chung and Deisseroth, Clarity for mapping the nervous system. *Nat Methods* 10, 508-513, (2013b).
Clevers "The Intestinal Crypt, a Prototype Stem Cell Compartment." *Cell*, 154(2):274-284 (2013).
Dobin, et al., "STAR: Ultrafast Universal RNA-Seq Aligner." *Bioinformatics*, 29(1):15-21 (2013).
Duncan, et al., "Stem Cells and Liver Regeneration." *Gastroenterology*, 137(2):466-481 (2009).
Español-Suñer, et al., "Liver Progenitor Cells Yield Functional Hepatocytes in Response to Chronic Liver Injury in Mice." *Gastroenterology*, 143(6):1564-1575 (2012a).
Español-Suñer, et al., "Liver Progenitor Cells Yield Functional Hepatocytes in Response to Chronic Liver Injury in Mice." *Gastroenterology*, 143(6):1564, 1575.e1-1575.e7 (2012b).
Farber "Similarities in the Sequence of Early Histological Changes Induced in the Liver of the Rat by Ethionine, 2-Acetylamino-Fluorene, and 3'-Methyl-4-Dimethylaminoazobenzene." *Cancer Research*, 16(2):142-148 (1956).

(Continued)

*Primary Examiner* — Allison M Fox
(74) *Attorney, Agent, or Firm* — Medlen & Carroll, LLP

(57) ABSTRACT

The invention provides purified mammalian hybrid hepatocyte (HybHP) cells, compositions comprising HybHP cells, methods for purifying HybHP cells, methods for in vitro culture of HybHP cells, and methods for using HybHP cells to repopulate and/or treat the liver of a subject in need thereof.

2 Claims, 27 Drawing Sheets
(23 of 27 Drawing Sheet(s) Filed in Color)

(56) References Cited

OTHER PUBLICATIONS

Fausto, et al., "Liver Regeneration." *Hepatology (Baltimore, Md.)*, 43(2 Suppl 1):53 (2006).
Fellous, et al., "Locating the Stem Cell Niche and Tracing Hepatocyte Lineages in Human Liver." *Hepatology (Baltimore, Md.)*, 49(5):1655-1663 (2009).
Fleming and Wanless "Glutamine Synthetase Expression in Activated Hepatocyte Progenitor Cells and Loss of Hepatocellular Expression in Congestion and Cirrhosis." *Liver international : official journal of the International Association for the Study of the Liver*, 33(4):525-534 (2013).
Fujii, et al., "A Murine Model for Non-Alcoholic Steatohepatitis Showing Evidence of Association between Diabetes and Hepatocellular Carcinoma." *Medical Molecular Morphology*, 46(3):141-152 (2013).
Furuyama, et al., "Continuous Cell Supply from a Sox9-Expressing Progenitor Zone in Adult Liver, Exocrine Pancreas and Intestine." *Nat Genet*, 43(1):34-41 (2010).
Gong, et al., "A Gene Expression Atlas of the Central Nervous System Based on Bacterial Artificial Chromosomes." *Nature*, 425(6961):917-925 (2003).
Grompe, et al., "Loss of Fumarylacetoacetate Hydrolase Is Responsible for the Neonatal Hepatic Dysfunction Phenotype of Lethal Albino Mice." *Genes Dev*, 7(12A):2298-2307 (1993).
Grompe, et al., "Pharmacological Correction of Neonatal Lethal Hepatic Dysfunction in a Murine Model of Hereditary Tyrosinaemia Type I." *Nature Genetics*, 10(4):453-460 (1995).
Grompe "Liver Stem Cells, Where Art Thou?" *Cell Stem Cell*, 15(3):257-258 (2014).
He, et al., "Identification of Liver Cancer Progenitors Whose Malignant Progression Depends on Autocrine IL-6 Signaling." *Cell*, 155(2):384-396 (2013).
Heinz, et al., "Simple Combinations of Lineage-Determining Transcription Factors Prime cis-Regulatory Elements Required for Macrophage and B Cell Identities." *Mol Cell*, 38(4):576-589 (2010).
Huang da, et al., "Bioinformatics Enrichment Tools: Paths toward the Comprehensive Functional Analysis of Large Gene Lists." *Nucleic Acids Res*, 37(1):1-13 (2009a).
Huang da, et al., "Systematic and Integrative Analysis of Large Gene Lists Using David Bioinformatics Resources." *Nature Protocols*, 4(1):44-57 (2009b).
Huch, et al., "In Vitro Expansion of Single Lgr5+ Liver Stem Cells Induced by Wnt-Driven Regeneration." *Nature*, 494(7436):247-250 (2013).
Huch, et al., "Long-Term Culture of Genome-Stable Bipotent Stem Cells from Adult Human Liver." *Cell*, 160(1-2):299-312 (2015).
Hui, et al., "p38alpha Suppresses Normal and Cancer Cell Proliferation by Antagonizing the Jnk-C-Jun Pathway." *Nat Genet*, 39(6):741-749 (2007).
Inokuchi, et al., "Disruption of Tak1 in Hepatocytes Causes Hepatic Injury, Inflammation, Fibrosis, and Carcinogenesis." *Proceedings of the National Academy of Sciences of the United States of America*, 107(2):844-849 (2010).
Isse, et al., "Preexisting Epithelial Diversity in Normal Human Livers: A Tissue-Tethered Cytometric Analysis in Portal/Periportal Epithelial Cells." *Hepatology*, 57(4):1632-1643 (2013).
Itoh and Miyajima "Liver Regeneration by Stem/Progenitor Cells." *Hepatology (Baltimore, Md.)*, 59(4):1617-1626 (2014).
Jungermann and Katz "Functional Specialization of Different Hepatocyte Populations." *Physiological Reviews*, 69(3):69(3):708-764 (pp. 708-742) (1989a).
Jungermann and Katz "Functional Specialization of Different Hepatocyte Populations." *Physiological Reviews*, 69(3): 69(3):708-764 (pp. 708, 743-764) (1989b).
Kaneko, et al., "Adaptive Remodeling of the Biliary Architecture Underlies Liver Homeostasis." *Hepatology* (2015).
Kang, et al., "Role of CYP2E1 in Diethylnitrosamine-Induced Hepatocarcinogensis in Vivo." *Cancer Research*, 67(23):11141-11146 (2007).
Karin "Nuclear Factor-KappaB in Cancer Development and Progression." *Nature*, 441(7092):431-436 (2006).
Kisseleva, et al., "Recent Advances in Liver Stem Cell Therapy." *Current Opinion In Gastroenterology*, 26(4):395-402 (2010).
Kopp, et al., "Sox9+ Ductal Cells Are Multipotent Progenitors Throughout Development but Do Not Produce New Endocrine Cells in the Normal or Injured Adult Pancreas." *Development (Cambridge, England)*, 138(4):653-665 (2011).
Kuraishy, et al., "Tumor Promotion Via Injury- and Death-Induced Inflammation." *Immunity*, 35(4):467-477 (2011).
Kuwahara, et al., "The Hepatic Stem Cell Niche: Identification by Label-Retaining Cell Assay." *Hepatology*, 47(6):1994-2002 (2008).
Lavin, et al., "Tissue-Resident Macrophage Enhancer Landscapes Are Shaped by the Local Microenvironment." *Cell*, 159(6):1312-1326 (2014).
Luedde, et al., "Deletion of Nemo/Ikkgamma in Liver Parenchymal Cells Causes Steatohepatitis and Hepatocellular Carcinoma." *Cancer Cell*, 11(2):119-132 (2007).
Maeda, et al., "IKKbeta Couples Hepatocyte Death to Cytokine-Driven Compensatory Proliferation That Promotes Chemical Hepatocarcinogenesis." *Cell*, 121(7):977-990 (2005).
Malato, et al., "Fate Tracing of Mature Hepatocytes in Mouse Liver Homeostasis and Regeneration." *J Clin Invest*, 121(12):4850-4860 (2011).
Means, et al., "A Ck19(Creert) Knockin Mouse Line Allows for Conditional DNA Recombination in Epithelial Cells in Multiple Endodermal Organs." *Genesis*, 46(6):318-323 (2008).
Michalopoulos, et al., "Transdifferentiation of Rat Hepatocytes into Biliary Cells after Bile Duct Ligation and Toxic Biliary Injury." *Hepatology (Baltimore, Md.)*, 41(3):535-544 (2005).
Michalopoulos "Liver Regeneration." *Journal of Cellular Physiology*, 213(2):286-300 (2007).
Miyajima, et al., "Stem/Progenitor Cells in Liver Development, Homeostasis, Regeneration, and Reprogramming. " *Cell Stem Cell*, 14(5):561-574 (2014).
Nakagawa, et al., "Loss of Liver E-Cadherin Induces Sclerosing Cholangitis and Promotes Carcinogenesis." *Proceedings of the National Academy of Sciences of the United States of America*, 111(3):1090-1095 (2014a).
Nakagawa, et al., "ER Stress Cooperates with Hypernutrition to Trigger TNF-Dependent Spontaneous HCC Development." *Cancer Cell*, 26(3):331-343 (2014b).
Ponder, et al., "Mouse Hepatocytes Migrate to Liver Parenchyma and Function Indefinitely after Intrasplenic Transplantation." *Proceedings of the National Academy of Sciences of the United States of America*, 88(4):1217-1221 (1991).
Preisegger, et al., "Atypical Ductular Proliferation and Its Inhibition by Transforming Growth Factor Beta1 in the 3,5-Diethoxycarbonyl-1,4-Dihydrocollidine Mouse Model for Chronic Alcoholic Liver Disease." *Laboratory Investigation; A Journal of Technical Methods and Pathology*, 79(2):103-109 (1999).
Richardson, et al., "Progressive Fibrosis in Nonalcoholic Steatohepatitis: Association with Altered Regeneration and a Ductular Reaction." *Gastroenterology*, 133(1):80-90 (2007).
Robinson, et al., "Edger: A Bioconductor Package for Differential Expression Analysis of Digital Gene Expression Data." *Bioinformatics*, 26(1):139-140 (2010).
Rodrigo-Torres, et al., "The Biliary Epithelium Gives Rise to Liver Progenitor Cells." *Hepatology* 60:1367-1377 (2014).
Roskams "Liver Stem Cells and Their Implication in Hepatocellular and Cholangiocarcinoma." *Oncogene*, 25(27):3818-3822 (2006).
Rossell, "Gaga: A Parsimonious and Flexible Model for Differential Expression Analysis." *Ann Appl Stat*, 3(3):1035-1051 (2009).
Rossell, et al., "Quantifying Alternative Splicing from Paired-End Rna-Sequencing Data." *Ann Appl Stat*, 8(1):309-330 (2014).
Sakurai, et al., "Hepatocyte Necrosis Induced by Oxidative Stress and Il-1 Alpha Release Mediate Carcinogen-Induced Compensatory Proliferation and Liver Tumorigenesis." *Cancer Cell*, 14(2):156-165 (2008).
Schaub, et al., "Evidence against a Stem Cell Origin of New Hepatocytes in a Common Mouse Model of Chronic Liver Injury." *Cell Reports*, 8(4):933-939 (2014).

(56) References Cited

OTHER PUBLICATIONS

Schmelzer, et al., "Human Hepatic Stem Cells from Fetal and Postnatal Donors." *J Exp Med*, 204(8):1973-1987 (2007).
Schuler, et al., "Efficient Temporally Controlled Targeted Somatic Mutagenesis in Hepatocytes of the Mouse." *Genesis*, 39(3):167-172 (2004).
Sekiya and Suzuki, "Direct Conversion of Mouse Fibroblasts to Hepatocyte-Like Cells by Defined Factors." *Nature*, 475(7356):390-393 (2011).
Sekiya and Suzuki, "Hepatocytes, Rather Than Cholangiocytes, Can Be the Major Source of Primitive Ductules in the Chronically Injured Mouse Liver." *The American Journal Of Pathology*, 184(5):1468-1478 (2014).
Sell and Leffert, "Liver Cancer Stem Cells." *Journal Of Clinical Oncology : Official Journal Of The American Society of Clinical Oncology*, 26(17):2800-2805 (2008).
Si-Tayeb, et al., "Highly Efficient Generation of Human Hepatocyte-Like Cells from Induced Pluripotent Stem Cells." *Hepatology (Baltimore, Md.)*, 51(1):297-305 (2009).
Slack, "Metaplasia and Transdifferentiation: From Pure Biology to the Clinic." *Nature reviews. Molecular Cell Biology*, 8(5):369-378 (2007).
Tanimizu, et al., "Sry Hmg Box Protein 9-Positive (Sox9+) Epithelial Cell Adhesion Molecule-Negative (Epcam-) Biphenotypic Cells Derived from Hepatocytes Are Involved in Mouse Liver Regeneration." *The Journal Of Biological Chemistry*, 289(11):7589-7598 (2014).
Tannour-Louet, et al., "A Tamoxifen-Inducible Chimeric CRE Recombinase Specifically Effective in the Fetal and Adult Mouse Liver." *Hepatology (Baltimore, Md.)*, 35(5):1072-1081 (2002).
Tarlow, et al., "Clonal Tracing of Sox9+ Liver Progenitors in Mouse Oval Cell Injury." *Hepatology*, 60(1):278-289 (2014a).
Tarlow, et al., "Bipotential Adult Liver Progenitors Are Derived from Chronically Injured Mature Hepatocytes." *Cell Stem Cell*, 15(5):605-618 (2014b).
Tomasetti and Vogelstein, "Cancer Etiology. Variation in Cancer Risk among Tissues Can Be Explained by the Number of Stem Cell Divisions." *Science*, 347(6217):78-81 (2015).
Wang, et al., "The Origin and Liver Repopulating Capacity of Murine Oval Cells." *Proceedings of the National Academy of Sciences of the United States of America*, 100 Suppl 1:11881-11888 (2003).
Weglarz, et al., "Hepatocyte Transplantation into Diseased Mouse Liver. Kinetics of Parenchymal Repopulation and Identification of the Proliferative Capacity of Tetraploid and Octaploid Hepatocytes." *The American Journal of Pathology*, 157(6):1963-1974 (2000).
Wong, et al., "Resistance to Carbon Tetrachloride-Induced Hepatotoxicity in Mice Which Lack Cyp2e1 Expression." *Toxicology And Applied Pharmacology*, 153(1):109-118 (1998).
Yamamoto, et al., "A Multifunctional Reporter Mouse Line for CRE- and FLP-Dependent Lineage Analysis." *Genesis (New York, N.Y. : 2000)*, 47(2):107-114 (2009).
Yanger, et al., "Robust Cellular Reprogramming Occurs Spontaneously During Liver Regeneration." *Genes & Development*, 27(7):719-724 (2013).
Yanger, et al., "Adult Hepatocytes Are Generated by Self-Duplication Rather Than Stem Cell Differentiation." *Cell Stem Cell*, 15(3):340-349 (2014).
Yu, et al., "Reprogramming Fibroblasts into Bipotential Hepatic Stem Cells by Defined Factors." *Cell Stem Cell*, 13(3):328-340 (2013).
Zhou and Melton, "Extreme Makeover: Converting One Cell into Another." *Cell Stem Cell*, 3(4):382-388 (2008).
Zhu, et al., "Mouse Liver Repopulation with Hepatocytes Generated from Human Fibroblasts." *Nature*, 508(7494):93-97 (2014).
Tee, et al., "Dual phenotypic expression of hepatocytes and bile ductular markers in developing and preneoplastic rat liver." *Carcinogenesis*, 17(2)251-259 (1996).

\* cited by examiner

Fig. 2A
Fig. 2B
Fig. 2C
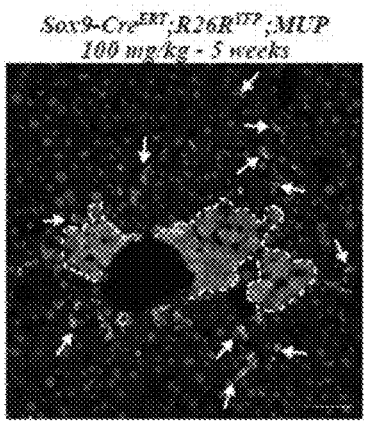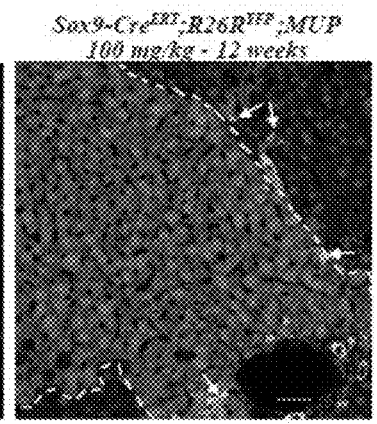
Fig. 2D
Fig. 2E
Fig. 2F
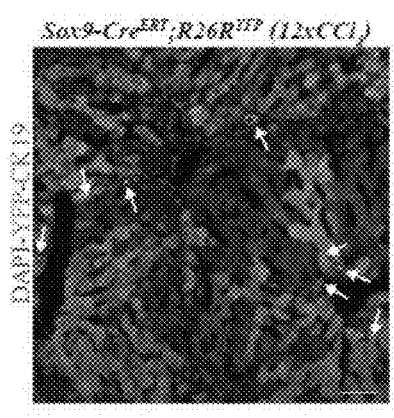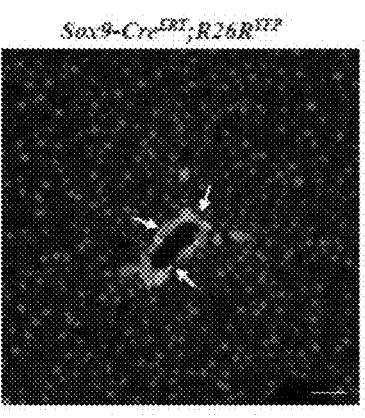

Fig. 3A
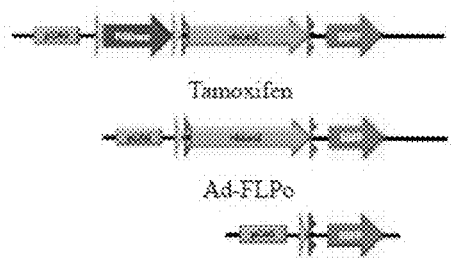
Fig. 3G
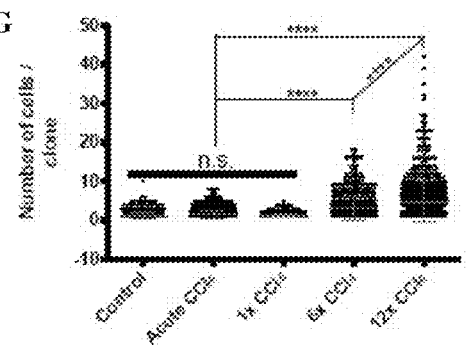
Fig. 3B  Fig. 3C  Fig. 3D  Fig. 3E
 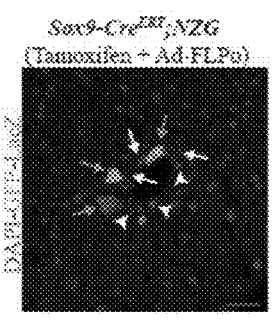 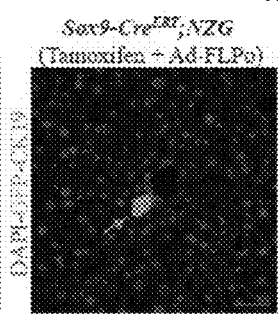 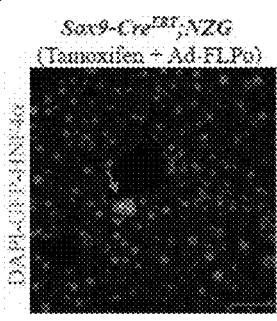
Fig. 3F
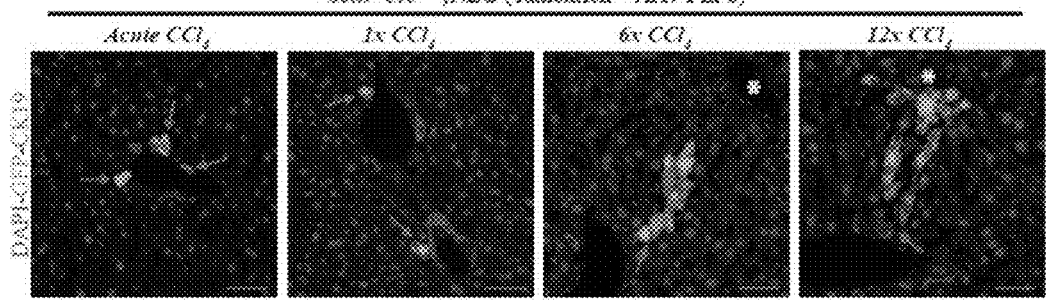

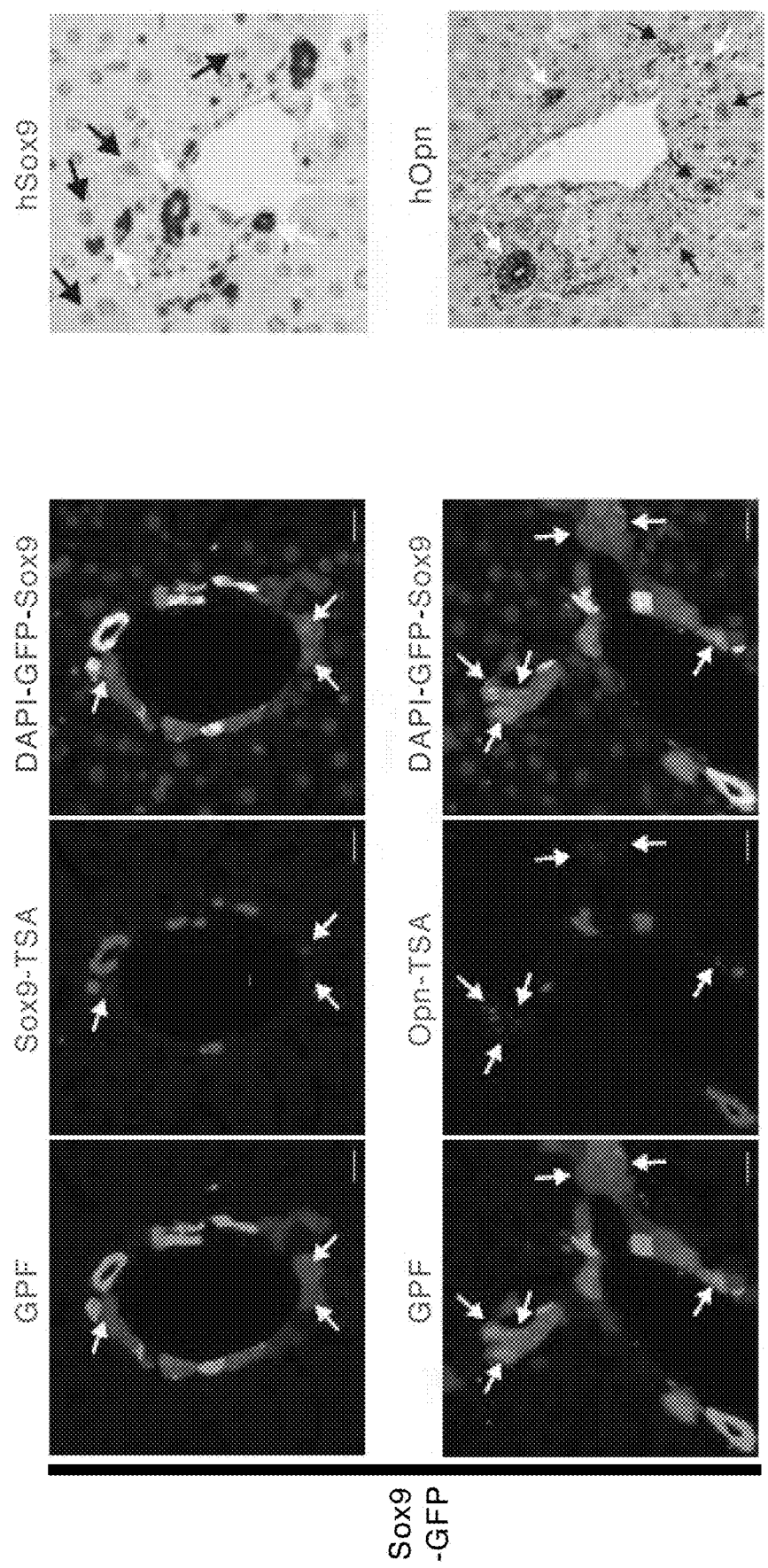

Fig. 13A
Fig. 13B
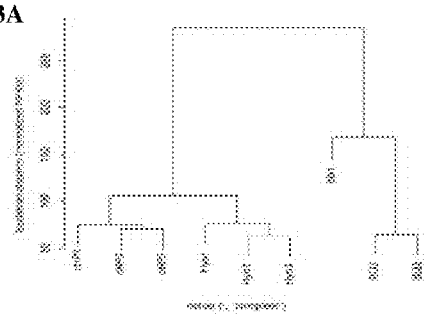
Fig. 13C
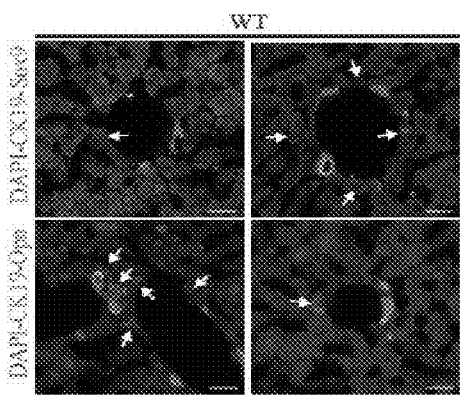
Fig. 13D
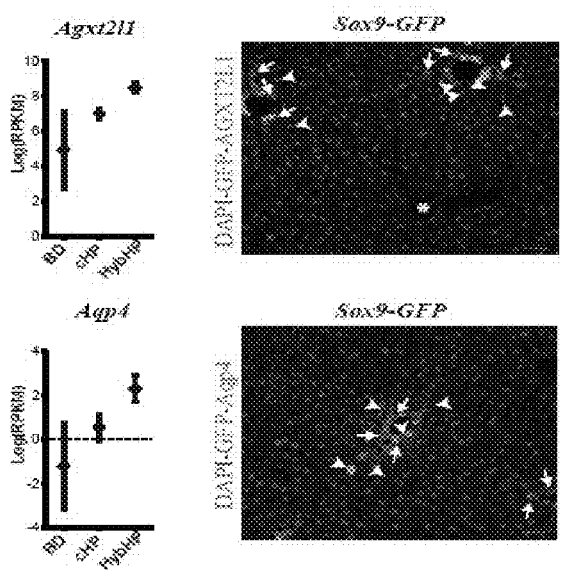
Fig. 13E
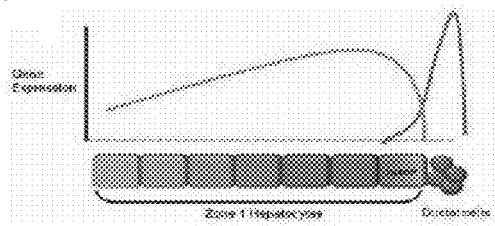

HEPATOCYTES WITH HIGH REGENERATIVE CAPACITY FOR LIVER REPAIR

This application is the U.S. national stage filing under 35 U.S.C § 371 of, and claims priority to, co-pending PCT Application No PCT/US16/30520, filed on May 3, 2016, which claims priority to U.S. provisional Application Ser. No. 62/156,592, filed on May 4, 2015, each of which is herein incorporated by reference.

GOVERNMENT INTEREST

This invention was made with government support under Grant Numbers CA118165, CA155120, and ES010337 awarded by The National Institutes of Health (NIH). The government has certain rights in the invention.

BACKGROUND OF THE INVENTION

Liver damage, and in particular, chronic liver disease, remains the leading cause of liver transplantation, a highly expensive medical procedure and a prominent cause of morbidity and mortality. Cell transplantation has been proposed as an alternative to liver transplantation but the ideal donor cell type remains to be determined. Liver stem cells, cultured ductal cells and their derivatives were suggested (Huch et al., 2013; Huch et al., 2015; Miyajima et al., 2014). Fetal liver progenitor cells also hold promise for transplantation therapy, but concerns were raised about their safety and methods of isolation (Kisseleva et al., 2010). There have been several reports of conversion of induced Pluripotent Stem Cells (iPSC) into hepatocytes, but the repopulation potential of such cells and functional recovery are inferior to those of conventional hepatocytes (Sekiya and Suzuki, 2011; Si-Tayeb et al., 2009; Yu et al., 2013; Zhu et al., 2014). Furthermore, iPSCs are tumorigenic and the tumorigenic potential of iPSC-generated hepatocytes has not been conclusively ruled out.

Adult mammalian tissues rely on diverse mechanisms to maintain homeostasis. Dedicated stem cell compartments that sustain normal turnover exist in highly proliferative tissues, such as the skin and intestine (Blanpain and Fuchs, 2014; Clevers, 2013). In tissues considered quiescent, such as the liver, pancreas or kidney, the presence of stem cells and specialized niches has been long debated and remains controversial. Furthermore, during toxic and physical injuries to which these tissues are highly susceptible, regenerative strategies and restorative mechanisms vary extensively and may involve dormant stem cells, transdifferentiation, metaplasia, or simple proliferation of mature cells (Cheung and Rando, 2013; Slack, 2007; Zhou and Melton, 2008). Even though liver parenchymal cells turnover very slowly, the liver displays high capacity for regeneration upon acute or chronic damage, capable of restoring 70% tissue loss within a few weeks without compromising overall viability (Fausto et al., 2006; Michalopoulos, 2007). Given its many vital functions, especially the detoxification of harmful chemical compounds and toxic metabolites, the liver's ability to maintain constant mass is critical for its function and organismal survival. Whereas during moderate and acute injuries, liver parenchymal cells, i.e., differentiated hepatocytes, reenter the cell cycle, proliferate and replenish the lost tissue, bipotential hepatobilliary progenitor cells (aka oval cells) were suggested as the main source of new hepatocytes and bile duct cells (cholangiocytes) under conditions that interfere with hepatocyte proliferation or cause their exhaustion (Alison et al., 2009; Boulter et al., 2013; Duncan et al., 2009; Itoh and Miyajima, 2014). Oval cells were postulated to serve as facultative stem cells residing in a specialized niche at the junction of bile canaliculi and ducts, the canal of Hering (Miyajima et al., 2014). Recent lineage tracing experiments, however, demonstrated that oval cells contribute minimally to liver parenchymal restoration after injury (Espanol-Suner et al., 2012; Malato et al., 2011; Rodrigo-Torres et al., 2014; Schaub et al., 2014; Tarlow et al., 2014a; Yanger et al., 2014), implying that mature hepatocytes are responsible for tissue restitution after liver injury, even though a recent report suggested that a population of ductal Lgr5$^+$ stem cells lead to hepatocyte formation in mice (Huch et al., 2013) and man (Huch et al., 2015) after in vitro propagation.

While maintaining liver mass and function, compensatory proliferation has a key role in liver carcinogenesis (Karin, 2006; Kuraishy et al., 2011). Genetic manipulations that increase hepatocyte death after toxic injury, such as ablation of IKKβ, (Maeda et al., 2005) IKKγ/NEMO (Luedde et al., 2007) or p38α (Hui et al., 2007; Sakurai et al., 2008) potentiate HCC development by enhancing compensatory hepatocyte proliferation. In fact, compensatory proliferation is the major tumor promoting mechanism that expands initiated hepatocytes not only in carcinogen-exposed livers but also during chronic liver diseases, such as non-alcoholic steatohepatitis (NASH), which progress to HCC (Nakagawa et al., 2014b). For most cancer types, the cell of origin is still unknown, fostering intense debates whether cancer arises from adult stem cells, transient amplifying cells or terminally differentiated cells that undergo reprogramming. A recent study suggested a high correlation between the lifetime risk of particular cancers with the number of cell divisions in the corresponding stem cell compartment (Tomasetti and Vogelstein, 2015). This observation implies that most cancers arise from actively dividing adult stem cells. Given the established link between tissue injury, inflammation and cancer (Kuraishy et al., 2011), it seems reasonable to assume that also in liver, the cells with the highest replicative potential are the ones that give rise to cancer. Correspondingly, oval cells were suggested as the most likely HCC progenitors (Sell and Leffert, 2008) and we had identified a population of HCC progenitor cells (HcPC) induced by diethylnitrosamine (DEN), that resemble oval cells in their transcriptomic profile (He et al., 2013). However, given the dependence of DEN metabolic activation on Cyp2E1, an enzyme that is only expressed in fully differentiated zone 3/pericentral hepatocytes (Kang et al., 2007), we suggested that HcPC are not derived from oval cells (He et al., 2013). Nonetheless, it is still formally possible that oval cells may give rise to NASH-induced HCC, a condition where oval cell expansion has been described (Richardson et al., 2007).

Unresectable HCC and end-stage liver diseases, such as decompensated cirrhosis, can only be treated by liver transplantation, but the availability of appropriate donor livers is limited. It is therefore necessary to find alternatives for liver transplantation. One possibility is transplantation of adult liver stem cells, but despite extensive research, the existence and identity of such cells remained elusive (Miyajima et al., 2014). The safety of donor cells is another issue, given the possible link to HCC development. It was recently shown that human ductal cells can be expanded and differentiated in vitro to transplantable hepatocytes (Huch et al., 2015; Schmelzer et al., 2007), but additional solutions to the problem should also be pursued.

The prior art has attempted to repair diseased liver using several approaches. For example, in one approach, hepatocytes are derived from patient induced Pluripotent Stem Cells (iPSCs). The procedure however, does not generate a fully functional hepatocyte and therefore the functional repair of diseased livers is not optimal. For example, transplantation of 1 million iPSCs resulted in only a 2% repopulation after 9 months (Zhu et al., Nature (2014) 508(7494): 93-7).

In another approach, hepatocytes are derived by expanding ductal cells (oval cells, liver progenitor cells, lgr5+ or Epcam+ liver cells), which are the only liver cells that can be grown and expanded in vitro, in contrast to hepatocytes, which cannot be cultured in vitro. Expanded ductal cells can be differentiated to hepatocyte-like cells. However, the problem with this strategy is again the failure to obtain fully differentiated hepatocytes. Consequently, when expanded ductal cells are transplanted into subjects with liver disease, they fail to fully prevent liver failure. For example, 500,000-800,000 ductal cells reached 1% of repopulation after 2-3 month and none of the animals survived (Huch et al., Nature (2013) 494(7436):247-50; Huch et al., Cell (2015) 160:299-312).

Thus, there remains a need for compositions and methods for identifying hepatocyte cells that may be isolated and propagated ex vivo, and that differentiate and transdifferentiate, after transplantation in vivo, into fully functional hepatocytes and other liver cells. Preferably, these transplanted hepatocyte cells are not tumorigenic.

SUMMARY OF THE INVENTION

The invention provides the discovery of the existence of hybrid hepatocyte (HybHP) cells. Thus, the invention provides purified mammalian hybrid hepatocyte (HybHP) cells, compositions comprising HybHP cells, methods for purifying HybHP cells, methods for in vitro culture of HybHP cells, and methods for using HybHP cells to repopulate and/or treat the liver of a subject in need thereof.

In one embodiment, the invention provides a purified mammalian hybrid hepatocyte (HybHP) cell that expresses at least one first protein marker of liver ductal (DC) cells and expresses at least one second protein marker of conventional hepatocyte (cHP) cells. In one embodiment, the HybHP cell is specifically bound to a first antibody to produce a first antibody-HybHP cell conjugate, and wherein the first antibody specifically binds to a first protein marker of liver ductal (DC) cells. In another embodiment, the HybHP cell in the first antibody-HybHP cell conjugate is specifically bound to a second antibody to produce a first antibody-HybHP cell-second antibody conjugate, wherein the second antibody specifically binds to a second protein marker of conventional hepatocyte (cHP) cells.

The invention also provides a composition comprising one or more of a purified HybHP cell described herein, and/or one or more of a first antibody-HybHP cell conjugate described herein, and/or one or more of a first antibody-HybHP cell-second antibody conjugate described herein.

The invention additionally provides a method for purifying a hybrid hepatocyte (HybHP) cell from a mammalian liver, the method comprising, a) preparing a single-cell suspension from the liver, b) combining the single-cell suspension with i) at least one first antibody that specifically binds to a first protein marker of liver ductal (DC) cells, and ii) at least one second antibody that specifically binds to a second protein marker of conventional hepatocyte (cHP) cells, wherein the combining is under conditions for specific binding of the at least one first antibody to the first protein marker, and of the at least one second antibody to the second protein, and wherein the specific binding produces a first composition that comprises a first antibody-HybHP cell-second antibody conjugate, and c) isolating the first antibody-HybHP cell-second antibody conjugate from the single-cell suspension, thereby producing a second composition that comprises a purified HybHP cell. In one embodiment, the second protein marker of cHP cells is overexpressed in the HybHP cells compared to cHP cells. In another embodiment, the second protein marker of cHP cells is underexpressed in the HybHP cells compared to cHP cells.

Also provided by the invention is a mammalian first antibody-HybHP cell-second antibody conjugate isolated by any one or more of the methods described herein. The invention also provides a composition comprising any one or more of the mammalian first antibody-HybHP cell-second antibody conjugate isolated by any one or more of the methods described herein.

The invention additionally provides a method for purifying a hybrid hepatocyte (HybHP) cell from a mammalian liver, the method comprising, a) preparing a single-cell suspension from the liver, b) substantially removing ductal cells from the single-cell suspension to obtain a first population of cells that contains conventional hepatocyte (cHP) cells and HybHP cells, c) combining the first population of cells with at least one first antibody that specifically binds to a first protein marker of liver ductal (DC) cells, wherein the combining is under conditions for specific binding of the at least one first antibody to the first protein marker, and wherein the specific binding produces a first composition that comprises a first-antibody-HybHP cell conjugate, and d) isolating the first antibody-HybHP cell conjugate from the first population of cells, thereby producing a second population of cells that comprises a purified HybHP cell.

The invention further provides a mammalian first antibody-HybHP cell conjugate isolated by any one or more of the methods described herein. Also provides is a composition comprising any one or more of the mammalian first antibody-HybHP cell conjugate isolated by any one or more of the methods described herein.

The invention further provides a method for propagating mammalian hybrid hepatocyte (HybHP) cells in vitro, comprising a) combining purified mammalian HybHP cells with culture medium that is suitable for in vitro growth of liver ductal (DC) cells to produce a first culture composition, and b) incubating the first culture composition in vitro under conditions for growth of liver DC cells, thereby propagating the HybHP cells. In one embodiment, the combining step comprises introducing the purified HybHP cells into a three-dimensional matrix.

The invention also provides a method for repopulating the liver of a mammalian host subject in need thereof, comprising transplanting purified hybrid hepatocyte (HybHP) cells into the host subject to produce a treated subject that comprises the HybHP cells, wherein the transplanting is under conditions for repopulating the liver of the host subject. In one embodiment, the treated subject comprises a higher number of the HybHP cells than the host subject. In another embodiment, the HybHP cell is specifically bound to a first antibody to produce a first antibody-HybHP cell conjugate, and wherein the first antibody specifically binds to a first protein marker of liver ductal (DC) cells. In a further embodiment, the HybHP cell in the first antibody-HybHP cell conjugate is specifically bound to a second antibody to produce a first antibody-HybHP cell-second antibody conjugate, wherein the second antibody specifically binds to a second protein marker of conventional hepatocyte (cHP) cells. In one particular embodiment, repopulating is at least 20%. In another embodiment, the host subject has liver damage. In another embodiment, repopulating treats the liver damage in the treated subject. In a further embodiment, the purified HybHP cells are obtained from a mammalian donor subject, and wherein the host subject and the donor subject are different individuals. In a particular embodiment, the purified HybHP cells are obtained from a mammalian donor subject, and wherein the host subject and the donor subject are the same individual. In another embodiment, repopulating does not produce hepatocellular carcinoma (HCC). In a particular embodiment, the purified HybHP cells are propagated in vitro prior to the transplanting. In a particular embodiment, the method further comprises the step of detecting the presence of the transplanted HybHP cells and/or their progeny (e.g., cHP cells and/or DC cells) in the treated subject.

The invention further provides a method for treating liver damage in a mammalian host subject in need thereof, comprising transplanting a therapeutically effective amount of purified hybrid hepatocyte (HybHP) cells into the host subject to produce a treated subject that comprises the HybHP cells, wherein the transplanting is under conditions for repopulating the liver of the host subject, thereby treating the liver damage. In one embodiment, the treated subject comprises a higher number of the HybHP cells than the host subject. In another embodiment, the HybHP cell is specifically bound to a first antibody to produce a first antibody-HybHP cell conjugate, and wherein the first antibody specifically binds to a first protein marker of liver ductal (DC) cells. In a further embodiment, the HybHP cell in the first antibody-HybHP cell conjugate is specifically bound to a second antibody to produce a first antibody-HybHP cell-second antibody conjugate, wherein the second antibody specifically binds to a second protein marker of conventional hepatocyte (cHP) cells. In a particular embodiment, the method further comprises the step of detecting the presence of the transplanted HybHP cells and/or their progeny (e.g., cHP cells and/or DC cells) in the treated subject.

In one embodiment, the invention provides a method for isolating a hybrid hepatocyte (HybHP) cell comprising enriching a cell suspension of liver cells for a cell that express at least one gene that is specific to liver ductal (DC) cells, and at least one gene that is specific to conventional hepatocyte (cHC) cells. For example, FIG. 5 shows FACS separation of conventional hepatocytes (cHP), bile duct cells (BD) and Hybrid Hepatocytes (HybHP) from a liver collagenase digest after exclusion of dead cells and cell doublets and gating based on size/granularity (FCS/SSC) and tdTomato expression. In one embodiment, said enriching comprises fluorescence activated cell sorting (FACS). In one embodiment, said enriching comprises incubating said liver cell suspension with antibody that binds to said one or more specific marker of said HybHP cells. In one embodiment, said liver cells are from a mammal. In one embodiment, said mammal is human. In one embodiment, said enriching comprises reducing the number of conventional hepatocyte (cHP) cells from said cell suspension. In one embodiment, said enriching comprises reducing the number of bile duct (BD) cells from said cell suspension. In one embodiment, said enriching comprises reducing the number of oval cells (OCs) from said cell suspension.

The invention also provides a method for treating a subject in need thereof by transplanting isolated hybrid hepatocyte (HybHP) cells to said subject. In one embodiment, proliferation of said HybHP does not produce cancer cells. For example, data herein show the 95% Credibility Intervals for the % of positive tumors compatible with the number of negative tumors observed (DEN 106/106, STAM 62/62 and MUP-uPA+HFD 79/79; all negative). In all cases, the upper boundary of the interval is very low (around 5%), demonstrating that in the three HCC models we had analyzed, HybHP give rise to the tumors. In one embodiment, said subject has liver disease. In one embodiment, said liver disease comprises hepatocellular carcinoma (HCC). In one embodiment, said liver disease comprises cirrhosis. In one embodiment, said subject has liver injury. In one embodiment, said subject has liver inflammation. In one embodiment, said transplanting is intrasplenic. In one embodiment, said subject is a mammal. In one embodiment, said mammal is human.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. HybHP make a major contribution to parenchymal restoration after liver injury. (A) Sox9-Cre$^{ERT}$; R26R$^{YFP}$; MUP-uPA mice (9 weeks old) were analyzed as in FIG. 1. 99.9% YFP$^+$ labeled (green) cells are ductal/oval CK19$^+$ cells (red). (B,C) Sox9-Cre$^{ERT}$; R26R$^{YFP}$; MUP-uPA mice were injected with 100 mg/kg tamoxifen at P10 and analyzed as above at 5 weeks (2 weeks after damage onset) (B) or at 12 weeks (C). (D) Tamoxifen (100 mg/kg)-injected, Sox9-Cre$^{ERT}$; R26R$^{YFP}$ mice (8 weeks old), received 2 weekly CCl$_4$ injections for 6 weeks. Livers were excised and analyzed as above. YFP$^+$ HybHP (green) occupied a large portion of the liver parenchyma. (E) Without CCl$_4$ treatment YFP$^+$ cells did not expand. (F) Acute CCl$_4$ administration resulted in a minor HybHP YFP$^+$ cell expansion after 4 weeks. Arrows, ductal cells (CK19$^+$, red). Scale bar, 50 µm.

FIG. 3. Clonal labeling confirms HybHP role in liver injury repair. (A) A scheme outlining clonal labeling of HybHP with dual recombinase NZG reporter. A nuclear LacZ marker cassette is first expressed upon removal of the loxP (yellow arrows) flanked STOP cassette (PGK-Neo). A GFP marker is then expressed upon sequential Cre- and FLPo-dependent excisions of the STOP and Frt-flanked LacZ cassettes, respectively. (B) Sox9-Cre$^{ERT}$; NZG mice (4-6 weeks old) were injected with 100 mg/kg of tamoxifen and 10 days later given 20 mg/kg tamoxifen. Ductal cells and HybHP were positive for nuclear LacZ (arrows and arrowheads, respectively), but not a single cell was GFP positive. (C-E) The same mice were first treated with tamoxifen as above, and then were injected with $10^9$ or $5\times10^{11}$ Adeno- or AAV-FLPo viral particles, respectively. (C) After 2 weeks, livers were analyzed. Some HybHP were GFP$^+$ and nuclear LacZ-(green arrows). (D) Liver sections were stained for CK19. HybHP are CK19$^-$. (E) Liver sections were stained for HNF4α. GFP$^+$ HybHP are HNF4α$^+$. (F) Sox9-Cre$^{ERT}$; NZG mice were tamoxifen treated followed by AAV-FLPo administration and challenged with an acute dose of CCl$_4$, or 1, 6 or 12 low CCl$_4$ doses. Livers were excised and analyzed as in (D). (G) Quantification of cell number per clone in each experimental group. No treatment: 750 independent clones, n=3; acute CCl$_4$: 939 independent clones, n=3; 1 low dose: 469 independent clones, n=3; 6 low doses, 626 independent clones, n=3; 12 low doses: 756 independent clones, n=4. ****=P value<0.0001 based on one way Anova with multiple comparisons. Scale bar, 50 μm. Asterisks—central veins. n.s.—non significant.

2A. (C) Immunostaining for YFP (green) and GS (red) of liver sections from the same Sox9-Cre$^{ERT}$; R26R$^{YFP}$ tamoxifen treated mice shown in FIG. 2B. Scale bars, 50 μm. Arrows—HybHP-derived GS$^+$ hepatocytes.

FIG. 10. Genetic clonal analysis of hepatocytes reveals predominant clonal growth from the portal tract. Related to FIG. 2. Whole slide scans of IF images of YFP-, Sox9- and DAPI-stained liver sections from: (A) TTR-Cre$^{ERT}$; R26R$^{YFP}$ mice that were injected with 100 mg/kg tamoxifen at P7-10. Scattered hepatocytes were labeled with YFP (green). When adult animals were tamoxifen injected at 6 weeks or later no ductal cells were labeled, whereas tamoxifen injection at P7-10 resulted in 0.5% of ductal cells (Sox9$^+$) becoming YFP$^+$, although most portal tracts (90%) lacked YFP$^+$ cells. (B) Livers of TTR-Cre$^{ERT}$; R26R$^{YFP}$; MUP-uPA mice without tamoxifen treatment. No YFP$^+$ cells were detected. (C) TTR-Cre$^{ERT}$; R26R$^{YFP}$; MUP-uPA mice were injected with 100 mg/kg of tamoxifen at P7, sacrificed at 5 weeks of age and analyzed as above. (D) Same mice as above that were sacrificed and analyzed at 8 weeks of age. At that point most labeled hepatocytes were eliminated and clonal expansion was mainly seen in the portal region. Arrows: parenchymal hepatocyte clones; arrowheads: clones initiated at periportal areas. (E) Livers of TTR-Cre$^{ERT}$; R26R$^{YFP}$ mice injected with 100 mg/kg tamoxifen at 6 weeks of age contain scattered YFP hepatocytes (green). (F) Livers of TTR-Cre$^{ERT}$; R26R$^{YFP}$ mice treated with biweekly CCl$_4$ injections for 6 weeks. Several extended clones contacting the portal tract are highlighted with arrows. Asterisks—central veins.

Figures 11A, 11B, 11C:
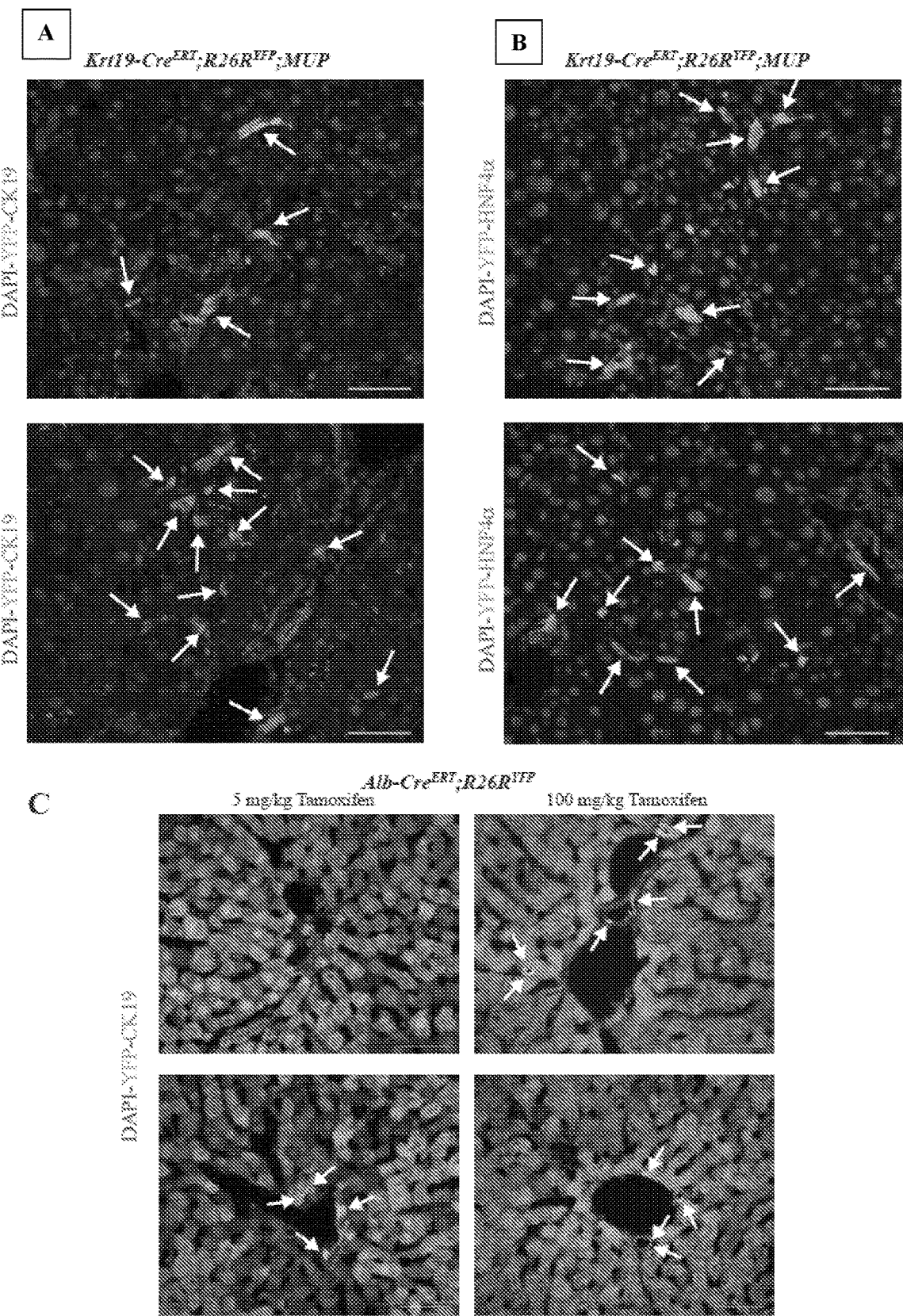

FIG. 11. Lineage tracing of CK19$^+$ cells in MUP-uPA mice and genetic labeling with Alb-Cre$^{ERT}$. Related to FIG. 2. (A,B) CK19-Cre$^{ERT}$; R26R$^{YFP}$; MUP-uPA mice were injected twice with 100 mg/kg of tamoxifen at P7 and P10. At 8 weeks of age, livers were excised, sectioned and stained with GFP and CK19 antibodies (A) or GFP and HNF4α antibodies (B). For each staining combination, two different regions are shown. Arrows—oval cells. (C) IF analysis of livers from tamoxifen treated (5 mg/kg or 100 mg/kg) Alb-Cre$^{ERT}$; R26R$^{YFP}$ mice. CK19$^+$/YFP$^+$ double positive cells are marked by arrows. Scale bar, 50 μm.

FIG. 12. Flow cytometric analysis of sorted HybHP, cHP and BD populations. Related to FIG. 5. (A) Flow cytometric analysis of cells prepared by collagenase perfusion of livers from WT and Sox9-Cre$^{ERT}$; R26R$^{YFP}$ mice treated with 100 mg/kg tamoxifen. The brightness of the YFP marker was insufficient to allow separation of the positive and negative populations for reliable purification. (B) Flow cytometric analysis and gating scheme for sorting of HybHP and cHP from cell suspensions prepared by collagenase perfusion of livers from Sox9-Cre$^{ERT}$; R26Rtd$^{Tomato}$ mice treated as in (A). After exclusion of doublets and dead cells using fixable viability dye (left panel), vital cells (62%) were further gated based on size/granularity (middle, cHP gate). tdTomato (tdT) positive cells indicated HybHP (right). (C,D) To confirm the gating scheme for cHP and HybHP, the cells were stained with antibodies specific for HNF4α (C) and CK19 (D), showing that cHP and HybHP expressed HNF4α but were negative for CK19 (purity 97%). The corresponding isotype controls are shown in the left panels. (E) Flow cytometric analysis and gating scheme for sorting of isolated BD cells from same animals as in (B). After exclusion of doublets and dead cells using fixable viability dye (left panel), vital cells (83.5%) were further gated based on size/granularity (middle, BD gate). tdTomato (tdT) positive cells indicated BD (right). (F,G) To confirm the gating scheme for BD cells, the cells were stained for HNF4α (F) and CK19 (G), showing that BD cells did not express HNF4α and were positive for CK19 (purity of 97%). The corresponding isotype controls are shown in left panels.

FIG. 13. HybHP express a few ductal-specific genes and numerous hepatocyte-specific genes. Related to FIG. 5. (A) Clustering analysis showing distances based on normalized Reads per Kilobase per Million base pairs (RPKM) values from the three populations analyzed by Hclust with R. (B) The four classes of differentially expressed genes shown in panel B were analyzed according to function. Selection of the top functional entries by Benjamini corrected P value<0.05 are displayed. Class 3 did not show any functional enrichment and is not depicted. (C) Livers from WT animals were stained with Sox9 and Opn antibodies and visualized with TSA (red) and regular staining for CK19 (green). Arrows show HybHP. Scale bars, 20 μm. (D) TSA-immunofluorescence using antibodies for the proteins indicated in red and regular staining for GFP in Sox9-GFP transgenic mouse liver sections. Arrows indicate HybHP expressing the corresponding markers whereas arrowheads indicate normal hepatocytes expressing the same marker. Scale bars, 50 μm. (E) A hypothetical model illustrating the hybrid nature of HybHP. The two curves show profiles of bile duct-specific and zone 1 hepatocyte-specific genes.

Figures 7A, 7B, 7C, 7D:
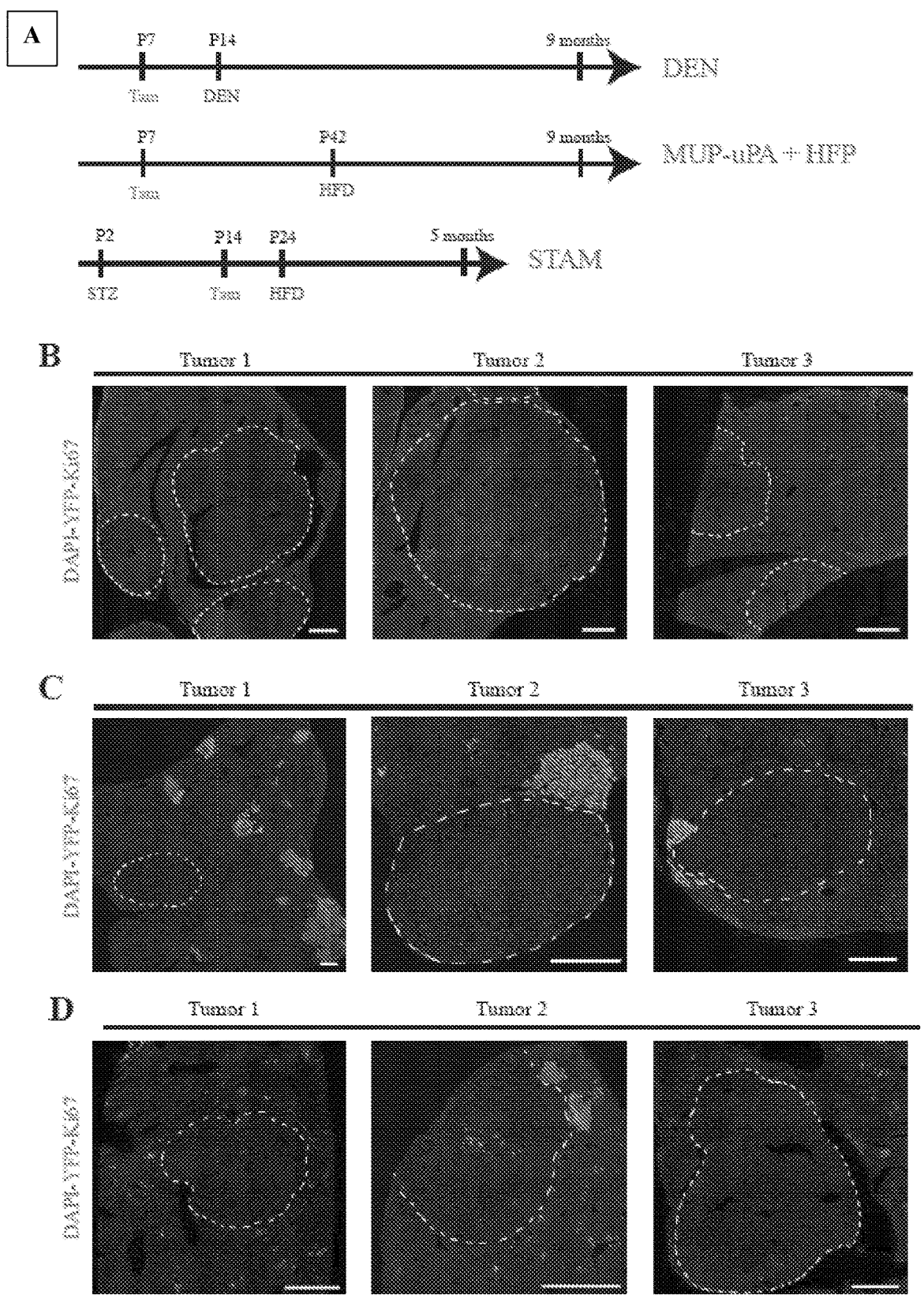
FIG. 7. Neither HybHP nor oval cells preferentially give rise to HCC. (A) Experimental design for HybHP and OC lineage tracing in three different HCC models using Sox9-Cre$^{ERT}$; R26R$^{YFP}$ or Sox9-Cre$^{ERT}$; R26R$^{YFP}$; MUP-uPA mice. (B-D) Ki67 immunofluorescence and morphology were used to locate tumor nodules (delineated by a dashed line) in whole slide scans. None of the tumor areas contained YFP$^+$ cancer cells. Three representative examples are shown for each HCC model. Scale bars, (B), 0.5 mm; (A,C) 1 mm.

FIG. 14. The relationship between HybHP expansion and the oval cell response. Related to FIG. 7. (A) Portion of a whole slide scan from Sox9-Cre$^{ERT}$; R26R$^{YFP}$; MUP mice used in FIGS. 2 and 9, stained with DAPI (blue), YFP (green) and CK19 (red). (B) Portion of a whole slide scan of STAM mouse liver, stained as in (A). (C) Portion of a whole slide scan of liver from Sox9-Cre$^{ERT}$; R26R$^{YFP}$ mice treated with 100 mg/kg of tamoxifen and fed with CDE diet for 3 weeks and stained as in (A). Arrows—tissue areas with clonal expansion of HybHP; arrowheads—regions showing oval cell response but no HybHP clonal expansion. Scale bars: B, 250 μm; A and C, 500 μm. Asterisks—central veins.

FIG. 15. RNAseq statistical analysis. Related to FIG. 5. (A,B) Quantile-quantile plots comparing the expected value of chi-squared goodness-of-fit statistics (x-axis) with their observed values (y-axis) for gene-level counts. (A) Poisson distribution; (B) Negative Binomial distribution. (C) Quantile-quantile plot comparing expected z-scores (x-axis) under the Normal distribution with those from the observed normalized log 2-RPKM. Black dots indicate the average observed quantile, and the straight line the expected quantile if gene-level expressions truly followed a Normal distribution. (D) Quantile-quantile plot comparing expected quantiles under a Gamma distribution (x-axis) with the observed normalized log 2-RPKM values (y-axis). (E) Principal components plot of the observed log 2-RPKM expression. (F) Principal components plot with observed log 2-RPKM data and that simulated from the GaGa model (grey) under the null hypothesis that expression is equal in the HybHP and cHP groups for all genes. (G) Density plot for GaGa simulated ratios of within/between groups distance (rdist) under the null hypothesis of no differences between HybHP-cHP groups. Dashed line indicates observed rdist=0.83. (H) Histogram of percentage of genes estimated by GaGa to arise from Patterns 2-4 when data are simulated from the null hypothesis by the GaGa model. Dashed line indicates the 0.3% estimated in the observed data. (I) Same as in (F) but for simulated log 2-RPKM computed from counts generated under the Tweedie model. (J) Same as in (G) using the Tweedie model to simulate data under the null hypothesis. (K) Same as in (H) using the Tweedie model to simulate data under the null hypothesis. (L) Fold changes BDg/cHPg (x-axis) versus HybHPg/cHPg (y-axis) in the observed data for 770 genes with HybHPg/cHPg above 2 or below −2, read count >10 in the cHP group and total read count >100. Blue boundaries correspond to lower and upper boundaries of intervals containing 95% of the HybHPg(b)/cHPg(b) values simulated under the mixture hypothesis.

Figure 16:
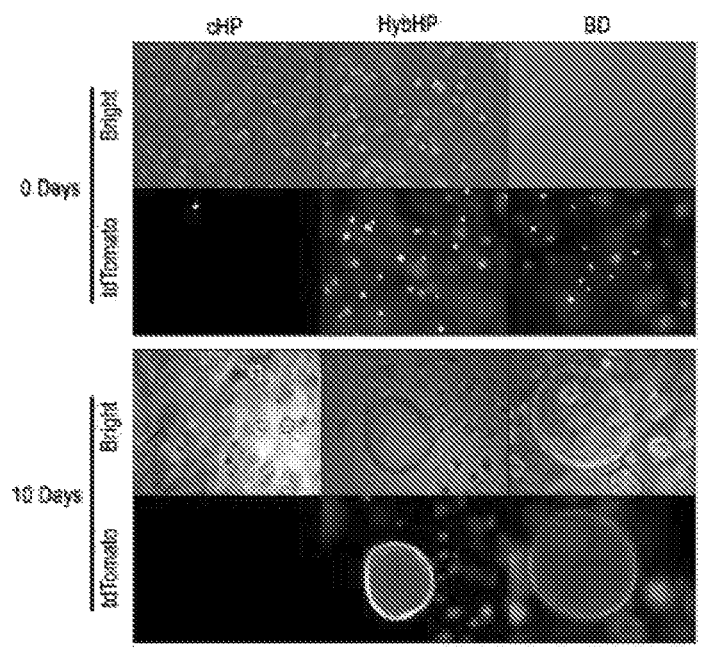

FIG. 16. Conventional hepatocytes (cHP), Hybrid Hepatocytes (HybHP) and Bile duct cells (BD) were sorted from liver homogenates of tamoxifen treated Sox9CreERT; ROSAtdTomato mice. Single cells from the three populations were seeded in matrigel and organoid media and imaged at different time points after seeding.

DEFINITIONS

"Hepatocyte cells" are highly polarized epithelial cells and form cords. Hepatocytes account for approximately 50% of total liver cells and 80% of the volume of the organ. Their basolateral surfaces face fenestrated sinusoidal endothelial cells, facilitating the exchange of materials between hepatocytes and blood vessels. Tight junctions formed between hepatocytes create a canaliculus that surrounds each hepatocyte. Bile secreted from mature hepatocytes is exported sequentially through bile canaliculi surrounded by the apical membrane of neighboring hepatocytes, intrahepatic bile ducts, extrahepatic bile ducts, and, finally, the duodenum. The bile duct is formed by a specialized type of epithelial cell called a cholangiocyte. The term "hepatocyte" cell includes conventional hepatocyte (cHP) cells, and the invention's newly discovered hybrid hepatocyte (HybHP) cells.

"Conventional hepatocyte cell" and "cHP cell" interchangeably refer to a hepatocyte cell that expresses at least one protein marker encoded by the genes in text that is neither in bold nor in italics in Table 2. The cHP cells co-migrate with HybHP cells, and differentially migrates from ductal cells, on density gradients (Examples 1, 2).

"Ductal cell" and "DC cell" interchangeably refer to a liver cell that expresses at least one protein marker encoded by the genes in bold italic text in Table 1 and Table 3. DC cells differentially migrates from cHP cells and from HybHP cells on density gradients (Examples 1, 2). Ductal cells include oval cells (OCs) and bile duct (BD) cells.

"Oval cell" is an ovoid cell observed in animal models of liver carcinogenesis (Farber, E. (1956) Cancer Res. 16, 142-148), and is sometimes introduced in literature as a synonym for liver stem cells. Oval cells have been extensively characterized histologically, which cumulatively suggests that they have bipotential differentiation capability toward both hepatocytes and cholangiocytes (Miyajima et al., 2014).

"Bile duct" cells (also referred to as "BD" cells) are located in the bile duct.

"Density gradient" is a spatial variation in density over an area. "Density gradient centrifugation" is a procedure for separating cells in which the sample is placed on a preformed gradient (e.g., percoll, Stractan, etc.). Upon centrifugation either by rate zonal or equilibrium procedures, the cells are banded in the gradient and can be collected as a purified fraction.

"Purified," "purify," "isolate," and grammatical equivalents thereof when in reference to a desirable component (such as cell type, protein, nucleic acid sequence, etc.) refer to the reduction in the amount of at least one undesirable component (such as another cell type, protein, nucleic acid sequence, etc.) from a sample. This reduction may be by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, from 90% to 100%, from 95% to 100%, from 99% to 100%, and most preferably by 100%. Thus, purification results in "enrichment" (i.e., an increase) in the amount of the desirable component relative to one or more undesirable component. For example, "purified HybHP cells" refers to HybHP cells that are purified from cHP cells and from DC cells. Preferably, the purified HybHP cells are substantially free from cHP cells and from DC cells. In another example, "purified first antibody-HybHP cell-second antibody conjugate" and "purified first-antibody-HybHP cell conjugate" refer to conjugates containing purified HybHP cells. Methods for purifying of single cells are known in the art, including fluorescence-activated cell sorting (FACS), magnetic-activated cell sorting (MACS), etc. Single-cell purification methods (such as FACS, MACS, etc.) may employ direct labeling of the antigen of interest using a primary antibody that specifically binds to the antigen of interest. Alternatively, purification methods employ indirect labeling of the antigen of interest using a secondary antibody that specifically binds to the Fc portion of the primary antibody, biotin, and/or to fluorescein isothiocyanate (FITC). Indirect labeling may also use Streptavidin, instead of the secondary antibody, which binds to biotin on the primary antibody.

"Fluorescence-activated cell sorting" and "FACS" interchangeably refer to a method for sorting a heterogeneous mixture of biological cells based upon the specific light scattering and fluorescent characteristics of each cell, thus purifying cells of interest (e.g., HybHP cells). FACS is particularly preferred for isolating a target cell population (e.g., HybHP cells) at high purity, when the target cell population expresses a very low level of the identifying marker or when cell populations require separation based on differential marker density. In addition, FACS is a particularly desired for technique to isolate cells based on internal staining and/or intracellular protein expression, such as a genetically modified fluorescent protein marker. FACS allows the purification of individual cells based on size, granularity and fluorescence. In order to purify cells of interest, they are first stained with a fluorescently-tagged primary antibody that recognizes specific surface markers on the desired cell population. Negative selection of unstained cells is also possible. Basu et al. (2010) "Purification of Specific Cell Population by Fluorescence Activated Cell Sorting (FACS)" J Vis Exp. (41): 1546. doi: 10.3791/1546.

"Magnetic-activated cell sorting" and "MACS" interchangeably refer to a method for purifying various cell populations depending on their surface antigens. In one embodiment, MACS uses nanoparticles conjugated to an antibody against an antigen of interest (e.g., on the surface of HybHP cells). In another embodiment, MACS uses magnetic nanoparticles coated with anti-fluorochrome antibodies that are incubated with the fluorescent-labelled antibodies against the antigen of interest for cell separation with respect to the antigen (such as by using anti-immunoglobulin MicroBeads, anti-biotin MicroBeads, streptavidin MicroBeads, and anti-fluorochrome MicroBeads).

The term "population of cells" refers to a plurality of cells, i.e., more than one cell. The population may be a pure population comprising one cell type. Alternatively, the population may comprise more than one cell type. In the present invention, there is no limit on the number of cell types that a cell population may comprise.

Cell "marker molecule" refer to a molecule (such as protein, nucleotide sequence, etc.) that is present on, and/or is produced by, a particular type of cell (such as cancer cell, epithelial cell, fibroblast cell, muscle cell, synovial cell, stem cell, embryonic cell, etc.), at a different level (e.g., a higher level or lower lever, preferably a higher level) than other types of cells. Cell marker molecules may be used to distinguish one cell type of one or more other cell types.

"Mammal" includes a human, non-human primate, murine (e.g., mouse, rat, guinea pig, hamster), ovine, bovine, ruminant, lagomorph, porcine, caprine, equine, canine, feline, ave, etc. In one preferred embodiment, the mammal is murine. In another preferred embodiment, the mammal is human.

A subject "in need" of treatment with the invention's methods and/or compositions includes a subject that is "suffering" from liver damage (i.e., a subject that is experiencing and/or exhibiting one or more symptoms of liver damage), and subject "at risk" of liver damage. A subject "in need" of treatment includes animal models of liver damage. Subject "at risk" of liver damage refers to a subject that is not currently exhibiting liver damage symptoms and is predisposed to expressing one or more symptoms of the disease. This predisposition may be based on family history, genetic factors, environmental factors such as exposure to detrimental compounds present in the environment, etc.). It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

The term "conjugate" when in reference to a cell and antibody refers to a cell that is linked (directly or indirectly) to an antibody via an antigen that is expressed on the cell surface. Antibodies bind antigens through weak chemical interactions, and bonding is essentially non-covalent, such as electrostatic interactions, hydrogen bonds, van der Waals forces, and hydrophobic interactions. For example a "First-antibody-HybHP cell conjugate" refers to a HybHP cell that is linked to a first antibody via an antigen that is expressed on the surface of the HybHP cell. Also, a "HybHP cell-first antibody-second antibody conjugate" refers to a HybHP cell that is linked to a first antibody via a first antigen that is expressed on the surface of the HybHP cell, and also linked to a second antibody via a second antigen that is expressed on the surface of the HybHP cell.

The terms "specifically binds," "specific binding," and grammatical equivalents, when made in reference to the binding of antibody to a molecule (e.g., peptide) refer to an interaction of the antibody with one or more epitopes on the molecule where the interaction is dependent upon the presence of a particular structure on the molecule. For example, if an antibody is specific for epitope "A" on the molecule, then the presence of a protein containing epitope A (or free, unlabeled A) in a reaction containing labeled "A" and the antibody will compete with, and thus reduce, the amount of labeled A bound to the antibody.

"Overexpression," "upregulation," and grammatical equivalents, when used in reference to a protein in a cell of interest (such as a HybHP cell, cHP cell, DC cell, etc.) refers to the presence of a higher level of the protein, and/or its encoding mRNA, in the cell of interest compared to another cell (such as a control HybHP cell, cHP cell, DC cell, etc.).

"Underexpression," "downregulation," and grammatical equivalents, when used in reference to a protein in a cell of interest (such as a HybHP cell, cHP cell, DC cell, etc.) refers to the presence of a lower level of the protein, and/or its encoding mRNA, in the cell of interest compared to a another cell (such as a control HybHP cell, cHP cell, DC cell, etc.).

The terms "increase," "elevate," "raise," and grammatical equivalents (including "higher," "greater," etc.) when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a ligand to a receptor, specificity of binding of two molecules (such as an antigen and antibody), affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of the molecule, cell, and/or phenomenon in the first sample (or in the first subject) is higher than in the second sample (or in the second subject) by any amount that is statistically significant using any art-accepted statistical method of analysis. In one embodiment, the quantity of the molecule, cell, and/or phenomenon in the first sample (or in the first subject) is at least 10% greater than, at least 25% greater than, at least 50% greater than, at least 75% greater than, and/or at least 90% greater than the quantity of the same molecule, cell, and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell, and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a ligand to a receptor, specificity of binding of two molecules (such as an antigen and antibody), affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of molecule, cell, and/or phenomenon in the first sample (or in the first subject) is lower than in the second sample (or in the second subject) by any amount that is statistically significant using any art-accepted statistical method of analysis. In one embodiment, the quantity of molecule, cell, and/or phenomenon in the first sample (or in the first subject) is at least 10% lower than, at least 25% lower than, at least 50% lower than, at least 75% lower than, and/or at least 90% lower than the quantity of the same molecule, cell, and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell, and/or phenomenon in the second sample (or in the second subject). In one embodiment, the first sample (or the first subject) is exemplified by, but not limited to, a sample (or subject) that has been manipulated using the invention's compositions and/or methods. In a further embodiment, the second sample (or the second subject) is exemplified by, but not limited to, a sample (or subject) that has not been manipulated using the invention's compositions and/or methods. In an alternative embodiment, the second sample (or the second subject) is exemplified by, but not limited to, a sample (or subject) that has been manipulated, using the invention's compositions and/or methods, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the invention's compositions and/or methods is sought to be determined on one sample (or subject). In another embodiment, the first and second samples (or subjects) may be different, such as when comparing the effect of the invention's compositions and/or methods on one sample (subject), for example a patient participating in a clinical trial and another individual in a hospital.

The terms "alter" and "modify" when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a ligand to a receptor, specificity of binding of two molecules (such as an antigen and antibody), affinity of binding of two molecules, disease symptom, specificity to disease, sensitivity to disease, affinity of binding, enzyme activity, etc.) refer to an increase and/or decrease.

"Substantially the same," "without substantially altering," "substantially unaltered," and grammatical equivalents, when in reference to the level of any molecule (e.g., amino acid sequence, and nucleic acid sequence, antibody, etc.), cell, and/or phenomenon (e.g., level of expression of a gene, disease symptom, level of binding of two molecules such as binding of a ligand to a receptor, specificity of binding of two molecules (such as an antigen and antibody), affinity of binding of two molecules, disease symptom, specificity to disease, sensitivity to disease, affinity of binding, enzyme activity, etc.) means that the quantity of molecule, cell, and/or phenomenon in the first sample (or in the first subject) is neither increased nor decreased by a statistically significant amount relative to the second sample (or in a second subject). Thus in one embodiment, the quantity of molecule, cell, and/or phenomenon in the first sample (or in the first subject) is from 90% to 100% (including, for example, from 91% to 100%, from 92% to 100%, from 93% to 100%, from 94% to 100%, from 95% to 100%, from 96% to 100%, from 97% to 100%, from 98% to 100%, and/or from 99% to 100%) of the quantity in the second sample (or in the second subject).

The term "composition," such as when made in reference to a composition comprising a desired component (such as HybHP cell, first-antibody-HybHP cell conjugate, first antibody-HybHP cell-second antibody conjugate, etc.) refers to any container, receptacle, and/or medium that can receive and/or contain the desired component. Thus, the term composition includes aqueous solutions (such as culture medium), three-dimensional matrix (such as matrigel, collagen, agar, etc.), flask, petri dish, multi-well dish, etc.

The terms "propagating," "culturing," and "growing," when made in reference to target cells, are interchangeably used to refer to increasing the number of the target cells.

The term "in vivo" refers to the natural environment (e.g., within an organism, tissue, and/or a cell).

The term "ex vivo" refers to an environment outside an organism.

The term "in vitro" refers to an ex vivo environment that includes manipulation under artificially-created conditions (e.g., culture medium, cell culture, transfection, assay) and/or using laboratory equipment (e.g., flasks, test tubes, petri dishes, multiwell plates, etc.).

The term "culture medium" refers to a nutritive substance that is suitable to support maintenance and/or growth of cells in vitro (i.e., cell cultures). A culture medium includes, for example, liquid media, and three-dimensional media. A culture medium includes salts (e.g., sodium chloride), carbohydrates (e.g., sugar), proteins (e.g., serum), etc.

"Three-dimensional media," "3D media," and "three-dimensional matrix" interchangeably refer to an artificially-created environment (e.g., matrigel, collagen, agar, etc.) in which biological cells are permitted to grow or interact with their surroundings in all three dimensions. This is in contrast to growing cells in "two-dimensional" (2D) monolayers (e.g., on a petri dish) because the 3D model more accurately models the in vivo cell environment.

The term "treating" liver damage interchangeably refers to delaying, reducing, palliating, ameliorating, stabilizing, preventing and/or reversing one or more symptoms (such as objective, subjective, pathological, clinical, sub-clinical, etc.) of liver damage. Symptoms of liver damage may be assessed by, for example, biopsy and histology, and blood tests to determine levels of relevant enzymes (e.g., enzymes involved in metabolism, such as aspartate aminotransferase (AST), alanine aminotransferase (ALT), alkaline phosphatase, 5' Nucleotidase, gamma-glutamyl transpeptidase (GGT)), levels of proteins involved in normal blood clotting (e.g., prothrombin time (PT) using international normalized ratio (INR) and/or partial thromboplastin time (PTT)), levels of albumin and/or bilirubin, levels of circulating antigen and/or antibody, and imaging tests (e.g., to detect a decrease in the growth rate or size of hepatocellular carcinoma).

The terms "therapeutic amount," "pharmaceutically effective amount," and "therapeutically effective amount," are used interchangeably herein to refer to an amount that is sufficient to achieve a desired result, such as treating liver damage, and/or repopulating the liver.

"Antibody" refers to an immunoglobulin (e.g., IgG, IgM, IgA, IgE, IgD, etc.) and/or portion thereof that contain a "variable domain" (also referred to as the "$F_V$ region") that specifically binds to an antigen. More specifically, variable loops, three each on the light ($V_L$) and heavy ($V_H$) chains are responsible for binding to the antigen. These loops are referred to as the "complementarity determining regions" ("CDRs") and "idiotypes." In one embodiment, the invention's antibodies are "monoclonal antibodies" ("MAbs") produced by a single clone of hybridoma cells.

DESCRIPTION OF THE INVENTION

The invention provides the discovery of the existence of hybrid hepatocyte (HybHP) cells. These cells are superior to any known cell type in repairing diseased and/or injured liver. This new and distinct population of hepatocytes is located at the periportal region that expresses several bile duct enriched genes. Hybrid Hepatocytes expand upon liver injury and form larger and more stably differentiated clones than other hepatocytes, and can also transdifferentiate into bile duct cells. Data herein demonstrate that in $Fah^{-/-}$ mice, which suffer chronic and fatal liver injury (Grompe et al., 1995), HybHP show higher regenerative capacity than normal hepatocytes and are far superior to oval cells. Neither HybHP nor oval cells serve as the origin for HCC in three independent mouse models, including two models of NASH-driven HCC (Fujii et al., 2013; Nakagawa et al., 2014b) (FIG. 7). These results demonstrate that the HybHP cells with the highest proliferative potential in a given tissue, may not necessarily be the ones that give rise to cancer.

The invention's compositions and methods are useful in the treatment of liver damage, liver tissue engineering, transplantation back into the donor subjects to generate a HLA compatible HybHP cell biobank and/or to treat other subjects.

The invention is further described under A) Purified hybrid hepatocyte (HybHP) cells and compositions comprising the, B) Methods for isolating HybHP cells, C) Methods for in vitro culture of HybHP cells, and D) Methods for repopulating the liver and treating liver damage.

A) Purified Hybrid Hepatocyte (HybHP) Cells and Compositions Comprising them

Compensatory proliferation triggered by liver damage is required for liver regeneration and maintenance of mass and function, but is also a potent tumor promoter giving rise to hepatocellular carcinoma (HCC). Despite extensive investigation, the nature of the cells responsible for liver regeneration or HCC development remains obscure.

Data herein demonstrate that the primary cell type responsible for regeneration of the liver parenchyma is the newly described HybHP. Yet, despite their high regenerative potential and extensive expansion during chronic liver injuries, which promote HCC development (Hui et al., 2007; Maeda et al., 2005; Nakagawa et al., 2014b), data herein show that HybHP are not the preferential origin for HCC in the 3 different liver cancer models we have examined herein. Thus, in contrast to the skin and the intestine, the liver does not contain a specialized compartment of adult or reserve stem cells that maintains tissue homeostasis and expands upon liver damage to restore tissue mass. A recent analysis of relative cancer rates at different tissue sites revealed a correlation with rates of cell division in most tissues and gave rise to the suggestion that the majority of cancer originates from adult tissue stem cells (Tomasetti and Vogelstein, 2015). This does not seem to apply to liver, in which HybHP generate new hepatocytes only upon liver damage but rarely give rise to cancer.

i) Hybrid Hepatocytes as a New Hepatocyte Subpopulation

Hepatocyte diversity has been long appreciated, especially in the context of metabolic zonation across the portal to central axis (Jungermann and Katz, 1989). However, it has been difficult to analyze the distinct properties of different hepatocyte populations under physiological conditions, although uni-zonal livers were generated through genetic manipulation of the Wnt-β-catenin signaling pathway (Benhamouche et al., 2006). Using the ductal transcription factor Sox9 as a marker, we identified a subpopulation of periportal hepatocytes located at the limiting plate, which express low amounts of Sox9 and normal amounts of HNF4α, a hepatocyte transcription factor. These cells were termed HybHP, a term fully supported by subsequent transcriptomic and immunohistochemical analyses, which show expression of hepatocyte-specific genes along with a small number of genes that are preferentially expressed in bile duct cells. Using a Sox9-Cre$^{ERT}$ line that is sensitive to low amounts of Sox9 gene transcription, we labeled HybHP and traced their fate under different conditions. HybHP are kept quiescent in the unchallenged liver for at least 9 months after birth, but during chronic liver damage, they proliferate and serve as a source for a large fraction of the new hepatocytes that repopulate the liver. Interestingly, in the two injury models we employed, the manner in which HybHP re-seed the liver appears to be different. In MUP-uPA mice, extensive damage is randomly produced throughout the parenchyma consequent to ER stress (Nakagawa et al., 2014b; Weglarz et al., 2000). In these mice, HybHP clones radiate from the portal area, covering as much volume as possible. Chronic $CCl_4$ administration, on the other hand, results in necrotic damage to pericentral zone 3 hepatocytes. In this case, HybHP clones expand along the portal-central axis, following hepatic chords. These observations suggest that tissue polarity and polarized cell-cell interactions determine the pattern of tissue repair.

Many of the genes that are over-expressed in HybHP relative to conventional hepatocytes are also expressed in bile duct cells and are functionally related to cell adhesion and tubule formation, suggesting that HybHP and bile duct cells may originate from embryonic ductal plate progenitors (Carpentier et al., 2011). Perhaps ductal plate progenitors give rise to mature bile duct cells and HybHP which remain attached to duct cells via homotypic interactions, in clear contrast to parenchymal hepatocytes which originate from hepatoblasts (Miyajima et al., 2014). Interestingly, some of the genes that are underexpressed in HybHP relative to conventional hepatocytes are involved in drug metabolism and immune responses, categories that represent specialized functions of more differentiated hepatocytes that allow them to detoxify xenobiotics and products of the gastrointestinal microbiome that reach the liver via the portal vein. The underexpression of such genes may make HybHP more resistant to toxic insults and inflammatory stress. At this point, however, we do not know whether this specific transcriptomic profile is hardwired or not. Plausibly, it may be maintained by the specific location at which HybHP reside. Indeed, HybHP descendants upregulate certain metabolic genes, such as GS, once they reach the central zone. In normal human liver, a weak signal for Sox9 and Opn can be detected, reminiscent of what was observed in mice, suggesting that HybHP are also present in humans. However, markers that are uniquely expressed in HybHP remain to be identified.

"Hybrid hepatocyte" cell and "HybHP" cell interchangeably refer to a hepatocyte cell that has similar morphology to a conventional hepatocyte cell, and that expresses at least one marker gene that is specific to liver ductal (DC) cells (exemplified by genes in bold italic text in Tables 1 and Table 3), as well as at least one marker gene that is specific to conventional hepatocyte (cHP) cells (exemplified by the genes in text that is neither in bold nor in italics in Table 2) (Also see FIG. 13, and FIG. 5). Data herein show that HybHP cells are present in normal liver (including, for example, liver that does not exhibit symptoms of liver damage. Data herein in FIG. 3B-E show an exemplary system that specifically labels only HybHP. In a particular embodiment, a HybHP cell partially expresses the bile duct gene expression program, can repopulate liver organ and/or liver tissue more efficiently than conventional hepatocytes, can fully transdifferentiate in vitro and in vivo to ductal cell phenotype, can expand indefinitely, and can revert to the hepatocyte phenotype. Unlike conventional hepatocytes, HybHP cells can be cultured in vitro. Further characteristics of HybHP cells are described herein.

Figure 1A:
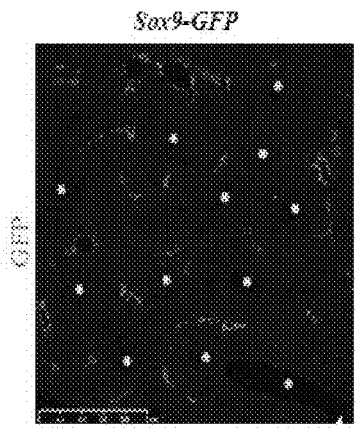
FIG. 1. Periportal hepatocytes express Sox9-GFP and HNF4α. (A-C) Liver sections from 3 months old Sox9-GFP males were analyzed by immunofluorescence (IF) microscopy. (A) A portion of a whole slide scan showing GFP$^+$ cells around portal areas. Asterisks—central veins. Scale bar, 1 mm. (B,C) Liver sections from above mice were stained with DAPI, GFP, CK19 and HNF4α antibodies and imaged. Ductal cells (CK19$^+$, HNF4α$^-$; arrows) show a strong GFP signal. A weaker GFP signal is exhibited by a few periportal CK19$^-$, HNF4α$^+$ hepatocytes (arrowheads). (D) Sox9-Cre$^{ERT}$; R26R$^{YFP}$ 3 months old livers examined for YFP and CK19 and counterstained with DAPI. Spontaneous YFP labeling without tamoxifen treatment is exhibited by few ductal CK19$^+$ cells (arrows). (E) Livers of Sox9-Cre$^{ERT}$; R26R$^{YFP}$ mice treated with tamoxifen (5 mg/kg) were analyzed as above. Ductal CK19$^+$ cells (arrows) and a few periportal hepatocytes (arrowheads) are YFP labeled. (F) The same mice were given 100 mg/kg of tamoxifen and analyzed as above. CK19$^-$, HNF4α$^+$ hepatocytes (arrowheads) are YFP labeled. Bracketed scale bar, 20 µm; open scale bar, 50 (G) 3D reconstruction of dTomato fluorescence in a clarified liver from a tamoxifen treated Sox9-Cre$^{ERT}$; R26R$^{tdTomato}$ mouse (red channel). Ductal cells were stained for CK19 (green channel). Scale bar, 500 µm. (H) 3D reconstruction of a portal tract from (G), in which HybHP that either contact duct cells or are located ≥one cell diameter away are shown. Scale bar, 50 µm.
Figure 1B:
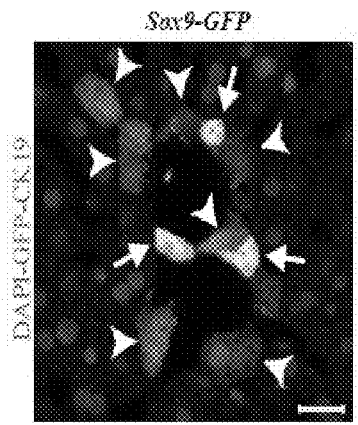
Figure 1C:
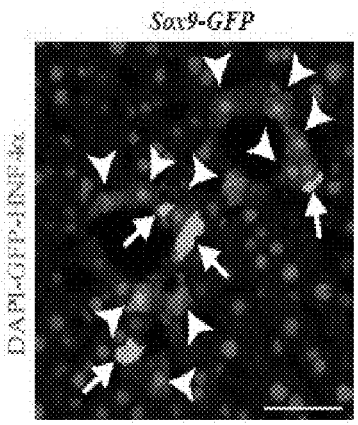
Figure 1D:
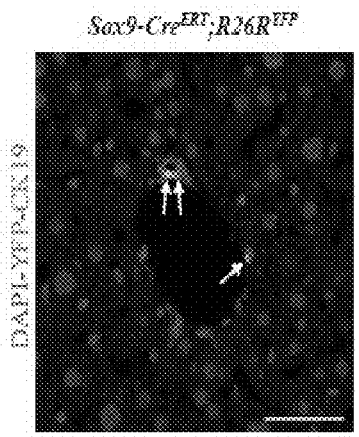
Figure 1E:
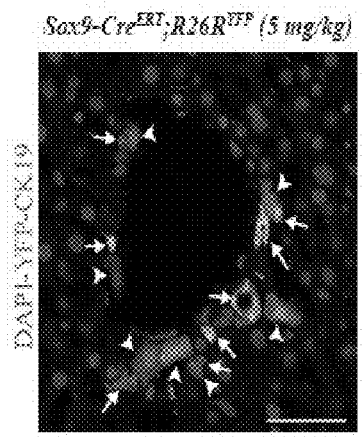
Figure 1F:
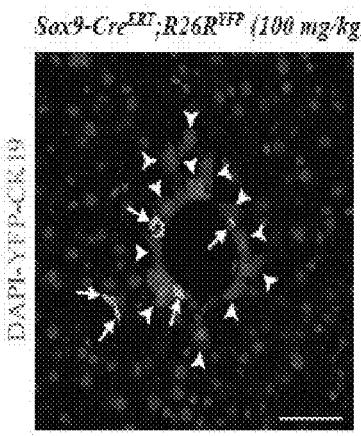
Figure 1G:
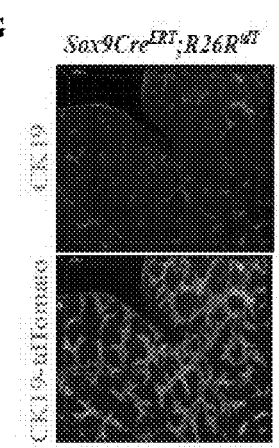
Figure 8A:
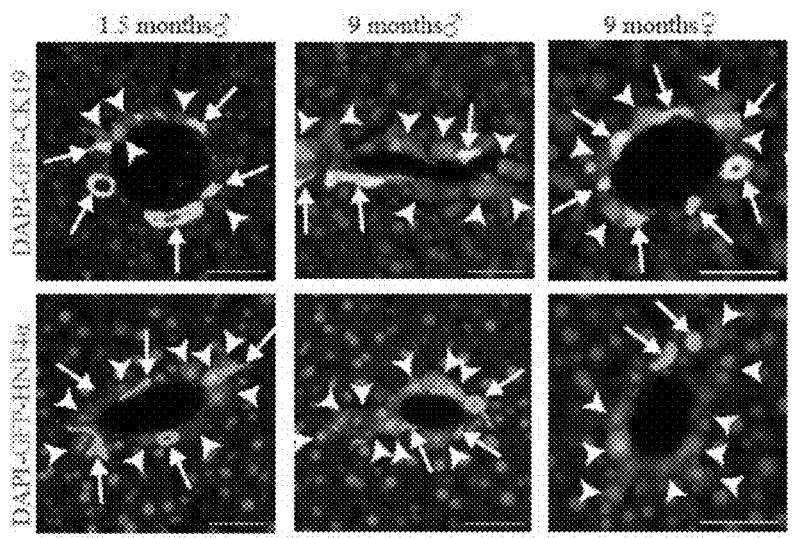
FIG. 8. HybHP are present in both males and females and remain quiescent throughout their lives. Related to FIG. 1. (A) Transgenic Sox9-GFP males and females were analyzed at different ages by IF for GFP, CK19 and HNF4α. (B) Sox9-Cre$^{ERT}$; R26R$^{YFP}$ mice were treated with 100 mg/kg of tamoxifen at P10 and analyzed at 2 and 9 months of age by IF for GFP, CK19 and HNF4α. Scale bar, 50 μm. Arrows—BD; arrowheads—HybHP. (C) Direct visualization of tdTomato fluorescence (red) in DAPI (blue) stained liver sections from a Sox9-Cre$^{ERT}$; R26Rtd$^{Tomato}$ mouse injected with 100 mg/kg and 20 mg/kg tamoxifen, 10 days apart from each other. Arrows: ductal cells; arrowheads: HybHP. (D) Two additional independent portal tracts from the same clarified liver from FIG. 1 G,H.
Figure 8B:
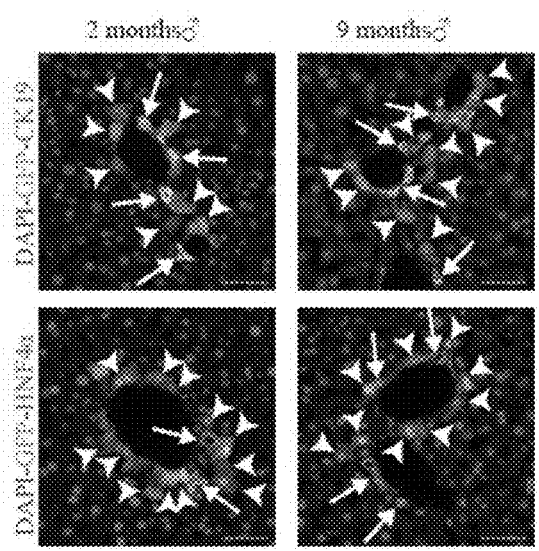
Figure 8C:
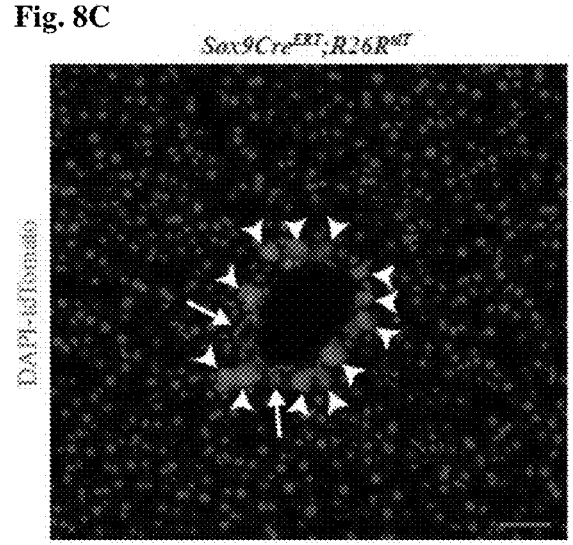
Figure 8D:
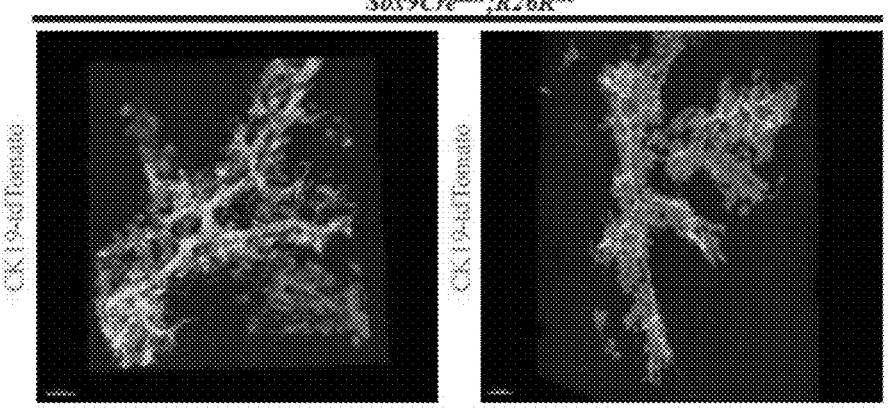

Data herein demonstrate that HybHP cells are located in the liver (including the portal area of the liver) (FIG. 1G,H; FIG. 8D).

Data herein (FIGS. 5E,F and 13C, D) confirm that HybHP are different from conventional hepatocytes not only in their functional behavior but also in their molecular characteristics.

Data herein demonstrate that, in one embodiment, HybHP cells display elevated basal Sox9 promoter activity and other ductal markers.

Data herein demonstrate that, in one embodiment, HybHP cells express markers Sox9 and Opn that are not expressed by conventional hepatocytes.

Data herein demonstrate that, in one embodiment, HybHP express Sox9 and HNF4α (FIG. 1).

Figure 4:
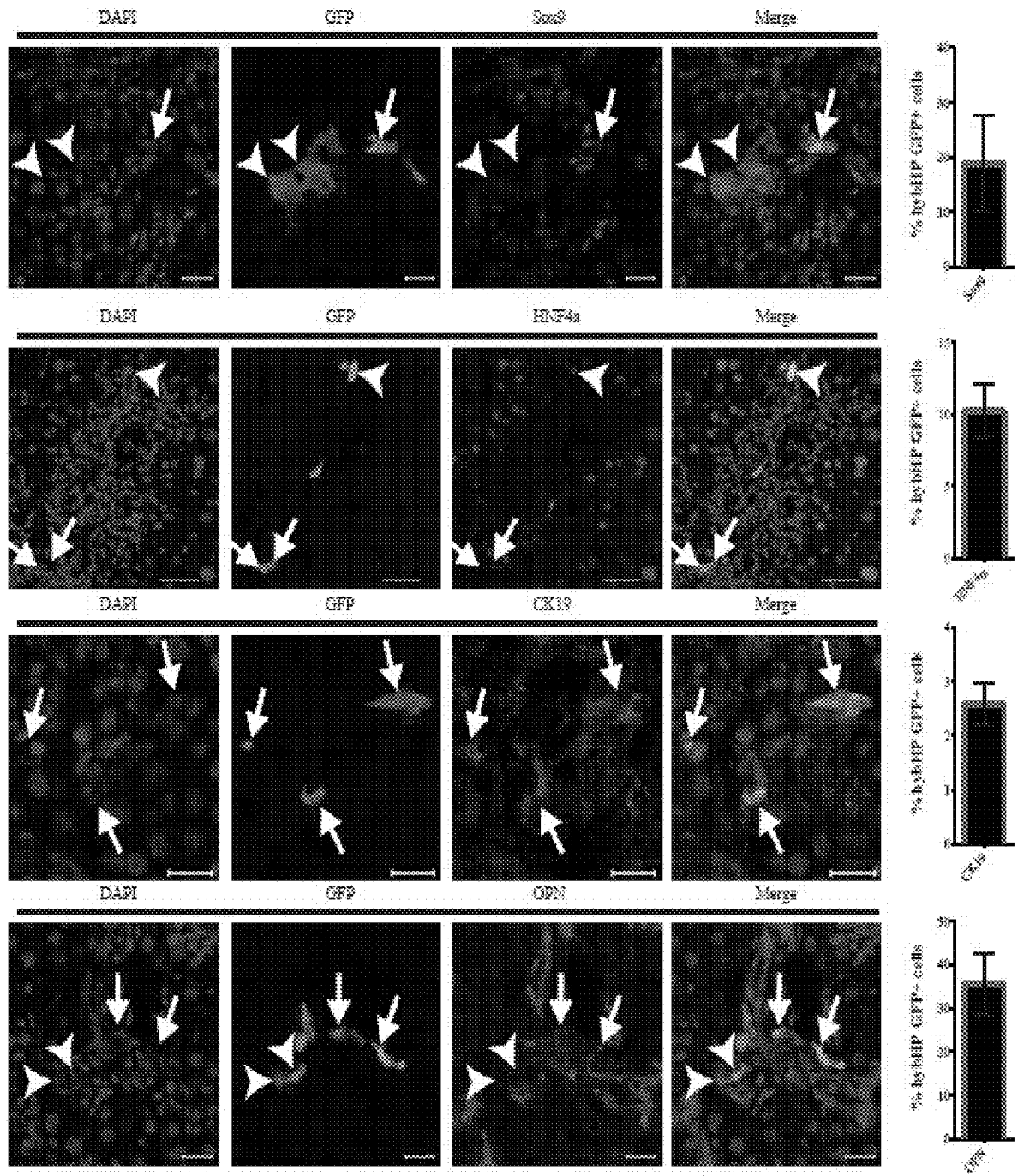
FIG. 4. HybHP can generate ductal cells upon cholestatic injury. Sox9-Cre$^{ERT}$; NZG mice were treated with tamoxifen and injected with Adeno-FLPo as in FIG. 3, and placed on DDC diet 3 weeks later. After 6 weeks, the fate of HybHP was analyzed by co-staining for Opn, Sox9, HNF4α and CK19. Arrows depict HybHP positive for ductal markers (Sox9, Opn and CK19) and negative for the hepatocyte marker HNF4α. Arrowheads denote HybHP negative for ductal markers and positive for HNF4α. Graphs show percentages of GFP$^+$ HybHP positive for CK19 (n=1260), Sox9 (n=513) or Opn (n=994) and negative for HNF4α (n=676). In non-treated mice, no GFP$^+$ HybHP positive for CK19 (n=551), Sox9 (n=232) or negative for HNF4α (n=323) were found. Only 0.72% of GFP$^+$ HybHP were positive for Opn (n=556). Bracketed scale bar, 20 μm; Open scale bar, 50 μm.

Data herein demonstrate that, in one embodiment, FIG. 4 shows HybHP positive for ductal markers (Sox9, Opn and CK19) and negative for the hepatocyte marker HNF4α. FIG. 4 also shows HybHP negative for ductal markers and positive for HNF4α.

Data herein demonstrate that there is not a single marker that is uniquely expressed only by HybHP (FIGS. 5 and 13). Data herein show that HybHP cells express a few ductal-specific genes and numerous hepatocyte-specific genes (FIG. 13 and FIG. 5). Based on their location and transcriptomic pattern, HybHP are either periportal or zone 1 hepatocytes that express a subset of ductal genes (FIG. 13E). Indeed, most class 3 genes share a similar pattern, suggesting that all of them are zone 1 markers (FIG. 13D). Interestingly, class 3 genes are the only ones that do not follow the trend in the analysis of hepatocyte transdifferentiation performed by Tarlow, et al. This observation suggests that class 3 genes are zone 1 hepatocyte genes that are downregulated during the transdifferentiation process and therefore do not define any specific functional property of HybHP. However we have stained human liver paraffin sections for the ductal markers that are weakly expressed by HybHP, such as Sox9 and OPN. We found that some periportal hepatocytes in human paraffin sections also weakly express these markers, suggesting that HybHP could also be present in humans (FIG. 5F).

Data herein demonstrate that, in one embodiment, specific expression of Sox9, Opn, Agxt2l1 and Aqp4 in HybHP by immunostaining (FIG. 5E and FIG. 13C, D) consistent with the differential expression analysis performed. In some embodiments, HybHP cells express lower levels of Sox9, and/or lower levels of Opn, compared to ductal cells (FIGS. 5E, 5F and 13C).

In one embodiment, HybHP cells are negative for the bile duct marker CK19 (FIG. 1B) and positive for the hepatocyte marker HNF4α (FIG. 1C) and comprise approximately 4.53%±0.24% of all hepatocytes.

In one embodiment, expression of TLR5 and TLR8 is downregulated to very low levels in HybHP compared to HP.

In one embodiment, HybHP cells are negative for the bile duct marker CK19.

In one embodiment, HybHP cells are positive for the hepatocyte marker HNF4a.

The observed differences in gene expression between conventional hepatocytes and HybHP cannot be explained by contamination. Data herein also rule out that differences in gene expression could result from contamination of HybHP with bile duct (BD) cells using immunostaining (FIG. 5E and FIG. 13C, D) and statistical analysis.

Data herein demonstrate that HybHP cells multiply in number in vitro under conditions for growth of ductal cells (Example 8) to form organoids. This is unlike cHP cells that do not grow in vitro. Also, HybHP cells can be cultured indefinitely in vitro under growth conditions similar to those for ductal cells.

Data herein also show that HybHP cells transdifferentiate in vivo into ductal cells (including bile duct cells and oval cells) (Example 3, Example 5).

Upon in vivo transplantation of HybHP cells, the transplanted HybHP cells repopulate all liver tissue zones, including zone 1, zone 2, and zone 3 and differentiate and transdifferentiate into progeny hepatocytes and DC cells that express the correct liver zonation cell markers (Example 2, Example 3, Example 5). Data herein demonstrate that the in vitro expanded HybHP cells can be reverted to the hepatocyte phenotype for transplantation, and that HybHP cells expand upon liver injury and form larger and more stably differentiated clones than other hepatocytes (Example 2, Example 3, Example 5).

Data herein show that repopulation of diseased liver by HybHP is more efficient than by Pluripotent Stem Cells (iPSCs) or ductal cells. For example, following in vivo transplantation of 45,000 HybHP cells, the transplanted HybHP cells repopulated 50% of the liver after 3 months (Example 2, Example 3, Example 5, FIG. 6). This surprising degree of liver repopulation contrasts with the prior art's inefficient use of Pluripotent Stem Cells (iPSCs) and ductal cells for repopulating the liver. For example, transplantation of 1 million iPSCs resulted in only a 2% repopulation after 9 months (Zhu et al., Nature (2014) 508(7494):93-7). Similarly, 500,000-800,000 ductal cells reached only 1% of repopulation after 2-3 month and none of the animals survived (Huch et al., Nature (2013) 494(7436):247-50; Huch et al., Cell (2015) 160:299-312).

Data herein also demonstrate that the repopulation, i.e., the contribution of HybHP to new hepatocytes, in the CCl4 chronic injury model is around 65%. This means that starting with 5% of total hepatocytes, after 6 weeks of CCl4 treatment, HybHP expand 13-fold to give rise to 65% of all hepatocytes. At the same time, conventional hepatocytes decline from 95% to 35% of all hepatocytes.

Figure 10A:
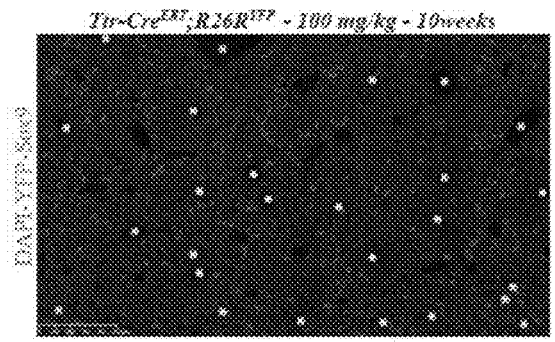
Figure 10B:
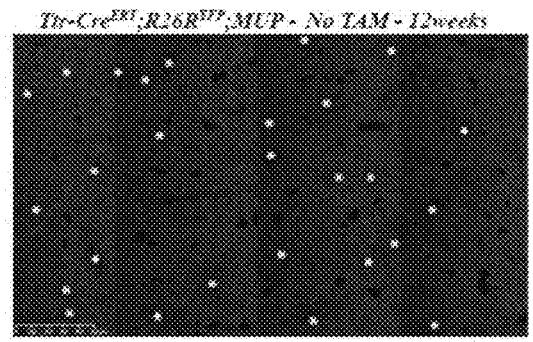
Figure 10C:
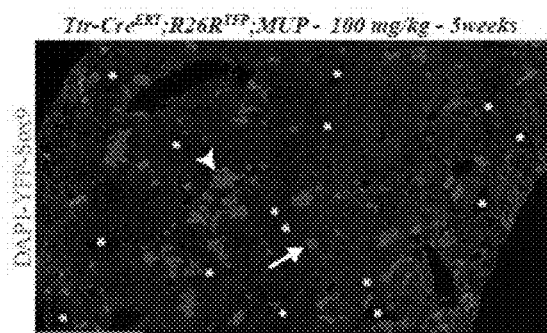
Figure 10D:
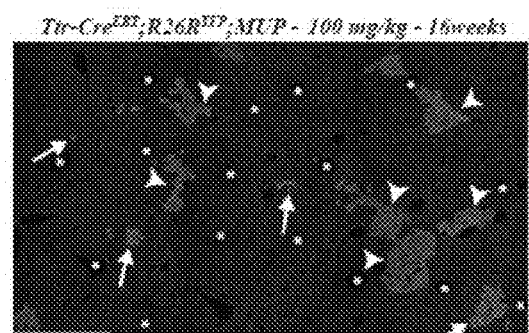
Figure 10E:
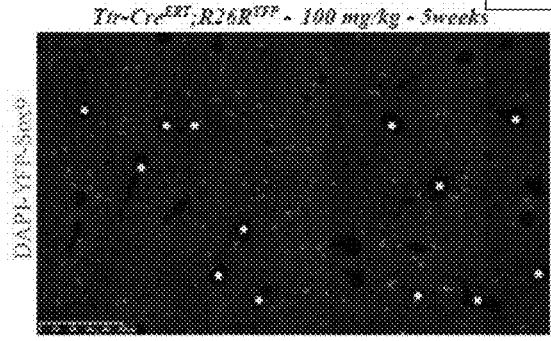
Figure 10F:
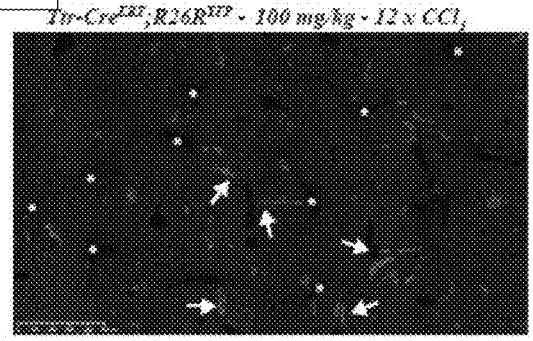

The results clearly show that HybHP expand during the course of repetitive CCl4 injury whereas single or acute doses barely produce any effect on the HybHP population (FIG. 3F,G) as supported by further data herein (FIG. 10E, F FIG. 2D-F).

Figure 6A:
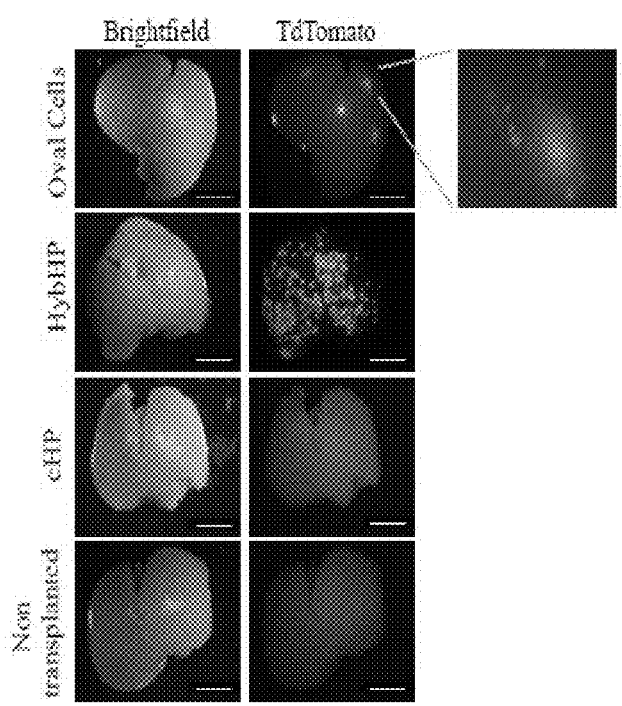
FIG. 6. HybHP exhibit higher repopulation capacity than conventional hepatocytes or oval cells. (A) HybHP and conventional HP were FACS sorted from Sox9-Cre$^{ERT}$; R26R$^{tdTomato}$ mice (8-12 weeks old), and 45,000 cells were transplanted into Fah$^{-/-}$; Rag2$^{-/-}$; Il2rg$^{-/-}$ mice (n=3 for conventional HP and n=2 for HybHP). Oval cells (OC; 45,000) were obtained by FACS sorting from a Sox9-Cre$^{ERT}$; R26R$^{tdTomato}$ mouse fed with CDE diet for 3 weeks and transplanted into 3 Fah$^{-/-}$; Rag2$^{-/-}$; Il2rg$^{-/-}$ mice. Brightfield and tdTomato images of the medial lobes of non-transplanted and HybHP-, HD- and OC-transplanted livers 8 weeks after transplantation. Scale bar 5 mm. (B) Frozen sections of above livers were analyzed by direct fluorescence for tdTomato and IF for FAH expression. OC clones formed by tdTomato$^+$ cells do not exhibit FAH expression. HybHP formed clones of tdTomato$^+$ and FAH$^+$ hepatocytes, whereas conventional HP gave rise to clones of tdTomato$^-$ and FAH$^+$ hepatocytes. (C) Upper graph: clonal area quantification in 3 conventional HP and 2 HybHP transplanted liver. OC clones were not quantified due to their small number and size. **=Unpaired t test with Welch's correction Pv<0.0001. cHP clones, n=500 and HybHP clones, n=695. Every measured clone with the mean and S.D. is shown. Lower graph: areas of all clones in frozen liver sections from (B). **=Unpaired t test with Welch's correction P<0.0001. cHP clones, n=132 and HybHP clones, n=113. Every measured clone with mean and S.D. is shown. (D) Liver sections from HybHP transplanted mice in (B) stained for GS. White arrow: tdTomato$^+$ GS$^+$ HybHP in a HybHP clone without GS expression, surrounded by a damaged parenchyma with diffuse GS expression. Scale bar: 100 μm. (E) Survival curves of an independent cohort of mice transplanted with HybHP (n=4), NH (n=7) or non-transplanted controls (n=9). P values were determined by Log-rank (Mantel-Cox) test. Black polygons over x-axis represent periods while the animals were on NTBC during the on-off NTBC cycles.
Figure 6B:
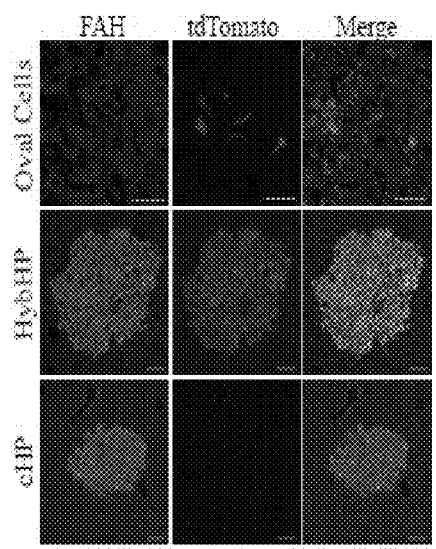
Figure 6C:
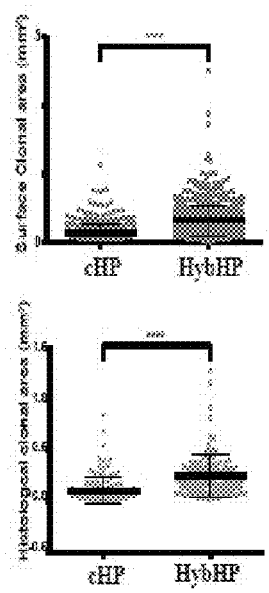
Figure 6D:
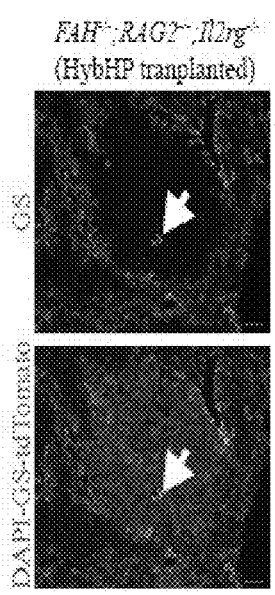
Figure 6E:
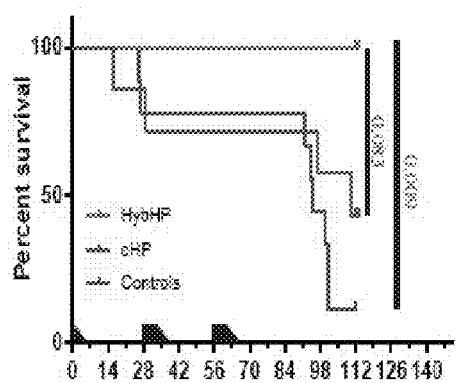

Data herein demonstrate that that HybHP are superior to conventional hepatocytes in repopulating an injured liver (FIG. 6E).

Not only do HybHP cells repopulate liver, but they also treat liver damage. Data herein show that animals suffering from liver damage that are transplanted with HybHP do not die from otherwise terminal liver damage (Example 5). Following transplantation of 14,000-50,000 HybHP cells, much less than the 500,000-1,000,000 cells commonly used in such studies, all HybHP transplanted animals were still alive compared to the death of 90% of control animals and of 50% of cHP-transplanted mice (Example 5; FIG. 6E).

Furthermore, transplanted HybHPs repopulate the liver without giving rise to hepatocellular carcinoma (HCC) (Example 6)].

ii) HybHP Provide a New Framework for Understanding Liver Regeneration

Liver regeneration has been most extensively studied in the context of partial ($\frac{2}{3}^{rd}$) hepatectomy, in which all liver cells undergo limited rounds of cell division to restore organ mass. However, controversy had dominated studies of liver homeostasis and regeneration after injury giving rise to contrasting hypotheses such as the streaming liver hypothesis (Fellous et al., 2009; Furuyama et al., 2010), the liver stem cell hypothesis (Dorrell et al., 2011), and more recent findings that question the ability of oval cells to give rise to hepatocytes (Español-Suñer et al., 2012; Malato et al., 2011; Rodrigo-Torres et al., 2014; Schaub et al., 2014; Tarlow et al., 2014a; Yanger et al., 2014) and suggest that hepatocytes can transdifferentiate into oval cells (Michalopoulos et al., 2005; Sekiya and Suzuki, 2014; Tanimizu et al., 2014; Tarlow et al., 2014b; Yanger et al., 2013). However, it was also shown that cultured bile duct cells can transdifferentiate into hepatocytes (Huch et al., 2013; Huch et al., 2015). The discovery of HybHP allows us to propose a model of liver regeneration that reaffirms the fundamental role of the portal-central axis in liver physiology, with the portal tract being the organizing center and source of cells responsible for the majority of parenchymal regeneration. We suggest that HybHP are mainly activated under conditions when the damaged parenchyma is more efficiently repopulated by hepatocytes that originate from the limiting plate. When the damage is mild and scattered, it may be more efficient to restore lost cells by a simple division of neighboring hepatocytes. But when many hepatocytes are continuously destroyed, the highly complex network of hepatic sinusoids and bile canaliculi is compromised, and the most effective way to properly regenerate the liver is to induce expansion of hepatocytes that are already connected to bile duct cells from the portal tract outwards, a task that can be most easily fulfilled by HybHP.

Despite their expansion in MUP-uPA mice, oval cells are incapable of differentiating into hepatocytes. Notably, oval cell expansion is mainly detected in areas where MUP-uPA mice have lost HybHP and a similar pattern was detected in the STAM liver and in mice fed with CDE diet. These observations suggest that the oval cell response is activated when HybHP fail to expand. Nonetheless, since oval cells do not give rise to differentiated hepatocytes the logic underlying their expansion remains enigmatic. One possible function for oval cells could be restoration of the bile canaliculi network and liver polarity. Supporting these lines, inking the ductal tree has allowed visualization of its structure in different models of liver injury with oval cell expansion (Kaneko et al., 2015). Such studies show that oval cells are connected, representing extensions of the preexisting ductal tree, further challenging the old view according to which oval cells are liver progenitor cells that seed the parenchyma to generate new hepatocytes. More likely, oval cells participate in remodeling of the ductal tree, rather than functioning as bipotential stem cells, at least in mice (Schaub et al., 2014; Tarlow et al., 2014a; Yanger et al., 2014).

Data herein demonstrate the use of genetic lineage tracing to identify cells responsible for liver repair following injury and then queried their roles in three distinct HCC models. Data herein teaches the discovery of HybHP cells, a new cell type that is a hybrid between a hepatocyte and a duct cell. Data herein show that the unique HybHP cells are low Sox9 expressing, periportal hepatocytes that also express other bile duct enriched genes (hence Hybrid Hepatocytes) and are the primary cells that mediate liver injury repair. Surprisingly, despite their high regenerative potential and multiple division cycles after tumor promoting injuries, data herein show that HybHP cells are not the preferred origin for HCC. Thus, the invention demonstrates that the inventors' newly discovered HybHP cells represent a unique mechanism for tissue repair that avoids excessive tumorigenesis by using a specialized set of differentiated cells rather than adult stem cells. The invention's cells can be used to treat liver injury and/or disease via transplantation.

Thus, in one embodiment, the invention provides a purified mammalian HybHP cell, and/or purified population of mammalian HybHP cells, that expresses at least one first protein marker of liver ductal (DC) cells, and express at least one second protein marker of conventional hepatocyte (cHP) cells.

The invention also provides a purified mammalian first antibody-HybHP cell conjugate wherein the first antibody specifically binds to a first protein marker of liver ductal (DC) cells. Also provided by the invention is a composition comprising the purified first antibody-HybHP cell conjugate.

The invention further provides a purified mammalian first antibody-HybHP cell-second antibody conjugate, wherein said first antibody specifically binds to a first protein marker of liver ductal (DC) cells, and wherein said second antibody specifically binds to a second protein marker of conventional hepatocyte (cHP) cells. Also provided by the invention is a composition comprising the purified first antibody-HybHP cell-second antibody conjugate.

The invention further provides a mammalian first antibody-HybHP cell-second antibody conjugate isolated by any of the methods described herein. The invention additionally provides a composition comprising the mammalian first antibody-HybHP cell-second antibody conjugate isolated by any of the methods described herein.

B) Methods for Isolating HybHP Cells

The invention also provides methods to propagate the newly discovered HybHP cells ex vivo. In a first approach, purifying a hepatocyte (HybHP) cell (and/or a population of hepatocyte (HybHP) cells) from a mammalian liver, comprises a) preparing a single-cell suspension from the liver (e.g., by collagenase digestion of liver tissue (Example 1)), b) combining the single-cell suspension with i) at least one first antibody that specifically binds to a first protein marker of liver ductal (DC) cells, and ii) at least one second antibody that specifically binds to a second protein marker of conventional hepatocyte (cHP) cells, wherein the combining is under conditions for specific binding of the at least one first antibody to the first protein marker and of the at least one second antibody to the second protein, and wherein the specific binding produces a first composition that comprises a first antibody-HybHP cell-second antibody conjugate, and c) isolating the first antibody-HybHP cell-second antibody conjugate from the single-cell suspension, thereby producing a second composition that comprises a purified HybHP cell, and/or a purified population of HybHP cell.

In one embodiment, the "isolating" step may be achieved using a second antibody that specifically binds to the one or both of the first antibody-second antibody.

In one embodiment, the first protein marker of liver ductal (DC) cells is encoded by one or more gene shown in bold italic text in Table 1 and Table 3.

TABLE 1

HybHP marker genes that are upregulated in HybHP compared to cHP. Bold italics text (numbered 1-193 in the first column) reflect genes that are also expressed in ductal cells.

| | Mouse gene name | Mouse Entrez gene ID | Human Entrez gene ID |
|---|---|---|---|
| 1 | *1700011H14Rik* | 67082 | #N/A |
| 2 | *1810064F22Rik* | 69862 | #N/A |
| 3 | *4930452B06Rik* | 74430 | #N/A |
| 4 | *5330417C22Rik* | 229722 | #N/A |
| 5 | *5930403L14Rik* | 320939 | #N/A |
| 6 | *8430419L09Rik* | 74525 | #N/A |
| 7 | *A230001M10Rik* | 319951 | #N/A |
| 8 | *Abcc5* | 27416 | 10057 |
| 9 | *Abhd2* | 54608 | 11057 |
| 10 | *Adamts5* | 632263 | 11096 |
| 11 | *Adamts5* | 23794 | 11096 |
| 12 | *Aifl1* | 108897 | 83543 |
| 13 | *Ankrd1* | 107765 | 27063 |
| 14 | *Ankrd9* | 74251 | 122416 |
| 15 | *Ano1* | 101772 | 55107 |
| 16 | *Anxa13* | 69787 | 312 |
| 17 | *Apobec3* | 80287 | #N/A |
| 18 | *App* | 11820 | 351 |
| 19 | *Arhgap6* | 11856 | 395 |
| 20 | *Arhgef16* | 230972 | 27237 |
| 21 | *Atp1b1* | 11931 | 481 |
| 22 | *B4galt5* | 56336 | 9334 |
| 23 | *Bcam* | 57278 | 4059 |
| 24 | *Bicc1* | 83675 | 80114 |
| 25 | *Bmyc* | 107771 | #N/A |
| 26 | *Ccdc120* | 54648 | 90060 |
| 27 | *Ccdc68* | 381175 | 80323 |
| 28 | *Ccdc88c* | 68339 | 440193 |
| 29 | *Cd200* | 100048780 | 4345 |
| 30 | *Cd200* | 17470 | 4345 |
| 31 | *Cd24a* | 12484 | #N/A |
| 32 | *Cd63* | 12512 | 967 |
| 33 | *Cdh1* | 12550 | 999 |
| 34 | *Celsr1* | 12614 | 9620 |
| 35 | *Chrm3* | 12671 | 1131 |
| 36 | *Chrnb1* | 11443 | 1140 |
| 37 | *Cldn6* | 54419 | 284620 |
| 38 | *Cldn7* | 53624 | 1366 |
| 39 | *Col8a1* | 12837 | 1295 |
| 40 | *Creb3l1* | 26427 | 90993 |
| 41 | *Cttnbp2* | 30785 | 83992 |
| 42 | *Dab1* | 13131 | 1600 |
| 43 | *Dcdc2a* | 195208 | #N/A |
| 44 | Dcx | 13193 | 1641 |
| 45 | *Ddit4l* | 73284 | 115265 |
| 46 | *Ddr1* | 12305 | 780 |
| 47 | *Dpysl4* | 26757 | 10570 |
| 48 | Edn1 | 13614 | 1906 |
| 49 | Ednrb | 13618 | 1910 |
| 50 | *Egflam* | 268780 | 133584 |
| 51 | *Ehd2* | 259300 | 30846 |
| 52 | *Ehf* | 13661 | 26298 |
| 53 | Eln | 13717 | 2006 |
| 54 | Emb | 13723 | 133418 |
| 55 | *Emp1* | 13730 | 2012 |
| 56 | Enah | 13800 | 55740 |
| 57 | *Epb4.1l1* | 13821 | #N/A |
| 58 | Epb4.1l4a | 13824 | #N/A |

TABLE 1-continued

HybHP marker genes that are upregulated in HybHP compared to cHP. Bold italics text (numbered 1-193 in the first column) reflect genes that are also expressed in ductal cells.

| | Mouse gene name | Mouse Entrez gene ID | Human Entrez gene ID |
|---|---|---|---|
| 59 | *Epcam* | 17075 | 4072 |
| 60 | *Epha4* | 13838 | 2043 |
| 61 | *Espn* | 56226 | 83715 |
| 62 | *Etv4* | 18612 | 2118 |
| 63 | *Evc* | 59056 | 2121 |
| 64 | *Evc2* | 68525 | 132884 |
| 65 | *F2rl1* | 14063 | 2150 |
| 66 | *Fam13c* | 71721 | 220965 |
| 67 | *Fam198a* | 245050 | 729085 |
| 68 | *Fam198b* | 68659 | 51313 |
| 69 | *Fam81a* | 76886 | 145773 |
| 70 | *Fam83a* | 239463 | 84985 |
| 71 | *Fbln2* | 14115 | 2199 |
| 72 | *Fermt1* | 241639 | 55612 |
| 73 | *Fgfr1* | 14182 | 2260 |
| 74 | *Fgfr2* | 14183 | 2263 |
| 75 | *Flrt2* | 399558 | 23768 |
| 76 | *Foxj1* | 15223 | 2302 |
| 77 | *Frem2* | 242022 | 341640 |
| 78 | *Fstl3* | 83554 | 10272 |
| 79 | *Gcnt1* | 14537 | 2650 |
| 80 | *Gcnt1* | 635912 | 2650 |
| 81 | *Gja5* | 14613 | 2702 |
| 82 | *Glis3* | 226075 | 169792 |
| 83 | *Gm609* | 208166 | #N/A |
| 84 | *Gnb5* | 14697 | 10681 |
| 85 | *Gpm6a* | 234267 | 2823 |
| 86 | *Gpr126* | 215798 | 57211 |
| 87 | *Gprc5a* | 232431 | 9052 |
| 88 | *Gprc5b* | 64297 | 51704 |
| 89 | *Hbb-bh1* | 15131 | #N/A |
| 90 | *Hbb-bh1* | 15132 | #N/A |
| 91 | *Hbb-bh1* | 100044263 | #N/A |
| 92 | *Higd1c* | 380975 | 613227 |
| 93 | *Higd1c* | 393082 | 613227 |
| 94 | *Higd1c* | 554292 | 613227 |
| 95 | *Hkdc1* | 216019 | 80201 |
| 96 | *Hmcn1* | 545370 | 83872 |
| 97 | *Igf2bp2* | 319765 | 10644 |
| 98 | *Igf2bp7* | 29817 | 3490 |
| 99 | *Il17rb* | 50905 | 55540 |
| 100 | *Il17re* | 57890 | 132014 |
| 101 | *Ildr1* | 106347 | 286676 |
| 102 | *Isg20* | 57444 | 3669 |
| 103 | *Itga6* | 16403 | 3655 |
| 104 | *Itgb8* | 320910 | 3696 |
| 105 | *Jam2* | 67374 | 58494 |
| 106 | *Kcne3* | 100044693 | 10008 |
| 107 | *Kcne3* | 57442 | 10008 |
| 108 | *Kcnk1* | 16525 | 3775 |
| 109 | *Kcnma1* | 16531 | 3778 |
| 110 | *Kif1a* | 16560 | 547 |
| 111 | *Kifc3* | 16582 | 3801 |
| 112 | *Krt19* | 16669 | 3880 |
| 113 | *Krt7* | 110310 | 3855 |
| 114 | *Lama5* | 16776 | 3911 |
| 115 | *Lamb2* | 16779 | 3913 |
| 116 | *Lamc2* | 16782 | 3918 |
| 117 | *Lamc3* | 23928 | 10319 |
| 118 | *Ldb2* | 16826 | 9079 |
| 119 | *Lrrc4* | 192198 | 64101 |
| 120 | *Lrrn1* | 16979 | 57633 |
| 121 | *Mal* | 17153 | 4118 |
| 122 | *Mapk13* | 26415 | 5603 |
| 123 | *Mapk8ip1* | 19099 | 9479 |
| 124 | *Marveld3* | 73608 | 91862 |
| 125 | *Mecom* | 14013 | 2122 |
| 126 | *Megf6* | 230971 | 1953 |
| 127 | *Mfge8* | 17304 | 4240 |
| 128 | *Mfi2* | 30060 | 4241 |
| 129 | *Myo5c* | 208943 | 55930 |
| 130 | *Nck2* | 100044475 | 8440 |
| 131 | *Nck2* | 621446 | 8440 |

TABLE 1-continued

HybHP marker genes that are upregulated in HybHP compared to cHP. Bold italics text (numbered 1-193 in the first column) reflect genes that are also expressed in ductal cells.

| | Mouse gene name | Mouse Entrez gene ID | Human Entrez gene ID |
|---|---|---|---|
| 132 | *Nck2* | 17974 | 8440 |
| 133 | *Ngf* | 18049 | 4803 |
| 134 | *Nipal2* | 223473 | 79815 |
| 135 | *Nrarp* | 67122 | 441478 |
| 136 | *Ntrk2* | 18212 | 4915 |
| 137 | *Olfm2* | 244723 | 93145 |
| 138 | *Osbpl5* | 79196 | 114879 |
| 139 | *Pak6* | 214230 | 56924 |
| 140 | *Pamr1* | 210622 | 25891 |
| 141 | *Pcyt1b* | 236899 | 9468 |
| 142 | *Pdgfd* | 71785 | 80310 |
| 143 | *Peg10* | 170676 | 23089 |
| 144 | *Pfkp* | 56421 | 5214 |
| 145 | *Pkia* | 18767 | 5569 |
| 146 | *Ppl* | 19041 | 5493 |
| 147 | *Prdm16* | 70673 | 63976 |
| 148 | *Prelp* | 116847 | 5549 |
| 149 | *Prom1* | 19126 | 8842 |
| 150 | *Prr15l* | 217138 | 79170 |
| 151 | *Ptpn13* | 19249 | 5783 |
| 152 | *Ptpn14* | 19250 | 5784 |
| 153 | *Rab27b* | 80718 | 5874 |
| 154 | *Rasal1* | 19415 | 8437 |
| 155 | *Rassf9* | 237504 | 9182 |
| 156 | *Reck* | 631094 | 8434 |
| 157 | *Reck* | 53614 | 8434 |
| 158 | *Rgma* | 244058 | 56963 |
| 159 | *Rtn4* | 68585 | 57142 |
| 160 | *Sall2* | 50524 | 6297 |
| 161 | *Scara3* | 219151 | 51435 |
| 162 | *Scd2* | 20250 | #N/A |
| 163 | *Scn2a1* | 110876 | #N/A |
| 164 | *Sema3c* | 20348 | 10512 |
| 165 | *Sema5a* | 20356 | 9037 |
| 166 | *Setd7* | 73251 | 80854 |
| 167 | *Shroom3* | 27428 | 57619 |
| 168 | *Slc12a8* | 171286 | 84561 |
| 169 | *Slc4a3* | 20536 | 6508 |
| 170 | *Slc5a1* | 20537 | 6523 |
| 171 | *Smpd3* | 58994 | 55512 |
| 172 | *Smpdl3b* | 100340 | 27293 |
| 173 | *Sox4* | 20677 | 6659 |
| 174 | *Sox4* | 20673 | 6659 |
| 175 | *Sox9* | 20682 | 6662 |
| 176 | *Spint1* | 20732 | 6692 |
| 177 | *Spp1* | 20750 | 6696 |
| 178 | *Src* | 20779 | 6714 |
| 179 | *Sstr2* | 20606 | 6752 |
| 180 | *St14* | 19143 | 6768 |
| 181 | *Stambpl1* | 76630 | 57559 |
| 182 | *Stat4* | 20849 | 6775 |
| 183 | *Steap2* | 74051 | 261729 |
| 184 | *Tgfb2* | 21808 | 7042 |
| 185 | *Timp3* | 21859 | 7078 |
| 186 | *Tm4sf4* | 229302 | 7104 |
| 187 | *Tmem229a* | 319832 | 730130 |
| 188 | *Tmem45a* | 56277 | 55076 |
| 189 | *Tspan8* | 216350 | 7103 |
| 190 | *Tstd1* | 226654 | 100131187 |
| 191 | *Vwf* | 22371 | 7450 |
| 192 | *Wnt4* | 22417 | 54361 |
| 193 | *Zfp248* | 72720 | #N/A |
| 194 | Aim1l | 230806 | 55057 |
| 195 | Aldh1b1 | 72535 | 219 |
| 196 | Apoa4 | 11808 | 337 |
| 197 | Apoc2 | 11813 | 344 |
| 198 | Aqp4 | 11829 | 361 |
| 199 | Arhgap10 | 78514 | 79658 |
| 200 | Atp4a | 11944 | 495 |
| 201 | Bdh2 | 69772 | 56898 |
| 202 | Cbs | 12411 | 875 |
| 203 | Cib3 | 234421 | 117286 |
| 204 | Clic5 | 224796 | 53405 |
| 205 | Cryl1 | 68631 | 51084 |
| 206 | Ctnnbip1 | 67087 | 56998 |
| 207 | Ctsc | 13032 | 1075 |
| 208 | Cyp2f2 | 13107 | #N/A |
| 209 | Defb1 | 13214 | 1672 |
| 210 | Efna3 | 100046031 | 1944 |
| 211 | Efna3 | 13638 | 1944 |
| 212 | Fbp1 | 14121 | 2203 |
| 213 | Gas2 | 14453 | 2620 |
| 214 | Gldc | 104174 | 2731 |
| 215 | Gls2 | 216456 | 27165 |
| 216 | Gucy2c | 14917 | 2984 |
| 217 | Hal | 15109 | 3034 |
| 218 | Hsbp1l1 | 66255 | 440498 |
| 219 | Hsd17b13 | 243168 | 345275 |
| 220 | Hsd17b6 | 27400 | 8630 |
| 221 | Kcp | 333088 | 375616 |
| 223 | Mrgpre | 244228 | 116534 |
| 224 | Ncam2 | 17968 | 4685 |
| 225 | Olfm3 | 229759 | 118427 |
| 226 | Osbp2 | 100044882 | 23762 |
| 227 | Osbp2 | 74309 | 23762 |
| 228 | Plxna2 | 18845 | 5362 |
| 229 | Ptgds | 19215 | 5730 |
| 230 | Ptges | 64292 | 9536 |
| 231 | Sdsl | 257635 | 113675 |
| 232 | Serpina12 | 68054 | 145264 |
| 233 | Sulf2 | 72043 | 55959 |
| 234 | Tbc1d30 | 74694 | 23329 |
| 235 | Tmprss4 | 214523 | 56649 |
| 236 | Ugt2b38 | 100559 | #N/A |
| 237 | Xirp1 | 22437 | 165904 |
| 238 | From | Mouse | Human |
| 239 | 1700011H14Rik | 67082 | #N/A |
| 240 | 1810064F22Rik | 69862 | #N/A |
| 241 | 4930452B06Rik | 74430 | #N/A |
| 242 | 5330417C22Rik | 229722 | #N/A |
| 243 | 5930403L14Rik | 320939 | #N/A |
| 244 | 8430419L09Rik | 74525 | #N/A |
| 245 | A230001M10Rik | 319951 | #N/A |
| 246 | Abcc5 | 27416 | 10057 |
| 247 | Abhd2 | 54608 | 11057 |
| 248 | Adamts5 | 632263 | 11096 |
| 249 | Adamts5 | 23794 | 11096 |
| 250 | Aifl1 | 108897 | 83543 |
| 251 | Ankrd1 | 107765 | 27063 |
| 252 | Ankrd9 | 74251 | 122416 |
| 253 | Ano1 | 101772 | 55107 |
| 254 | Anxa13 | 69787 | 312 |
| 255 | Apobec3 | 80287 | #N/A |
| 256 | App | 11820 | 351 |
| 257 | Arhgap6 | 11856 | 395 |
| 258 | Arhgef16 | 230972 | 27237 |
| 259 | Atp1b1 | 11931 | 481 |
| 260 | B4galt5 | 56336 | 9334 |
| 261 | Bcam | 57278 | 4059 |
| 262 | Bicc1 | 83675 | 80114 |
| 263 | Bmyc | 107771 | #N/A |
| 264 | Ccdc120 | 54648 | 90060 |
| 265 | Ccdc68 | 381175 | 80323 |
| 266 | Ccdc88c | 68339 | 440193 |
| 267 | Cd200 | 100048780 | 4345 |
| 268 | Cd200 | 17470 | 4345 |
| 269 | Cd24a | 12484 | #N/A |
| 270 | Cd63 | 12512 | 967 |
| 271 | Cdh1 | 12550 | 999 |
| 272 | Celsr1 | 12614 | 9620 |
| 273 | Chrm3 | 12671 | 1131 |
| 274 | Chrnb1 | 11443 | 1140 |
| 275 | Cldn6 | 54419 | 284620 |
| 276 | Cldn7 | 53624 | 1366 |
| 277 | Col8a1 | 12837 | 1295 |
| 278 | Creb3l1 | 26427 | 90993 |

TABLE 1-continued

HybHP marker genes that are upregulated in HybHP compared to cHP. Bold italics text (numbered 1-193 in the first column) reflect genes that are also expressed in ductal cells.

| | Mouse gene name | Mouse Entrez gene ID | Human Entrez gene ID |
|---|---|---|---|
| 279 | Cttnbp2 | 30785 | 83992 |
| 280 | Dab1 | 13131 | 1600 |
| 281 | Dcdc2a | 195208 | #N/A |
| 282 | Dcx | 13193 | 1641 |
| 283 | Ddit4l | 73284 | 115265 |
| 284 | Ddr1 | 12305 | 780 |
| 285 | Dpysl4 | 26757 | 10570 |
| 286 | Edn1 | 13614 | 1906 |
| 287 | Ednrb | 13618 | 1910 |
| 288 | Egflam | 268780 | 133584 |
| 289 | Ehd2 | 259300 | 30846 |
| 290 | Ehf | 13661 | 26298 |
| 291 | Eln | 13717 | 2006 |
| 292 | Emb | 13723 | 133418 |
| 293 | Emp1 | 13730 | 2012 |
| 294 | Enah | 13800 | 55740 |
| 295 | Epb4.1l1 | 13821 | #N/A |
| 296 | Epb4.1l4a | 13824 | #N/A |
| 297 | Epcam | 17075 | 4072 |
| 298 | Epha4 | 13838 | 2043 |
| 299 | Espn | 56226 | 83715 |
| 300 | Etv4 | 18612 | 2118 |
| 301 | Evc | 59056 | 2121 |
| 302 | Evc2 | 68525 | 132884 |
| 303 | F2rl1 | 14063 | 2150 |
| 304 | Fam13c | 71721 | 220965 |
| 305 | Fam198a | 245050 | 729085 |
| 306 | Fam198b | 68659 | 51313 |
| 307 | Fam81a | 76886 | 145773 |
| 308 | Fam83a | 239463 | 84985 |
| 309 | Fbln2 | 14115 | 2199 |
| 310 | Fermt1 | 241639 | 55612 |
| 311 | Fgfr1 | 14182 | 2260 |
| 312 | Fgfr2 | 14183 | 2263 |
| 313 | Flrt2 | 399558 | 23768 |
| 314 | Foxj1 | 15223 | 2302 |
| 315 | Frem2 | 242022 | 341640 |
| 316 | Fstl3 | 83554 | 10272 |
| 317 | Gcnt1 | 14537 | 2650 |
| 318 | Gcnt1 | 635918 | 2650 |
| 319 | Gja5 | 14613 | 2702 |
| 320 | Glis3 | 226075 | 169792 |
| 321 | Gm609 | 208166 | #N/A |
| 322 | Gnb5 | 14697 | 10681 |
| 323 | Gpm6a | 234267 | 2823 |
| 324 | Gpr126 | 215798 | 57211 |
| 325 | Gprc5a | 232431 | 9052 |
| 326 | Gprc5b | 64297 | 51704 |
| 327 | Hbb-bh1 | 15131 | #N/A |
| 328 | Hbb-bh1 | 15132 | #N/A |
| 329 | Hbb-bh1 | 100044263 | #N/A |
| 330 | Higd1c | 380975 | 613227 |
| 331 | Higd1c | 393082 | 613227 |
| 332 | Higd1c | 554292 | 613227 |
| 333 | Hkdc1 | 216019 | 80201 |
| 334 | Hmcn1 | 545370 | 83872 |
| 335 | Igf2bp2 | 319765 | 10644 |
| 336 | Igfbp7 | 29817 | 3490 |
| 337 | Il17rb | 50905 | 55540 |
| 338 | Il17re | 57890 | 132014 |
| 339 | Ildr1 | 106347 | 286676 |
| 340 | Isg20 | 57444 | 3669 |
| 341 | Itga6 | 16403 | 3655 |
| 342 | Itgb8 | 320910 | 3696 |
| 343 | Jam2 | 67374 | 58494 |
| 344 | Kcne3 | 100044693 | 10008 |
| 345 | Kcne3 | 57442 | 10008 |
| 346 | Kcnk1 | 16525 | 3775 |
| 347 | Kcnma1 | 16531 | 3778 |
| 348 | Kif1a | 16560 | 547 |
| 349 | Kifc3 | 16582 | 3801 |
| 350 | Krt19 | 16669 | 3880 |
| 351 | Krt7 | 110310 | 3855 |
| 352 | Lama5 | 16776 | 3911 |
| 353 | Lamb2 | 16779 | 3913 |
| 354 | Lamc2 | 16782 | 3918 |
| 355 | Lamc3 | 23928 | 10319 |
| 356 | Ldb2 | 16826 | 9079 |
| 357 | Lrrc4 | 192198 | 64101 |
| 358 | Lrrn1 | 16979 | 57633 |
| 359 | Mal | 17153 | 4118 |
| 360 | Mapk13 | 26415 | 5603 |
| 361 | Mapk8ip1 | 19099 | 9479 |
| 362 | Marveld3 | 73608 | 91862 |
| 363 | Mecom | 14013 | 2122 |
| 364 | Megf6 | 230971 | 1953 |
| 365 | Mfge8 | 17304 | 4240 |
| 366 | Mfi2 | 30060 | 4241 |
| 367 | Myo5c | 208943 | 55930 |
| 368 | Nck2 | 100044475 | 8440 |
| 369 | Nck2 | 621446 | 8440 |
| 370 | Nck2 | 17974 | 8440 |
| 371 | Ngf | 18049 | 4803 |
| 372 | Nipal2 | 223473 | 79815 |
| 373 | Nrarp | 67122 | 441478 |
| 374 | Ntrk2 | 18212 | 4915 |
| 375 | Olfm2 | 244723 | 93145 |
| 376 | Osbpl5 | 79196 | 114879 |
| 377 | Pak6 | 214230 | 56924 |
| 378 | Pamr1 | 210622 | 25891 |
| 379 | Pcyt1b | 236899 | 9468 |
| 380 | Pdgfd | 71785 | 80310 |
| 381 | Peg10 | 170676 | 23089 |
| 382 | Pfkp | 56421 | 5214 |
| 383 | Pkia | 18767 | 5569 |
| 384 | Ppl | 19041 | 5493 |
| 385 | Prdm16 | 70673 | 63976 |
| 386 | Prelp | 116847 | 5549 |
| 387 | Prom1 | 19126 | 8842 |
| 388 | Prr15l | 217138 | 79170 |
| 389 | Ptpn13 | 19249 | 5783 |
| 390 | Ptpn14 | 19250 | 5784 |
| 391 | Rab27b | 80718 | 5874 |
| 392 | Rasal1 | 19415 | 8437 |
| 393 | Rassf9 | 237504 | 9182 |
| 394 | Reck | 631094 | 8434 |
| 395 | Reck | 53614 | 8434 |
| 396 | Rgma | 244058 | 56963 |
| 397 | Rtn4 | 68585 | 57142 |
| 398 | Sall2 | 50524 | 6297 |
| 399 | Scara3 | 219151 | 51435 |
| 400 | Scd2 | 20250 | #N/A |
| 401 | Scn2a1 | 110876 | #N/A |
| 402 | Sema3c | 20348 | 10512 |
| 403 | Sema5a | 20356 | 9037 |
| 404 | Setd7 | 73251 | 80854 |
| 405 | Shroom3 | 27428 | 57619 |
| 406 | Slc12a8 | 171286 | 84561 |
| 407 | Slc4a3 | 20536 | 6508 |
| 408 | Slc5a1 | 20537 | 6523 |
| 409 | Smpd3 | 58994 | 55512 |
| 410 | Smpdl3b | 100340 | 27293 |
| 411 | Sox4 | 20677 | 6659 |
| 412 | Sox4 | 20673 | 6659 |
| 413 | Sox9 | 20682 | 6662 |
| 414 | Spint1 | 20732 | 6692 |
| 415 | Spp1 | 20750 | 6696 |
| 416 | Src | 20779 | 6714 |
| 417 | Sstr2 | 20606 | 6752 |
| 418 | St14 | 19143 | 6768 |
| 419 | Stambpl1 | 76630 | 57559 |
| 420 | Stat4 | 20849 | 6775 |
| 421 | Steap2 | 74051 | 261729 |
| 422 | Tgfb2 | 21808 | 7042 |
| 423 | Timp3 | 21859 | 7078 |
| 424 | Tm4sf4 | 229302 | 7104 |

TABLE 1-continued

HybHP marker genes that are upregulated in HybHP compared to cHP. Bold italics text (numbered 1-193 in the first column) reflect genes that are also expressed in ductal cells.

| | Mouse gene name | Mouse Entrez gene ID | Human Entrez gene ID |
|---|---|---|---|
| 425 | Tmem229a | 319832 | 730130 |
| 426 | Tmem45a | 56277 | 55076 |
| 427 | Tspan8 | 216350 | 7103 |
| 428 | Tstd1 | 226654 | 100131187 |
| 429 | Vwf | 22371 | 7450 |
| 430 | Wnt4 | 22417 | 54361 |
| 431 | Zfp248 | 72720 | #N/A |
| 432 | Aim1l | 230806 | 55057 |
| 433 | Aldh1b1 | 72535 | 219 |
| 434 | Apoa4 | 11808 | 337 |
| 435 | Apoc2 | 11813 | 344 |
| 436 | Aqp4 | 11829 | 361 |
| 437 | Arhgap10 | 78514 | 79658 |
| 438 | Atp4a | 11944 | 495 |
| 439 | Bdh2 | 69772 | 56898 |
| 440 | Cbs | 12411 | 875 |
| 441 | Cib3 | 234421 | 117286 |
| 442 | Clic5 | 224796 | 53405 |
| 443 | Cryl1 | 68631 | 51084 |
| 444 | Ctnnbip1 | 67087 | 56998 |
| 445 | Ctsc | 13032 | 1075 |
| 446 | Cyp2f2 | 13107 | #N/A |
| 447 | Defb1 | 13214 | 1672 |
| 448 | Efna3 | 100046031 | 1944 |
| 449 | Efna3 | 13638 | 1944 |
| 450 | Fbp1 | 14121 | 2203 |
| 451 | Gas2 | 14453 | 2620 |
| 452 | Gldc | 104174 | 2731 |
| 453 | Gls2 | 216456 | 27165 |
| 454 | Gucy2c | 14917 | 2984 |
| 455 | Hal | 15109 | 3034 |
| 456 | Hsbp1l1 | 66255 | 440498 |
| 457 | Hsd17b13 | 243168 | 345275 |
| 458 | Hsd17b6 | 27400 | 8630 |
| 459 | Kcp | 333088 | 375610 |
| 460 | Mrgpre | 244238 | 116534 |
| 461 | Ncam2 | 17968 | 4685 |
| 462 | Olfm3 | 229759 | 118427 |
| 463 | Osbp2 | 100044882 | 23762 |
| 464 | Osbp2 | 74309 | 23762 |
| 465 | Plxna2 | 18845 | 5362 |
| 466 | Ptgds | 19215 | 5730 |
| 467 | Ptges | 64292 | 9536 |
| 468 | Sdsl | 257635 | 113675 |
| 469 | Serpina12 | 68054 | 145264 |
| 470 | Sulf2 | 72043 | 55959 |
| 471 | Tbc1d30 | 74694 | 23329 |
| 472 | Tmprss4 | 214523 | 56649 |
| 473 | Ugt2b38 | 100559 | #N/A |
| 474 | Xirp1 | 22437 | 165904 |

TABLE 2

HybHP marker genes that are downregulated in HybHP cells compared to cHP cells. Bold italics text (numbered 1-118 in the first column) reflect genes that are specifically downregulated in HybHP compared to cHP and BD. Text that is neither in bold nor in italics (numbered 119-573 in the first column) reflect genes that are downregulated both in HybHP and BD compared to cHP.

| | Mouse gene name | Mouse Entrez gene ID | Human Entrez gene ID |
|---|---|---|---|
| 1 | *9330182L06Rik* | 231014 | #N/A |
| 2 | *Acot1* | 26897 | 641371 |
| 3 | *Adcy1* | 432530 | 107 |
| 4 | *Aif1* | 11629 | 199 |
| 5 | *Angptl2* | 26360 | 23452 |
| 6 | *Arhgap19* | 71085 | 84986 |
| 7 | *Axl* | 26362 | 558 |
| 8 | *B3galnt1* | 26879 | 8706 |
| 9 | *Bmp7* | 12162 | 655 |
| 10 | *Btk* | 12229 | 695 |
| 11 | *C1qa* | 12259 | 712 |
| 12 | *C1qb* | 12260 | 713 |
| 13 | *C1qc* | 12262 | 714 |
| 14 | *Casc4* | 319996 | 113201 |
| 15 | *Ccl6* | 20305 | #N/A |
| 16 | *Ccnd1* | 12443 | 595 |
| 17 | *Cd163* | 93671 | 9332 |
| 18 | *Cd300ld* | 217305 | 100131439 |
| 19 | *Cd300ld* | 100046097 | 100131439 |
| 20 | *Cd44* | 12505 | 960 |
| 21 | *Cd53* | 12508 | 963 |
| 22 | *Cd5l* | 11801 | 922 |
| 23 | *Cd74* | 16149 | 972 |
| 24 | *Cd86* | 12524 | 942 |
| 25 | *Celf2* | 14007 | 10659 |
| 26 | *Cfp* | 18636 | 5199 |
| 27 | *Cldn2* | 12738 | 9075 |
| 28 | *Clec4a3* | 73149 | #N/A |
| 29 | *Clec4f* | 51811 | 165530 |
| 30 | *Clec4n* | 56620 | #N/A |
| 31 | *Clec7a* | 56644 | 64581 |
| 32 | *Col5a1* | 12831 | 1289 |
| 33 | *Coro2a* | 107684 | 7464 |
| 34 | *Csf1r* | 12978 | 1436 |
| 35 | *Ctse* | 13034 | 1510 |
| 36 | *Ctss* | 13040 | 1520 |
| 37 | *Cybb* | 13058 | 1536 |
| 38 | *D630039A03Rik* | 242484 | #N/A |
| 39 | *Dock10* | 210293 | 55619 |
| 40 | *Efr3b* | 668212 | 22979 |
| 41 | *Emr1* | 13733 | 2015 |
| 42 | *Emr4* | 52614 | #N/A |
| 43 | *Endod1* | 71946 | 23052 |
| 44 | *Fam107b* | 66540 | 83641 |
| 45 | *Fcgr3* | 14131 | #N/A |
| 46 | *Fcgr4* | 246256 | #N/A |
| 47 | *Fcna* | 14133 | #N/A |
| 48 | *Fgd2* | 26382 | 221472 |
| 49 | *Fgl2* | 14190 | 10875 |
| 50 | *Fhad1* | 329977 | 114827 |
| 51 | *Folr2* | 14276 | 2350 |
| 52 | *Fyb* | 23880 | 2533 |
| 53 | *Gna14* | 14675 | 9630 |
| 54 | *Gpr64* | 237175 | 10149 |
| 55 | *H2-Aa* | 14960 | #N/A |
| 56 | *H2-Aa* | 14968 | #N/A |
| 57 | *H2-DMa* | 14998 | #N/A |
| 58 | *Hck* | 15162 | 3055 |
| 59 | *Hk2* | 15277 | 642546 |
| 60 | *Hk3* | 212032 | 3101 |
| 61 | *Igsf6* | 80719 | 10261 |
| 62 | *Itgal* | 16408 | 3683 |
| 63 | *Itgb2* | 16414 | 3689 |
| 64 | *Kctd12* | 239272 | 115207 |
| 65 | *Laptm5* | 16792 | 7805 |
| 66 | *Lgals3* | 16854 | 3958 |
| 67 | *Lilra5* | 232801 | 353514 |
| 68 | *Lilrb4* | 14728 | 11006 |
| 69 | *Lilrb4* | 14727 | 11006 |
| 70 | *Lpl* | 16956 | 4023 |
| 71 | *Lpl* | 669888 | 4023 |
| 72 | *Lyz2* | 17105 | #N/A |
| 73 | *Mpeg1* | 17476 | 219972 |
| 74 | *Ncf1* | 17969 | 653361 |
| 75 | *Nckap1l* | 105855 | 3071 |
| 76 | *Ndrg1* | 17988 | 10397 |
| 77 | *Npr2* | 230103 | 4882 |

TABLE 2-continued

HybHP marker genes that are downregulated in HybHP cells compared to cHP cells. Bold italics text (numbered 1-118 in the first column) reflect genes that are specifically downregulated in HybHP compared to cHP and BD. Text that is neither in bold nor in italics (numbered 119-573 in the first column) reflect genes that are downregulated both in HybHP and BD compared to cHP.

| | Mouse gene name | Mouse Entrez gene ID | Human Entrez gene ID |
|---|---|---|---|
| 78 | *Nr4a2* | 18227 | 4929 |
| 79 | *Nt5dc2* | 70021 | 64943 |
| 80 | *Olfr1033* | 258571 | #N/A |
| 81 | *P2ry12* | 70839 | 64805 |
| 82 | *Papln* | 170721 | 89932 |
| 83 | *Pdgfc* | 54635 | 56034 |
| 84 | *Pkib* | 18768 | 5570 |
| 85 | *Pla2g12a* | 66350 | 81579 |
| 86 | *Pla2g7* | 27226 | 7941 |
| 87 | *Pld4* | 104759 | 122618 |
| 88 | *Plek* | 56193 | 5341 |
| 89 | *Pmm1* | 29858 | 5372 |
| 90 | *Postn* | 50706 | 10631 |
| 91 | *Prkcb* | 18751 | 5579 |
| 92 | *Ptprc* | 19264 | 5788 |
| 93 | *Rac2* | 19354 | 5880 |
| 94 | *Rcan2* | 53901 | 10231 |
| 95 | *Rec8* | 56739 | 9985 |
| 96 | *Reln* | 19699 | 5649 |
| 97 | *Ripply1* | 622473 | 92129 |
| 98 | *Sdc3* | 20970 | 9672 |
| 99 | *Siglec1* | 20612 | 6614 |
| 100 | *Siglece* | 83382 | #N/A |
| 101 | *Slc11a1* | 18173 | 6556 |
| 102 | *Slc16a11* | 216867 | 162515 |
| 103 | *Slc16a13* | 69309 | 201232 |
| 104 | *Slc16a9* | 66859 | 220963 |
| 105 | *Slc1a5* | 20514 | 6510 |
| 106 | *Tgfbi* | 21810 | 7045 |
| 107 | *Tgfbr3* | 21814 | 7049 |
| 108 | *Themis* | 210757 | 387357 |
| 109 | *Tlr5* | 53791 | 7100 |
| 110 | *Tlr8* | 170744 | 51311 |
| 111 | *Tnfrsf19* | 29820 | 55504 |
| 112 | *Tnfrsf21* | 94185 | 27242 |
| 113 | *Trpm2* | 28240 | 7226 |
| 114 | *Tsc22d1* | 21807 | 8848 |
| 115 | *Tyrobp* | 22177 | 7305 |
| 116 | *Ubd* | 24108 | 10537 |
| 117 | *Vldlr* | 22359 | 7436 |
| 118 | *Vsig4* | 278180 | 11326 |
| 119 | 1500017E21Rik | 668215 | #N/A |
| 120 | 1810058I24Rik | 67705 | #N/A |
| 121 | 2210417A02Rik | 70138 | #N/A |
| 122 | Abcb1b | 18669 | #N/A |
| 123 | Abcg8 | 67470 | 64241 |
| 124 | Abi3 | 66610 | 51225 |
| 125 | Acsm5 | 272428 | 54988 |
| 126 | Adam11 | 11488 | 4185 |
| 127 | Adamts13 | 279028 | 11093 |
| 128 | Adrb3 | 11556 | 155 |
| 129 | Ahr | 11622 | 196 |
| 130 | Akr1c6 | 83702 | #N/A |
| 131 | Aldh1a1 | 11668 | 216 |
| 132 | Aldh3a2 | 11671 | 224 |
| 133 | Ang | 11727 | 283 |
| 134 | Aqp9 | 64008 | 366 |
| 135 | Asns | 27053 | 440 |
| 136 | Atp6v0d2 | 242341 | 245972 |
| 137 | Avpr1a | 54140 | 552 |
| 138 | AW549542 | 100993 | #N/A |
| 139 | Axin2 | 12006 | 8313 |
| 140 | Blvrb | 233016 | 645 |
| 141 | Cela1 | 109901 | 1990 |
| 142 | Chic1 | 12212 | 53344 |
| 143 | Chrna2 | 110902 | 1135 |
| 144 | Cib2 | 56506 | 10518 |
| 145 | Csad | 246277 | 51380 |
| 146 | Csrp3 | 13009 | 8048 |
| 147 | Cxcl9 | 17329 | 4283 |
| 148 | Cyp1a2 | 13077 | 1544 |
| 149 | Cyp27a1 | 104086 | 1593 |
| 150 | Cyp2a22 | 233005 | #N/A |
| 151 | Cyp2a22 | 13085 | #N/A |
| 152 | Cyp2a5 | 330491 | #N/A |
| 153 | Cyp2a5 | 13087 | #N/A |
| 154 | Cyp2c29 | 13095 | #N/A |
| 155 | Cyp2c37 | 13096 | #N/A |
| 156 | Cyp2c37 | 100046484 | #N/A |
| 157 | Cyp2c38 | 13097 | #N/A |
| 158 | Cyp2c39 | 13098 | #N/A |
| 159 | Cyp2c40 | 100048323 | #N/A |
| 160 | Cyp2c40 | 545288 | #N/A |
| 161 | Cyp2c40 | 13099 | #N/A |
| 162 | Cyp2c40 | 100043108 | #N/A |
| 163 | Cyp2c50 | 107141 | #N/A |
| 164 | Cyp2c54 | 404195 | #N/A |
| 165 | Cyp2c54 | 639023 | #N/A |
| 166 | Cyp2c54 | 100044352 | #N/A |
| 167 | Cyp2c67 | 100048323 | #N/A |
| 168 | Cyp2c67 | 545288 | #N/A |
| 169 | Cyp2c67 | 13099 | #N/A |
| 170 | Cyp2c67 | 100043108 | #N/A |
| 171 | Cyp2c69 | 100048323 | #N/A |
| 172 | Cyp2c69 | 545288 | #N/A |
| 173 | Cyp2c69 | 13099 | #N/A |
| 174 | Cyp2c69 | 100043108 | #N/A |
| 175 | Cyp2e1 | 13106 | 1571 |
| 176 | Cyp2g1 | 13108 | #N/A |
| 177 | Cyp7a1 | 13122 | 1581 |
| 178 | Dcn | 13179 | 1634 |
| 179 | Dntt | 21673 | 1791 |
| 180 | E2f8 | 108961 | 79733 |
| 181 | Ecm1 | 13601 | 1893 |
| 182 | Egln3 | 112407 | 112399 |
| 183 | Esrrg | 26381 | 2104 |
| 184 | Fam89a | 69627 | 375061 |
| 185 | Fam89a | 100047808 | 375061 |
| 186 | Fam89a | 677631 | 375061 |
| 187 | Fbxl21 | 213311 | 26223 |
| 188 | Fitm1 | 68680 | 161247 |
| 189 | Fmo3 | 14262 | 2328 |
| 190 | Gabrb3 | 14402 | 2562 |
| 191 | Gas7 | 14457 | 8522 |
| 192 | Gbp10 | 626578 | #N/A |
| 193 | Gbp10 | 76074 | #N/A |
| 194 | Gbp10 | 634650 | #N/A |
| 195 | Glul | 240219 | 2752 |
| 196 | Glul | 14645 | 2752 |
| 197 | Gsta3 | 14859 | 2940 |
| 198 | Gstm1 | 433943 | 2944 |
| 199 | Gstm1 | 100043965 | 2944 |
| 200 | Gstm1 | 14862 | 2944 |
| 201 | Gstm2 | 14863 | 2946 |
| 202 | Gstm2 | 626327 | 2946 |
| 203 | Gstm3 | 14864 | 2947 |
| 204 | Gstm6 | 14867 | #N/A |
| 205 | Gulo | 268756 | 2989 |
| 206 | H2-Q1 | 15006 | #N/A |
| 207 | H2-Q1 | 15018 | #N/A |
| 208 | H2-Q1 | 110558 | #N/A |
| 209 | H2-Q1 | 100044307 | #N/A |
| 210 | H2-Q1 | 68395 | #N/A |
| 211 | H2-Q1 | 676708 | #N/A |
| 212 | H2-Q1 | 15019 | #N/A |
| 213 | H2-Q1 | 100044021 | #N/A |
| 214 | H2-Q1 | 100044020 | #N/A |
| 215 | H2-Q1 | 110557 | #N/A |
| 216 | H2-Q1 | 100044019 | #N/A |
| 217 | H2-Q1 | 15013 | #N/A |

TABLE 2-continued

HybHP marker genes that are downregulated in HybHP cells compared to cHP cells. Bold italics text (numbered 1-118 in the first column) reflect genes that are specifically downregulated in HybHP compared to cHP and BD. Text that is neither in bold nor in italics (numbered 119-573 in the first column) reflect genes that are downregulated both in HybHP and BD compared to cHP.

| | Mouse gene name | Mouse Entrez gene ID | Human Entrez gene ID |
|---|---|---|---|
| 218 | Hamp2 | 66438 | #N/A |
| 219 | Hand2 | 15111 | 9464 |
| 220 | Hcrtr2 | 387285 | 3062 |
| 221 | Hhip | 15245 | 64399 |
| 223 | Hsd3b7 | 101502 | 55124 |
| 224 | Kif26b | 269152 | 55083 |
| 225 | Lama1 | 16772 | 284217 |
| 226 | Lect1 | 16840 | 11061 |
| 227 | Lect2 | 16841 | 3950 |
| 228 | Lgr5 | 14160 | 8549 |
| 229 | Lhpp | 76429 | 64077 |
| 230 | Lifr | 16880 | 3977 |
| 231 | Mab21l2 | 23937 | 10586 |
| 232 | Meg3 | 17263 | 55384 |
| 233 | Mirg | 100040724 | #N/A |
| 234 | Mycn | 18109 | 4613 |
| 235 | Nkd1 | 634379 | 85407 |
| 236 | Nkd1 | 93960 | 85407 |
| 237 | Notum | 77583 | 147111 |
| 238 | Nr1i3 | 12355 | 9970 |
| 239 | Nrn1 | 68404 | 51299 |
| 240 | Nt5e | 23959 | 4907 |
| 241 | Ntn1 | 672215 | 9423 |
| 242 | Ntn1 | 18208 | 9423 |
| 243 | Oat | 18242 | 4942 |
| 244 | Olig1 | 50914 | 116448 |
| 245 | Paqr9 | 75552 | 344838 |
| 246 | Pcp4l1 | 66425 | 654790 |
| 247 | Phospho1 | 237928 | 162466 |
| 248 | Pir | 69656 | 8544 |
| 249 | Plbd1 | 66857 | 79887 |
| 250 | Plbd1 | 100045163 | 79887 |
| 251 | Pon1 | 18979 | 5444 |
| 252 | Pparg | 19016 | 5468 |
| 253 | Prrx1 | 18933 | 5396 |
| 254 | Rap2a | 76108 | 5911 |
| 255 | Rarres1 | 109222 | 5918 |
| 256 | Rdh9 | 103142 | #N/A |
| 257 | Rfx4 | 71137 | 5992 |
| 258 | Rgn | 19733 | 9104 |
| 259 | Rhbg | 58176 | 57127 |
| 260 | Rian | 75745 | #N/A |
| 261 | Rnase4 | 58809 | 6038 |
| 262 | Robo1 | 19876 | 642132 |
| 263 | Sema5b | 20357 | 54437 |
| 264 | Serpina7 | 331535 | 6906 |
| 265 | Sh2d7 | 244885 | 646892 |
| 266 | Slc13a3 | 114644 | 64849 |
| 267 | Slc13a4 | 243755 | 26266 |
| 268 | Slc16a10 | 72472 | 117247 |
| 269 | Slc1a2 | 20511 | 6506 |
| 270 | Slc1a4 | 55963 | 6509 |
| 271 | Slc22a1 | 20517 | 6580 |
| 272 | Slc22a3 | 20519 | 6581 |
| 273 | Slc25a21 | 217593 | 89874 |
| 274 | Slc26a4 | 23985 | 5172 |
| 275 | Slco1a1 | 28248 | #N/A |
| 276 | Slco1b2 | 28253 | #N/A |
| 277 | Sp5 | 64406 | 389058 |
| 278 | Susd4 | 96935 | 55061 |
| 279 | Tbx3 | 21386 | 6926 |
| 280 | Tlr12 | 384059 | #N/A |
| 281 | Tmeff2 | 56363 | 23671 |
| 282 | Tnfaip8l1 | 66443 | 126282 |
| 283 | Tomm40l | 641376 | 84134 |
| 284 | Ttc7b | 104718 | 145567 |
| 285 | Ube2e2 | 218793 | 7325 |
| 286 | Vnn1 | 22361 | 8876 |
| 287 | From | mouse | human |
| 288 | 9330182L06Rik | 231014 | #N/A |
| 289 | Acot1 | 26897 | 641371 |
| 290 | Adcy1 | 432530 | 107 |
| 291 | Aif1 | 11629 | 199 |
| 292 | Angptl2 | 26360 | 23452 |
| 293 | Arhgap19 | 71085 | 84986 |
| 294 | Axl | 26362 | 558 |
| 295 | B3galnt1 | 26879 | 8706 |
| 296 | Bmp7 | 12162 | 655 |
| 297 | Btk | 12229 | 695 |
| 298 | C1qa | 12259 | 712 |
| 299 | C1qb | 12260 | 713 |
| 300 | C1qc | 12262 | 714 |
| 301 | Casc4 | 319996 | 113201 |
| 302 | Ccl6 | 20305 | #N/A |
| 303 | Ccnd1 | 12443 | 595 |
| 304 | Cd163 | 93671 | 9332 |
| 305 | Cd300ld | 217305 | 100131439 |
| 306 | Cd300ld | 100046097 | 100131439 |
| 307 | Cd44 | 12505 | 960 |
| 308 | Cd53 | 12508 | 963 |
| 309 | Cd51 | 11801 | 922 |
| 310 | Cd74 | 16149 | 972 |
| 311 | Cd86 | 12524 | 942 |
| 312 | Celf2 | 14007 | 10659 |
| 313 | Cfp | 18636 | 5199 |
| 314 | Cldn2 | 12738 | 9075 |
| 315 | Clec4a3 | 73149 | #N/A |
| 316 | Clec4f | 51811 | 165530 |
| 317 | Clec4n | 56620 | #N/A |
| 318 | Clec7a | 56644 | 64581 |
| 319 | Col5a1 | 12831 | 1289 |
| 320 | Coro2a | 107664 | 7464 |
| 321 | Csf1r | 12978 | 1436 |
| 322 | Ctse | 13034 | 1510 |
| 323 | Ctss | 13040 | 1520 |
| 324 | Cybb | 13058 | 1536 |
| 325 | D630039A03Rik | 242484 | #N/A |
| 326 | Dock10 | 210293 | 55619 |
| 327 | Efr3b | 668212 | 22979 |
| 328 | Emr1 | 13733 | 2015 |
| 329 | Emr4 | 52614 | #N/A |
| 330 | Endod1 | 71946 | 23052 |
| 331 | Fam107b | 66540 | 83641 |
| 332 | Fcgr3 | 14131 | #N/A |
| 333 | Fcgr4 | 246256 | #N/A |
| 334 | Fcna | 14133 | #N/A |
| 335 | Fgd2 | 26382 | 221472 |
| 336 | Fgl2 | 14190 | 10875 |
| 337 | Fhad1 | 329977 | 114827 |
| 338 | Folr2 | 14276 | 2350 |
| 339 | Fyb | 23880 | 2533 |
| 340 | Gna14 | 14675 | 9630 |
| 341 | Gpr64 | 237175 | 10149 |
| 342 | H2-Aa | 14960 | #N/A |
| 343 | H2-Aa | 14968 | #N/A |
| 344 | H2-DMa | 14998 | #N/A |
| 345 | Hck | 15162 | 3055 |
| 346 | Hk2 | 15277 | 642546 |
| 347 | Hk3 | 212032 | 3101 |
| 348 | Igsf6 | 80719 | 10261 |
| 349 | Itgal | 16408 | 3683 |
| 350 | Itgb2 | 16414 | 3689 |
| 351 | Kctd12 | 239217 | 115207 |
| 352 | Laptm5 | 16792 | 7805 |
| 353 | Lgals3 | 16854 | 3958 |
| 354 | Lilra5 | 232801 | 353514 |
| 355 | Lilrb4 | 14728 | 11006 |
| 356 | Lilrb4 | 14727 | 11006 |
| 357 | Lpl | 16956 | 4023 |
| 358 | Lpl | 669888 | 4023 |

TABLE 2-continued

HybHP marker genes that are downregulated in HybHP cells compared to cHP cells. Bold italics text (numbered 1-118 in the first column) reflect genes that are specifically downregulated in HybHP compared to cHP and BD. Text that is neither in bold nor in italics (numbered 119-573 in the first column) reflect genes that are downregulated both in HybHP and BD compared to cHP.

| | Mouse gene name | Mouse Entrez gene ID | Human Entrez gene ID |
|---|---|---|---|
| 359 | Lyz2 | 17105 | #N/A |
| 360 | Mpeg1 | 17476 | 219972 |
| 361 | Ncf1 | 17969 | 653361 |
| 362 | Nckap1l | 105855 | 3071 |
| 363 | Ndrg1 | 17988 | 10397 |
| 364 | Npr2 | 230103 | 4882 |
| 365 | Nr4a2 | 18227 | 4929 |
| 366 | Nt5dc2 | 70021 | 64943 |
| 367 | Olfr1033 | 258571 | #N/A |
| 368 | P2ry12 | 70839 | 64805 |
| 369 | Papln | 170721 | 89932 |
| 370 | Pdgfc | 54635 | 56034 |
| 371 | Pkib | 18768 | 5570 |
| 372 | Pla2g12a | 66350 | 81579 |
| 373 | Pla2g7 | 27226 | 7941 |
| 374 | Pld4 | 104759 | 122618 |
| 375 | Plek | 56193 | 5341 |
| 376 | Pmm1 | 29858 | 5372 |
| 377 | Postn | 50706 | 10631 |
| 378 | Prkcb | 18751 | 5579 |
| 379 | Ptprc | 19264 | 5788 |
| 380 | Rac2 | 19354 | 5880 |
| 381 | Rcan2 | 53901 | 10231 |
| 382 | Rec8 | 56739 | 9985 |
| 383 | Reln | 19699 | 5649 |
| 384 | Ripply1 | 622473 | 92129 |
| 385 | Sdc3 | 20970 | 9672 |
| 386 | Siglec1 | 20612 | 6614 |
| 387 | Siglece | 83382 | #N/A |
| 388 | Slc11a1 | 18173 | 6556 |
| 389 | Slc16a11 | 216867 | 162515 |
| 390 | Slc16a13 | 69309 | 201232 |
| 391 | Slc16a9 | 66859 | 220963 |
| 392 | Slc1a5 | 20514 | 6510 |
| 393 | Tgfbi | 21810 | 7045 |
| 394 | Tgfbr3 | 21814 | 7049 |
| 395 | Themis | 210757 | 387357 |
| 396 | Tlr5 | 53791 | 7100 |
| 397 | Tlr8 | 170744 | 51311 |
| 398 | Tnfrsf19 | 29820 | 55504 |
| 399 | Tnfrsf21 | 94185 | 27242 |
| 400 | Trpm2 | 28240 | 7226 |
| 401 | Tsc22d1 | 21807 | 8848 |
| 402 | Tyrobp | 22177 | 7305 |
| 403 | Ubd | 24108 | 10537 |
| 404 | Vldlr | 22359 | 7436 |
| 405 | Vsig4 | 278180 | 11326 |
| 406 | 1500017E21Rik | 668215 | #N/A |
| 407 | 1810058I24Rik | 67705 | #N/A |
| 408 | 2210417A02Rik | 70138 | #N/A |
| 409 | Abcb1b | 18669 | #N/A |
| 410 | Abcg8 | 67470 | 64241 |
| 411 | Abi3 | 66610 | 51225 |
| 412 | Acsm5 | 272428 | 54988 |
| 413 | Adam11 | 11488 | 4185 |
| 414 | Adamts13 | 279028 | 11093 |
| 415 | Adrb3 | 11556 | 155 |
| 416 | Ahr | 11622 | 196 |
| 417 | Akr1c6 | 83702 | #N/A |
| 418 | Aldh1a1 | 11668 | 216 |
| 419 | Aldh3a2 | 11671 | 224 |
| 420 | Ang | 11727 | 283 |
| 421 | Aqp9 | 64008 | 366 |
| 422 | Asns | 27053 | 440 |
| 423 | Atp6v0d2 | 242341 | 245972 |
| 424 | Avpr1a | 54140 | 552 |
| 425 | AW549542 | 100993 | #N/A |
| 426 | Axin2 | 12006 | 8313 |
| 427 | Blvrb | 233016 | 645 |
| 428 | Cela1 | 109901 | 1990 |
| 429 | Chic1 | 12212 | 53344 |
| 430 | Chrna2 | 110902 | 1135 |
| 431 | Cib2 | 56506 | 10518 |
| 432 | Csad | 246277 | 51380 |
| 433 | Csrp3 | 13009 | 8048 |
| 434 | Cxcl9 | 17329 | 4283 |
| 435 | Cyp1a2 | 13077 | 1544 |
| 436 | Cyp27a1 | 104086 | 1593 |
| 437 | Cyp2a22 | 233005 | #N/A |
| 438 | Cyp2a22 | 13085 | #N/A |
| 439 | Cyp2a5 | 330491 | #N/A |
| 440 | Cyp2a5 | 13087 | #N/A |
| 441 | Cyp2c29 | 13095 | #N/A |
| 442 | Cyp2c37 | 13096 | #N/A |
| 443 | Cyp2c37 | 100046484 | #N/A |
| 444 | Cyp2c38 | 13097 | #N/A |
| 445 | Cyp2c39 | 13098 | #N/A |
| 446 | Cyp2c40 | 100048323 | #N/A |
| 447 | Cyp2c40 | 545288 | #N/A |
| 448 | Cyp2c40 | 13099 | #N/A |
| 449 | Cyp2c40 | 100043108 | #N/A |
| 450 | Cyp2c50 | 107141 | #N/A |
| 451 | Cyp2c54 | 404195 | #N/A |
| 452 | Cyp2c54 | 639023 | #N/A |
| 453 | Cyp2c54 | 100044352 | #N/A |
| 454 | Cyp2c67 | 100048323 | #N/A |
| 455 | Cyp2c67 | 545288 | #N/A |
| 456 | Cyp2c67 | 13099 | #N/A |
| 457 | Cyp2c67 | 100043108 | #N/A |
| 458 | Cyp2c69 | 100048323 | #N/A |
| 459 | Cyp2c69 | 545288 | #N/A |
| 460 | Cyp2c69 | 13099 | #N/A |
| 461 | Cyp2c69 | 100043108 | #N/A |
| 462 | Cyp2e1 | 13106 | 1571 |
| 463 | Cyp2g1 | 13108 | #N/A |
| 464 | Cyp7a1 | 13122 | 1581 |
| 465 | Dcn | 13179 | 1634 |
| 466 | Dntt | 21673 | 1791 |
| 467 | E2f8 | 108961 | 79733 |
| 468 | Ecm1 | 13601 | 1893 |
| 469 | Egln3 | 112407 | 112399 |
| 470 | Esrrg | 26381 | 2104 |
| 471 | Fam89a | 69627 | 375061 |
| 472 | Fam89a | 100047808 | 375061 |
| 473 | Fam89a | 677631 | 375061 |
| 474 | Fbxl21 | 213311 | 26223 |
| 475 | Fitm1 | 68680 | 161247 |
| 476 | Fmo3 | 14262 | 2328 |
| 477 | Gabrb3 | 14402 | 2562 |
| 478 | Gas7 | 14457 | 8522 |
| 479 | Gbp10 | 626578 | #N/A |
| 480 | Gbp10 | 76074 | #N/A |
| 481 | Gbp10 | 634650 | #N/A |
| 482 | Glul | 240219 | 2752 |
| 483 | Glul | 14645 | 2752 |
| 484 | Gsta3 | 14859 | 2940 |
| 485 | Gstm1 | 433943 | 2944 |
| 486 | Gstm1 | 100043965 | 2944 |
| 487 | Gstm1 | 14862 | 2944 |
| 488 | Gstm2 | 14863 | 2946 |
| 489 | Gstm2 | 626327 | 2946 |
| 490 | Gstm3 | 14864 | 2947 |
| 491 | Gstm6 | 14867 | #N/A |
| 492 | Gulo | 268756 | #N/A |
| 493 | H2-Q1 | 15006 | #N/A |
| 494 | H2-Q1 | 15018 | #N/A |
| 495 | H2-Q1 | 110558 | #N/A |
| 496 | H2-Q1 | 100044307 | #N/A |
| 497 | H2-Q1 | 68395 | #N/A |
| 498 | H2-Q1 | 676708 | #N/A |

TABLE 2-continued

HybHP marker genes that are downregulated in HybHP cells compared to cHP cells. Bold italics text (numbered 1-118 in the first column) reflect genes that are specifically downregulated in HybHP compared to cHP and BD. Text that is neither in bold nor in italics (numbered 119-573 in the first column) reflect genes that are downregulated both in HybHP and BD compared to cHP.

| | Mouse gene name | Mouse Entrez gene ID | Human Entrez gene ID |
|---|---|---|---|
| 499 | H2-Q1 | 15019 | #N/A |
| 500 | H2-Q1 | 100044021 | #N/A |
| 501 | H2-Q1 | 100044020 | #N/A |
| 502 | H2-Q1 | 110557 | #N/A |
| 503 | H2-Q1 | 100044019 | #N/A |
| 504 | H2-Q1 | 15013 | #N/A |
| 505 | Hamp2 | 66438 | #N/A |
| 506 | Hand2 | 15111 | 9464 |
| 507 | Hcrtr2 | 387285 | 3062 |
| 508 | Hhip | 15245 | 64399 |
| 509 | Hsd3b7 | 101502 | 55124 |
| 510 | Kif26b | 269152 | 55083 |
| 511 | Lama1 | 16772 | 284217 |
| 512 | Lect1 | 16840 | 11061 |
| 513 | Lect2 | 16841 | 3950 |
| 514 | Lgr5 | 14160 | 8549 |
| 515 | Lhpp | 76429 | 64077 |
| 516 | Lifr | 16880 | 3977 |
| 517 | Mab21l2 | 23937 | 10586 |
| 518 | Meg3 | 17263 | 55384 |
| 519 | Mirg | 100040724 | #N/A |
| 520 | Mycn | 18109 | 4613 |
| 521 | Nkd1 | 634379 | 85407 |
| 522 | Nkd1 | 93960 | 85407 |
| 523 | Notum | 77583 | 147111 |
| 524 | Nr1i3 | 12355 | 9970 |
| 525 | Nrn1 | 68404 | 51299 |
| 526 | Nt5e | 23959 | 4907 |
| 527 | Ntn1 | 672215 | 9423 |
| 528 | Ntn1 | 18208 | 9423 |
| 529 | Oat | 18242 | 4942 |
| 530 | Olig1 | 50914 | 116448 |
| 531 | Paqr9 | 75552 | 344838 |
| 532 | Pcp4l1 | 66425 | 654790 |
| 533 | Phospho1 | 237928 | 162466 |
| 534 | Pir | 69656 | 8544 |
| 535 | Plbd1 | 66857 | 79887 |
| 536 | Plbd1 | 66857 | 79887 |
| 537 | Plbd1 | 100045163 | 79887 |
| 538 | Pon1 | 18979 | 5444 |
| 539 | Pparg | 19016 | 5468 |
| 540 | Prrx1 | 18933 | 5396 |
| 541 | Rap2a | 76108 | 5911 |
| 542 | Rarres1 | 109222 | 5918 |
| 543 | Rdh9 | 103142 | #N/A |
| 544 | Rfx4 | 71137 | 5992 |
| 545 | Rgn | 19733 | 9104 |
| 546 | Rhbg | 58176 | 57127 |
| 547 | Rian | 75745 | #N/A |
| 548 | Rnase4 | 58809 | 6038 |
| 549 | Robo1 | 19876 | 642132 |
| 550 | Sema5b | 20357 | 54437 |
| 551 | Serpina7 | 331535 | 6906 |
| 552 | Sh2d7 | 244885 | 646892 |
| 553 | Slc13a3 | 114644 | 64849 |
| 554 | Slc13a4 | 243755 | 26266 |
| 555 | Slc16a10 | 72472 | 117247 |
| 556 | Slc1a2 | 20511 | 6506 |
| 557 | Slc1a4 | 55963 | 6509 |
| 558 | Slc22a1 | 20517 | 6580 |
| 559 | Slc22a3 | 20519 | 6581 |
| 560 | Slc25a21 | 217593 | 89874 |
| 561 | Slc26a4 | 23985 | 5172 |
| 562 | Slco1a1 | 28248 | #N/A |
| 563 | Slco1b2 | 28253 | #N/A |
| 564 | Sp5 | 64406 | 389058 |
| 565 | Susd4 | 96935 | 55061 |
| 566 | Tbx3 | 21386 | 6926 |
| 567 | Tlr12 | 384059 | #N/A |
| 568 | Tmeff2 | 56363 | 23671 |
| 569 | Tnfaip8l1 | 66443 | 126282 |
| 570 | Tomm40l | 641376 | 84134 |
| 571 | Ttc7b | 104718 | 145567 |
| 572 | Ube2e2 | 218793 | 7325 |
| 573 | Vnn1 | 22361 | 8876 |

TABLE 3

HybHP marker genes for isolation of HybHP cells, that are located on the plasma membrane, and that are upregulated in HybHP compared to cHP. Bold italics text (numbered 1-64 in the first column) reflects genes that are also expressed in ductal cells.

| | Mouse gene name | Mouse Entrez gene ID | Human Entrez gene ID |
|---|---|---|---|
| 1 | *Abcc5* | 27416 | 10057 |
| 2 | *Ano1* | 101772 | 55107 |
| 3 | *Anxa13* | 69787 | 312 |
| 4 | *App* | 11820 | 351 |
| 5 | *Atp1b1* | 11931 | 481 |
| 6 | *Bcam* | 57278 | 4059 |
| 7 | *Cd200* | 100048780 | 4345 |
| 8 | *Cd200* | 17470 | 4345 |
| 9 | *Cd24a* | 12484 | #N/A |
| 10 | *Cd63* | 12512 | 967 |
| 11 | *Cdh1* | 12550 | 999 |
| 12 | *Celsr1* | 12614 | 9620 |
| 13 | *Chrm3* | 12671 | 1131 |
| 14 | *Chrnb1* | 11443 | 1140 |
| 15 | *Cldn6* | 54419 | 284620 |
| 16 | *Cldn7* | 53624 | 1366 |
| 17 | *Cttnbp2* | 30785 | 83992 |
| 18 | *Ddr1* | 12305 | 780 |
| 19 | *Ednrb* | 13618 | 1910 |
| 20 | *Egflam* | 268780 | 133584 |
| 21 | *Ehd2* | 259300 | 30846 |
| 22 | *Enah* | 13800 | 55740 |
| 23 | *Epcam* | 17075 | 4072 |
| 24 | *Epha4* | 13838 | 2043 |
| 25 | *Espn* | 56226 | 83715 |
| 26 | *F2rl1* | 14063 | 2150 |
| 27 | *Fermt1* | 241639 | 55612 |
| 28 | *Frem2* | 242022 | 341640 |
| 29 | *Gja5* | 14613 | 2702 |
| 30 | *Gnb5* | 14697 | 10681 |
| 31 | *Gpr126* | 215798 | 57211 |
| 32 | *Gprc5a* | 232431 | 9052 |
| 33 | *Gprc5b* | 64297 | 51704 |
| 34 | *Hmcn1* | 545370 | 83872 |
| 35 | *Il17rb* | 50905 | 55540 |
| 36 | *Ildr1* | 106347 | 286676 |
| 37 | *Itga6* | 16403 | 3655 |
| 38 | *Itgb8* | 320910 | 3696 |
| 39 | *Jam2* | 67374 | 58494 |
| 40 | *Kcne3* | 100044693 | 10008 |
| 41 | *Kcne3* | 57442 | 10008 |
| 42 | *Kcnma1* | 16531 | 3778 |
| 43 | *Krt19* | 16669 | 3880 |
| 44 | *Mal* | 17153 | 4118 |
| 45 | *Mapk8ip1* | 19099 | 9479 |
| 46 | *Mfge8* | 17304 | 4240 |
| 47 | *Mfi2* | 30060 | 4241 |
| 48 | *Ntrk2* | 18212 | 4915 |
| 49 | *Ppl* | 19041 | 5493 |
| 50 | *Prom1* | 19126 | 8842 |
| 51 | *Rab27b* | 80718 | 5874 |
| 52 | *Reck* | 631094 | 8434 |

TABLE 3-continued

HybHP marker genes for isolation of HybHP cells, that are located on the plasma membrane, and that are upregulated in HybHP compared to cHP. Bold italics text (numbered 1-64 in the first column) reflects genes that are also expressed in ductal cells.

|  | Mouse gene name | Mouse Entrez gene ID | Human Entrez gene ID |
|---|---|---|---|
| 53 | *Reck* | 53614 | 8434 |
| 54 | *Rgma* | 244058 | 56963 |
| 55 | *Rtn4* | 68585 | 57142 |
| 56 | *Scn2a1* | 110876 | #N/A |
| 57 | *Shroom3* | 27428 | 57619 |
| 58 | *Slc5a1* | 20537 | 6523 |
| 59 | *Src* | 20779 | 6714 |
| 60 | *Sstr2* | 20606 | 6752 |
| 61 | *St14* | 19143 | 6768 |
| 62 | *Steap2* | 74051 | 261729 |
| 63 | *Tmem45a* | 56277 | 55076 |
| 64 | *Vwf* | 22371 | 7450 |
| 65 | Aqp4 | 11829 | 361 |
| 66 | Arhgap10 | 78514 | 79658 |
| 67 | Atp4a | 11944 | 495 |
| 68 | Clic5 | 224796 | 53405 |
| 69 | Cyp2f2 | 13107 | #N/A |
| 70 | Efna3 | 100046031 | 1944 |
| 71 | Efna3 | 13638 | 1944 |
| 72 | Hsd17b6 | 27400 | 8630 |
| 73 | Mrgpre | 244238 | 116534 |
| 74 | Ncam2 | 17968 | 4685 |
| 75 | Ptges | 64292 | 9536 |
| 76 | Sulf2 | 72043 | 55959 |
| 77 | Xirp1 | 22437 | 165904 |
| 78 | From | mouse | human |
| 79 | Abcc5 | 27416 | 10057 |
| 80 | Ano1 | 101772 | 55107 |
| 81 | Anxa13 | 69787 | 312 |
| 82 | App | 11820 | 351 |
| 83 | Atp1b1 | 11931 | 481 |
| 84 | Bcam | 57278 | 4059 |
| 85 | Cd200 | 100048780 | 4345 |
| 86 | Cd200 | 17470 | 4345 |
| 87 | Cd24a | 12484 | #N/A |
| 88 | Cd63 | 12512 | 967 |
| 89 | Cdh1 | 12550 | 999 |
| 90 | Celsr1 | 12614 | 9620 |
| 91 | Chrm3 | 12671 | 1131 |
| 92 | Chrnb1 | 11443 | 1140 |
| 93 | Cldn6 | 54419 | 284620 |
| 94 | Cldn7 | 53624 | 1366 |
| 95 | Cttnbp2 | 30785 | 83992 |
| 96 | Ddr1 | 12305 | 780 |
| 97 | Ednrb | 13618 | 1910 |
| 98 | Egflam | 268780 | 133584 |
| 99 | Ehd2 | 259300 | 30846 |
| 100 | Enah | 13800 | 55740 |
| 101 | Epcam | 17075 | 4072 |
| 102 | Epha4 | 13838 | 2043 |
| 103 | Espn | 56226 | 83715 |
| 104 | F2rl1 | 14063 | 2150 |
| 105 | Fermt1 | 241639 | 55612 |
| 106 | Frem2 | 242022 | 341640 |
| 107 | Gja5 | 14613 | 2702 |
| 108 | Gnb5 | 14697 | 10681 |
| 109 | Gpr126 | 215798 | 57211 |
| 110 | Gprc5a | 232431 | 9052 |
| 111 | Gprc5b | 64297 | 51704 |
| 112 | Hmcn1 | 545370 | 83872 |
| 113 | Il17rb | 50905 | 55540 |
| 114 | Ildr1 | 106347 | 286676 |
| 115 | Itga6 | 16403 | 3655 |
| 116 | Itgb8 | 320910 | 3696 |
| 117 | Jam2 | 67374 | 58494 |
| 118 | Kcne3 | 100044693 | 10008 |
| 119 | Kcne3 | 57442 | 10008 |
| 120 | Kcnma1 | 16531 | 3778 |
| 121 | Krt19 | 16669 | 3880 |
| 122 | Mal | 17153 | 4118 |
| 123 | Mapk8ip1 | 19099 | 9479 |
| 124 | Mfge8 | 17304 | 4240 |
| 125 | Mfi2 | 30060 | 4241 |
| 126 | Ntrk2 | 18212 | 4915 |
| 127 | Ppl | 19041 | 5493 |
| 128 | Prom1 | 19126 | 8842 |
| 129 | Rab27b | 80718 | 5874 |
| 130 | Reck | 631094 | 8434 |
| 131 | Reck | 53614 | 8434 |
| 132 | Rgma | 244058 | 56963 |
| 133 | Rtn4 | 68585 | 57142 |
| 134 | Scn2a1 | 110876 | #N/A |
| 135 | Shroom3 | 27428 | 57619 |
| 136 | Slc5a1 | 20537 | 6523 |
| 137 | Src | 20779 | 6714 |
| 138 | Sstr2 | 20606 | 6752 |
| 139 | St14 | 19143 | 6768 |
| 140 | Steap2 | 74051 | 261729 |
| 141 | Tmem45a | 56277 | 55076 |
| 142 | Vwf | 22371 | 7450 |
| 143 | Aqp4 | 11829 | 361 |
| 144 | Arhgap10 | 78514 | 79658 |
| 145 | Atp4a | 11944 | 495 |
| 146 | Clic5 | 224796 | 53405 |
| 147 | Cyp2f2 | 13107 | #N/A |
| 148 | Efna3 | 100046031 | 1944 |
| 149 | Efna3 | 13638 | 1944 |
| 150 | Hsd17b6 | 27400 | 8630 |
| 151 | Mrgpre | 244238 | 116534 |
| 152 | Ncam2 | 17968 | 4685 |
| 153 | Ptges | 64292 | 9536 |
| 154 | Sulf2 | 72043 | 55959 |
| 155 | Xirp1 | 22437 | 165904 |

In some embodiments, the second protein marker of conventional hepatocyte (cHP) cells is overexpressed in the HybHP cells compared to conventional hepatocyte (cHP) cells. Such overexpressed second proteins are encoded by one or more gene shown in Table 1 and Table 3. In an alternative embodiment, the second protein marker of conventional hepatocyte (cHP) cells is underexpressed in the HybHP cells compared to conventional hepatocyte (cHP) cells. Such underexpressed second proteins are encoded by one or more gene as shown in Table 2.

In some embodiments, the step of isolating the first antibody-HybHP cell-second antibody conjugate from the single-cell suspension comprises fluorescence-activated cell sorting (FACS).

In a second approach, purifying a hepatocyte (HybHP) cell (and/or a population of hepatocyte (HybHP) cells) from a mammalian liver, comprises a) preparing a single-cell suspension from the liver, b) substantially removing ductal cells from the single-cell suspension to obtain a first population of cells that contains conventional hepatocyte (cHP) cells and HybHP cells, and c) combining the first population of cells with at least one first antibody that specifically binds to a first protein marker of liver ductal (DC) cells, wherein the combining is under conditions for specific binding of the at least one first antibody to the first protein marker, and wherein the specific binding produces a first composition that comprises a first-antibody-HybHP cell conjugate, and d) isolating the first antibody-HybHP cell conjugate from the first population of cells, thereby producing a second population of cells that comprises a purified HybHP cell (and/or a purified population of HybHP cell).

In one embodiment, the "isolating" step may be achieved using a second antibody that specifically binds to the one or both of the first antibody-second antibody.

In a further embodiment, removal of ductal cells can be done based on the differences in physical properties (such as size/granularity) of ductal cells on the one hand, and conventional hepatocyte (cHP) cells and HybHP on the other hand, by for example differential centrifugation (Example 1; FIG. 5).

C) Methods for In Vitro Culture of HybHP Cells

The invention provides a method for propagating mammalian hybrid hepatocyte (HybHP) cells in vitro, comprising a) combining purified mammalian HybHP cells with culture medium that is suitable for in vitro growth of liver ductal (DC) cells, to produce a first culture composition, b) incubating the first culture composition in vitro under conditions for growth of liver ductal (DC) cells, thereby propagating the HybHP cells. This method is exemplified in Example 8 and FIG. 16.

Several culture methods are known for in vitro propagation of DC cells, including the use of matrigel (Example 8, FIG. 16) as well as other methods described in the art (Huch et al. "Long-term culture of genome-stable bipotent stem cells from adult human liver," Cell. (2015) 160(1-2):299-312; Huch et al., "In vitro expansion of single Lgr5+ liver stem cells induced by Wnt-driven regeneration," Nature. (2013) 494(7436):247-50; and Kamiya et al., "Enrichment and clonal culture of progenitor cells during mouse postnatal liver development in mice," Gastroenterology (2009) 137 (3):1114-26).

In some embodiments, the step of combining purified mammalian HybHP cells with culture medium that is suitable for in vitro growth of liver ductal (DC) cells comprises introducing the purified HybHP cells into a three-dimensional matrix (e.g., matrigel) (Example 8 and FIG. 16). Preferably, incubation is under conditions for producing organoids.

D) Methods for Repopulating the Liver and Treating Liver Damage

The invention further provides methods for successfully transplanting the isolated and/or ex vivo propagated HybHP cells into a mammalian subject for repair of liver damage.

Currently, hepatocytes can be derived from iPSCs, however, this procedure does not generate fully functioning hepatocytes. Other approaches use ductal cells, which also does not generate fully functional hepatocytes. The inventors have overcome these issues by utilizing these newly discovered HybHP cells. Hybrid hepatocytes (HybHP) are morphologically similar to conventional hepatocytes but also express the bile duct gene expression program. These cells can repopulate a diseased mouse liver more efficiently than conventional hepatocytes. Unlike conventional hepatocytes, the HybHP can be efficiently grown in vitro with a ductal phenotype and expanded indefinitely. Later, these cells can be reverted to the hepatocyte phenotype for transplantation.

Thus in one embodiment, the invention provides a method for repopulating the liver of a mammalian host subject in need thereof, comprising transplanting purified hybrid hepatocyte (HybHP) cells into the host subject to produce a treated subject that comprises the purified hybrid hepatocyte (HybHP) cells, wherein the transplanting is under conditions for repopulating the liver of the host subject.

The terms liver "repopulation" and "regeneration" by a given cell type (e.g., HybHP cell) interchangeably refer to the proliferation (i.e., increase in number) of the given cell type in a recipient liver, and to its differentiation into other progeny cell types, such as into conventional hepatocyte (cHP) cells and liver ductal (DC) cells. Liver repopulation is assessed by methods disclosed herein, such as using two-dimensional histological sections to measure the relative area covered by HybHP derived cells compared with the total area of hepatocytes (Example 5, FIG. 6). Other methods for measuring liver repopulation are known in the art, such as measuring the levels of human serum albumin (HSA), immunostaining of liver sections, flow cytometry, and/or polymerase chain reaction (PCR).

In one embodiment, liver "repopulation" is at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, and/or 90%. For example 40% repopulation by donor HybHP cells following transplantation of a host liver means that 40% of the total number of hepatocytes are derived from the donor HybHP, and 60% of the total number of hepatocytes are from the host liver. Methods for measuring the level of liver repopulation are known in the art including (Zhu et al., Nature (2014) 508(7494):93-7; Huch et al., Nature (2013) 494(7436):247-50; and Huch et al., Cell (2015) 160:299-312).

While not intending to limit the invention to any particular degree of liver repopulation, in one embodiment, in one preferred embodiment, repopulation is at least 20%. Data herein demonstrate, in each of three independent mouse models, that HybHP show higher regenerative capacity than normal hepatocytes and are far superior to oval cells (Example 2, Example 3, and Example 5). For example, data herein demonstrate a 13 fold proliferation by HybHP cells following transplantation, which resulted in 65% repopulation of the liver.

Also, data herein show that upon in vivo transplantation of HybHP cells, the transplanted HybHP cells differentiate into and/or revert to progeny hepatocytes that repopulate a host liver by 50% after 3 months following transplantation of 45,000 of the HybHP cells into a mammalian host (Example 2, Example 3, Example 5, FIG. 6). This surprising degree of liver repopulation contrasts with the prior art's inefficient use of Pluripotent Stem Cells (iPSCs) and ductal cells for repopulating the liver. For example, transplantation of 1 million iPSCs resulted in only a 2% repopulation after 9 months (Zhu et al. (2014)). Similarly, 500,000-800,000 ductal cells reached only 1% of repopulation after 2-3 month and none of the animals survived (Huch et al. (2013); and Huch et al. (2015)).

While not intending to limit the invention to any particular degree of liver proliferation, in one embodiment, repopulating comprises at least 10 fold proliferation of the HybHP cells. Data herein demonstrate a 13 fold proliferation by HybHP cells following transplantation, which resulted in 65% repopulation of the liver.

"Proliferation" of a given cell type (e.g., HybHP) after a particular treatment (e.g., following transplantation) refer to an increase in the number of the given cell type (e.g., HybHP cell) and/or the number of its progeny cell types (e.g., cHP cells and liver DC cells) after the particular treatment compared to prior to the particular treatment. In one embodiment, "proliferation" of HybHP cell results in at least 2 fold, 3 fold, 4 fold, 5 fold, 6 fold, 7 fold, 8 fold, 9 fold, 10 fold, 11 fold, 12 fold, 13 fold, 14 fold, 15 fold, 16 fold, 17 fold, 18 fold, 19 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 51 fold, 52 fold, 53 fold, 54 fold, 55 fold, 56 fold, 57 fold, 58 fold, 59 fold, 60 fold, 61 fold, 62 fold, 63 fold, 64 fold, 65 fold, 66 fold, 67 fold, 68 fold, 69 fold, 70 fold, 71 fold, 72 fold, 73 fold, 74 fold, 75 fold, 76 fold, 77 fold, 78 fold, 79 fold, 80 fold, 81 fold, 82 fold, 83 fold, 84 fold, 85 fold, 86 fold, 87 fold, 88 fold, 89 fold, 90 fold, 91 fold, 92 fold, 93 fold, 94 fold, 95 fold, 96 fold, 97 fold, 98 fold, 99 fold, and/or 100 fold increase in the number of HybHP cells and/or of its progeny cHP cells and/or of its progeny liver DC cells. Data herein demonstrate a 13 fold proliferation by HybHP cells following transplantation, which resulted in 65% repopulation of the liver.

The invention's methods are useful wherein the host subject has liver damage.

In one embodiment, liver repopulation by HybHP and its progeny treats the liver damage in the treated subject compared to the host subject. Data herein demonstrate that after transplantation of 14,000-50,000 HybHP cells, much less than the 500,000-1,000,000 cells commonly used in such studies, all HybHP transplanted animals were still alive compared to the death of 90% of control animals and of 50% of cHP-transplanted mice (Example 5; FIG. 6E).

"Liver damage" refers to one or more undesirable change in the structure (e.g., fibrosis) and/or synthetic function and/or metabolic function of liver cells and/or liver tissue. Symptoms of liver damage may be assessed by, for example, biopsy and histology, and blood tests to determine relevant enzyme levels or circulating antigen or antibody, and imaging tests (e.g., to detect a decrease in the growth rate or size of hepatocellular carcinoma). For example, liver damage may be determined by assays of enzymes involved in metabolism (e.g., aspartate aminotransferase (AST), alanine aminotransferase (ALT), alkaline phosphatase, 5' Nucleotidase, gamma-glutamyl transpeptidase (GGT)), proteins involved in normal blood clotting (e.g., prothrombin time (PT) using international normalized ratio (INR) and/or partial thromboplastin time (PTT)), and/or assays of albumin and/or bilirubin. Liver damage is exemplified by liver disease and liver injury.

"Liver disease" refers to a disorder of one or more of the liver functions. Some of the "symptoms" (i.e., signs) of liver disease include fatigue, flu-like symptoms, dark urine, pale stool, abdominal pain, loss of appetite, unexplained weight loss, and/or yellow skin and eyes (which may be signs of jaundice). Liver disease includes chronic liver diseases (such as cirrhosis and non-alcoholic steatohepatitis (NASH)), hepatocellular carcinoma (HCC), liver inflammation, fibrosis, and hepatitis.

"Cirrhosis" (also known as "hepatic; fibrosis") is a chronic disease of the liver marked by degeneration of cells, inflammation, and fibrous thickening of tissue. It is typically a result of alcoholism or hepatitis. Cirrhosis has also been increasingly defined by clinical outcomes. In this context, cirrhosis is distinguished between compensated and decompensated stages, with different features, prognoses and predictors of death. Within the compensated stage, two subpopulations have been identified based on the absence or presence of varices, each of which confers a distinct prognosis. Decompensated cirrhosis is defined by the development of clinically evident complications of portal hypertension (ascites, variceal hemorrhage, hepatic encephalopathy) or liver insufficiency (jaundice). The decompensated stage can be subclassified further into a more severe stage defined by the development of recurrent variceal hemorrhage, refractory ascites, hyponatremia and/or hepatorenal syndrome.

"Non-alcoholic steatohepatitis" ("NASH") is a chronic disease of the liver that develops in patients who are not alcoholic and is characterized by liver inflammation and damage caused by a buildup of fat in the liver, and is histologically indistinguishable from alcoholic hepatitis. NASH can get worse and cause scarring of the liver, which leads to cirrhosis. Laboratory findings of NASH include elevations in aminotransferase levels.

"Hepatocellular carcinoma" ("HCC"), also called "malignant hepatoma," is the most common type of liver cancer. Most cases of HCC are secondary to either a viral hepatitis infection (hepatitis B or C) or cirrhosis. Hepatocellular carcinoma may present with yellow skin, bloating from fluid in the abdomen, easy bruising from blood clotting abnormalities, loss of appetite, unintentional weight loss, abdominal pain especially in the right upper quadrant, nausea, vomiting, or feeling tired.

"Liver inflammation" is a reaction that occurs when liver cells are attacked by a disease-causing microbe (e.g., hepatitis A, hepatitis B, hepatitis C, hepatitis D, and hepatitis E), substance (e.g., alcohol), or autoimmune disorder.

Liver "fibrosis" is the excessive accumulation of extracellular matrix proteins including collagen that occurs in most types of chronic liver diseases. Advanced liver fibrosis results in cirrhosis, liver failure, and portal hypertension.

"Hepatitis" is a disease of the liver characterized by the presence of inflammatory cells in the tissue of the organ. Hepatitis may occur without symptoms, but can lead to jaundice (a yellow discoloration of the skin, mucous membranes, and conjunctiva of the eyes), poor appetite, and fatigue. Depending on the cause, hepatitis can manifest either as an acute or as a chronic disease. Worldwide, viral hepatitis (e.g., hepatitis A, hepatitis B, hepatitis C, hepatitis D, and hepatitis E) is the most common cause, followed closely by alcoholic liver disease and non-alcoholic liver disease (NAFLD). Other less common causes of hepatitis include autoimmune diseases, ingestion of toxic substances, certain medications (such as paracetamol), some industrial organic solvents, and plants.

"Liver injury" refers to mechanical and/or functional damage to liver tissue. The liver can be damaged as a result of impact (for example, a motor vehicle crash), penetrating trauma (such as a knife or gunshot wound), and/or exposure to chemicals, drugs, etc. Injuries may range from relatively small collections of blood (hematomas) within the liver to large tears that go deep into the liver. Because the liver has many large blood vessels, the main problem resulting from liver injury is severe bleeding, particularly within the abdominal cavity. Subjects with liver injury and severe bleeding have symptoms of shock, including a rapid heart rate, rapid breathing, and cold, clammy, pale or bluish skin. Subjects also have abdominal pain and tenderness because blood in the abdomen irritates the abdominal tissue. When bleeding is severe, the abdomen may also be swollen. Liver injury may be diagnosed by computed tomography (CT), ultrasonography, and/or surgery to determine the extent of the injury and to stop the bleeding.

While not intending to limit the type of donor subject that provides the source of the purified HybHP, and without limiting the type of host subject receiving the purified and/or in vitro cultured HybHP cells, in one embodiment, the host subject and the donor subject are different individuals, such as in heterologous liver cell therapy. In another embodiment, the host subject and the donor subject are the same individual (such as in heterologous liver cell therapy).

In some embodiments, the HybHP cells are transgenic. "Transgenic" and "genetically engineered" cell refer to a cell whose genome has been manipulated by any molecular biological technique, including, for example, the introduction of a transgene, homologous recombination, knockin of a gene, and/or knockout of a gene. The term "transgene" as used herein refers to any nucleic acid sequence which is introduced into the cell by experimental manipulations. A transgene may be an "endogenous DNA sequence" that is present in the cell in nature, or a "heterologous DNA sequence" (also referred to as "foreign DNA") that is not present in the cell in nature (including gene sequences that are found in that cell and that further contain some modification (e.g., a point mutation, the presence of a selectable marker gene, etc.) relative to the naturally-occurring gene). For example, the transgene may be a marker to facilitate detection of the transgenic HybHP cells and/or its progeny. Alternatively, the transgene may be a therapeutic gene whose expression treats liver damage.

In one embodiment, repopulating the liver does not produce hepatocellular carcinoma (HCC), i.e., the liver of the treated subject lacks HCC. In a further embodiment, the HybHP cells are purified and/or propagated in vitro prior to the transplanting.

The term "transplanting" refers to introducing cells of interest (e.g., HybHP cells) into a tissue of a host subject. Transplanting may be accomplished by intrasplenic injection, injection into the portal vein, direct intrahepatic injection, and/or injection into lymph nodes.

Thus, the invention provides therapeutic methods for the treatment of liver damage. In one embodiment, the invention provides a method for treating one or more of liver damage in a mammalian host subject in need thereof, comprising transplanting a therapeutically effective amount of purified hybrid hepatocyte (HybHP) cells into the host subject to produce a treated subject, wherein the transplanting is under conditions for repopulating the liver of the host subject, thereby treating the one or more of the liver damage.

Data herein demonstrate that HybHP with their high repopulation potential are ideal candidates for liver repair. Data herein demonstrate that after transplantation of 14,000-50,000 HybHP cells, much less than the 500,000-1,000,000 cells commonly used in such studies, all HybHP transplanted animals were still alive compared to the death of 90% of control animals and of 50% of cHP-transplanted mice (Example 5; FIG. 6E).

EXPERIMENTAL

The following examples serve to illustrate certain preferred embodiments and aspects of the present invention and are not to be construed as limiting the scope thereof.

Example 1

Experimental Procedures
Mice

Mouse studies were performed in accordance with NIH guidelines for the use and care of laboratory animals and approved by the UCSD Institutional Animal Care and Use Committee, 500218. Sox9-Cre$^{ERT2}$ mice were generated as described (Kopp et al., 2011). For the current study, we utilized a founder that induces recombination in cells expressing high and low levels of Sox9 and exhibits higher recombination efficiency than the founder described in Kopp et al. (2011). In contrast to the previously reported founder, the founder used in this study displays low levels of recombination in the absence of tamoxifen. Sox9-Cre$^{ERT2}$ mice were backcrossed to C57Bl/6 mice for at least 8 generations. R26R$^{YFP}$ (Jax 006148), R26R$^{tdTomato}$ (Jax 007909), MUP-uPA (Weglarz et al., 2000), Ck19Cre$^{ERT}$ and Ttr-Cre$^{ERT}$ and Alb-Cre$^{ERT}$ (Schuler et al., 2004) mice were also maintained in the C57Bl/6 background. NZG (Jax 012429) mice were maintained in the FBV background and all experiments involving this line were in 50% FBV-057Bl/6 background. In all experiments at least 3 mice were included per experimental group.

Tamoxifen (Sigma-Aldrich) was dissolved in corn oil and injected subcutaneously (s.c.). Mice were fed with 0.1% DDC (Sigma-Aldrich) in LabDiet #5015 (Testdiet) for 6 weeks. Mice were fed with a choline-deficient diet (MP Biomedicals) supplemented with 0.15% ethionine (CDE) in drinking water (MP Biomedicals) for 3 weeks. CCl$_4$ (Sigma) was dissolved at 1:3 (25%) in corn oil and i.p. injected at 2 μl/gr or dissolved 1:2 (50%) and injected at 2 μl/gr for the acute model. HFD was composed of 59% fat, 15% protein, and 26% carbohydrates based on caloric content (BioServ).

The STAM model of NASH-driven HCC was established as previously described (Fujii et al., 2013). Briefly, 2-day-old male mice were (s.c.) injected with 200 μg streptozotocin (Sigma), and then fed with HFD (Bio-Serv) beginning at 4 weeks of age. NASH-driven HCC in MUP-uPA mice was previously described (Nakagawa et al., 2014). DEN induced HCC was also described (Maeda et al., 2005).

Adenovirus and AAV Vectors

Recombinant adenovirus expressing FLP-recombinase (Ad-Flpo, Vector Biolabs #1775) was expanded and prepared at the Vector Core Developmental Lab at UCSD. Ad-Flpo was diluted in PBS and intravenously injected to mice (1×10^9 plaque-forming units/mouse). AAV-TBG-FLPo was obtained from Vector Biolabs (#1728) and diluted in PBS and intravenously injected to mice (5×10^11 genome copies/mouse).

Immunofluorescence and Immunohistochemical Analysis

Mice were intra-cardial perfused with Zn-Formalin (Polysciences) and excised livers further fixed o.n. in Zn-Formalin. Livers were washed with PBS and incubated for 2 hrs with 100 mM Tris pH 9.4-10 mM DTT. Livers were washed stepwise with PBS-15% and 30% sucrose at 4° C. embedded in Tissue Tek OCT compound (Sakura Finetek) and frozen. Tissue blocks were cut with a cryostat to 8 μm sections. Slides were washed in PBS and antigen retrieval was performed with citrate pH6 buffer at 96° C. for 1 hr. After cooling and washing the slides with PBS, they were incubated with PBS-0.1% Triton-X-100 for 20 min. After extensive washing with PBS, the slides were blocked with PBS-0.1% Tween-2% Donkey serum for 30 min. Antibodies were diluted in the same blocking buffer and incubated at 4° C. o.n. Slides were washed 3 times with PBS-0.1% Tween and incubated with corresponding secondary antibodies diluted in blocking solution for 2 hrs, followed by 3×PBS-0.1% Tween and 2×PBS washes. Slides were washed further with deionized water and 70% ethanol prior to incubation with 0.1% Sudan Black (Sigma) in 70% ethanol for 20-30 min. Extensive washing with PBS-0.2% Tween was performed before incubating the slides with DAPI for nuclear staining and mounting with Mowiol. Imaging was performed with a Zeiss Axioimager2 and Hamamatsu Nanozoomer. Images were processed using Zeiss ZEN and NDPview software.

Antibodies used were: chicken α-GFP (Abcam #ab13970), 1:200 for YFP and 1:1250 for GFP. Rabbit α-Sox9 (Santa Cruz #sc-20095) 1:50. Goat α-Opn (R&D

AF808) 1:100. Goat α-Ck19 (Santa Cruz #sc-33111), 1:100. Mouse α-Lacz (Promega #Z3781), 1:50. Goat HNF-4α (Santa Cruz #sc-6556), 1:50. Mouse α-GS (BD #610517), 1:50. Rabbit α-Ki67 (Gentex #GTX16667), 1:50. Rabbit α-FAH (AbboMax #602-910), 1:200. Alexafluor fluorescent antibodies (Molecular Probes, Invitrogen), 1:800. Donkey Alexa-488 α-Chicken (Jackson), 1:800.

For tyramide amplification signal (TSA), Life Technologies T-20925 kit was used following manufacturer instructions. Antibodies used with TSA were rabbit α-Sox9 (Millipore #5535), 1:20,000. Goat α-Opn (R&D #AF808) 1:2000. Rabbit α-Agxt2l1 (Sigma #HPA044546), 1:1000. Goat α-Aqp4 (Santa Cruz #sc-9888), 1:10000.

Normal human liver paraffin sections were stained with rabbit α-Sox9 (Millipore #5535), 1:100 and Goat α-Opn (R&D #AF1433) 1:100. ImmPRESS-AP Anti-Rabbit Ig (alkaline phosphatase) Polymer Detection Kit and Immpact VECTOR Red Alkaline Phosphatase (AP) Substrate Kit were used for Sox9. ImmPRESS HRP Anti-Goat Ig (Peroxidase) Polymer Detection Kit and ImmPACT NovaRED Peroxidase (HRP) Substrate were used for Opn.

Quantification of HybHP Labeling Efficiency

To estimate the number of HybHP cells in the unchallenged liver, sections from Sox9-GFP mice livers were stained with GFP and β-Catenin antibodies to delineate the boundaries of hepatocytes. Stained slides including at least 4 lobes were scanned with Nanozoomer and for each slide 7-9 areas ranging from 0.05 to 0.25 mm$^2$ were drawn. Hepatocytes contained in the areas were manually quantified Linear regression was then used to model the relationship between area and number of hepatocytes. We observed substantial variability in estimates of hepatocyte number obtained when applying models built from different slides (estimates were up to 20% different) suggesting that models did not generalize across slides. Thus we applied this procedure independently to every slide quantified. In all cases area explained most of the variability in hepatocyte count with $R^2 > 0.98$. In parallel, different areas ranging from 4 to 10 mm$^2$ were drawn from the same slides. Areas corresponding to CV and PV empty spaces were subtracted from the total area and the total number of hepatocytes was estimated using the slide-specific regression models. The number of HybHP (GFP$^+$) within these larger areas was counted manually. The same procedure was repeated in Sox9-Cre$^{ERT}$; R26R$^{YFP}$ mice treated with 100 mg/kg of tamoxifen. The labeling efficiency, estimated by the ratio between labeled HybHP (YFP$^+$) and total HybHP (GFP$^+$) estimated in Sox9-GFP mice was 51%.

Clarity

Whole livers from Zn-Formalin perfused Sox9-Cre$^{ERT}$; R26R$^{tdTomato}$ mice were isolated and incubated in a polyacrylamide hydrogel solution as previously described (Chung et al., 2013, Yang et al., 2014) for 1 week. Samples were embedded in a polymerized hydrogel by raising the temperature to 37° C. for 3 hours, and clarified by incubating in a solution of 4% Sodium Dodecyl Sulfate (SDS, Amresco) in Sodium Borate buffer (200 mM, pH 8.5, Sigma) at 37° C. for 2-3 weeks, followed by washing for 2 days in PBS+0.1% Triton X-100 (PBST, Sigma). Individual lobes were isolated and stained with anti-CK19 antibody (TROMAIII Developmental Studies Hybridoma Bank) at 1:100 dilution in PBST, washed in PBST 4 times, and stained in donkey anti-rat secondary antibody (Jackson Immunoresearch) at 1:100 dilution in PBST, washed in PBST plus DAPI (1:5000 dilution), and incubated in FocusClear (CelExplorer) prior to imaging.

For imaging, samples were incubated in FocusClear mounted on coverglass-bottom dishes (Wilco) as previously described (Chung et al., 2013) and visualized with a single-photon excitation scanning confocal microscope system (Olympus), using a 10×, 0.60NA, 3 mm WD water-immersion objective (Olympus). Images were taken with z-step size of 1 um and reconstructed using Imaris software (Bitplane).

Liver Perfusion, Flow Cytometry and Cell Sorting

For flow cytometry analysis, liver single cell suspensions were isolated by two step collagenase digestion and differential centrifugation. Single cell suspensions were analyzed using HNF-4α (Santa Cruz #sc-6556) and CK19 (TROMAIII Developmental Studies Hybridoma Bank) antibodies. Donkey anti-goat alexa-647 and donkey anti-goat alexa-405 (Molecular Probes, Invitrogen) were used as secondary antibodies. For intracellular staining Transcription Factor Staining Kit (BD Biosciences) was used. Fixable Viability Dye eFlour® 780 Dye or eFlour® 506 were used for exclusion of dead cells (eBioscience). Samples were measured on a CyAn™ ADP flow cytometer (Beckman Coulter, USA) and analyzed with FlowJo.8 software (Tree Star, USA) or a BD Influx for cell sorting.

RNA Extraction, Sequencing and Data Analysis

Sorted cells were pelleted and lysed with Trizol. Extracted aqueous phase was then purified with RNAeasy microkit (Qiagen) following manufacturer instructions. 200 ng of RNA with an RNA Integrity Number (RIN) of 8.5 or greater was used to generate libraries using Illumina's TruSeq Stranded mRNA Sample Prep Kit. The manufacturer's protocol was followed, with the exception that RNA was fragmented for 5 minutes. Libraries were multiplexed and sequenced with 50 basepair (bp) single end reads (SR) to a depth of approximately 20 million reads per sample on an Illumina HiSeq2000 using V3 chemistry.

Fastq files were aligned to the mouse genome (mm9 release) with STAR v2.3.0e (Dobin et al., 2013). Differential gene expression was obtained using the Homer pipeline (Heinz et al., 2010). The analyzeRepeats.pl script was used to obtain integer read counts from the alignments. Read counts were aggregated across exons and condensed at the gene level. Log 2 fold change, p-values and false discovery rates (FDR) for differentially expressed genes were obtained with Homer's getDiffExpression.pl script using the R EdgeR software (Robinson et al., 2010). Genes achieving an FDR less than 0.05 were considered differentially expressed. Gene classes were defined by: 1—HybHP/BD>HP (n=49) and BD>HybHP>HP (n=140). 2—HP/BD>HybHP (n=61); BD>HP>HybHP (n=58) and HP>BD>HybHP (n=2). 3—HybHP>HP/BD (n=42) and HybHP>HP>BD (n=2). 4—HP>HybHP/BD (n=71) and HP>HybHP>BD (n=65). Differentially expressed genes were analyzed with DAVID (Default settings without PIR_Superfamily, SMART, COG Ontology, SP_PIR_KEYWORDS and UP_SEQ_FEATURE) (Huang da et al., 2009a, b) to identify biological processes enriched for each category.

Transplantation

Fah$^{-/-}$ mice (Grompe et al., 1993) were crossed with the Il2rg$^{-/-}$ (B6.129S4-Il2rgtm1Wjl/J) mice from the Jackson Laboratory and Rag2$^{-/-}$ mice (RagN12) from Taconic Farms. Genotyping was done with the same primers and conditions as described elsewhere (Grompe et al., 1993) or according to the protocols provided by vendors. Mice were kept on 7.5 mg/ml NTBC (100%) via drinking water. Mice were kept in temperature- and humidity-controlled animal quarters with a 12-hr light-dark cycle.

Adult mice were transplanted as previously described (Ponder et al., 1991). Mice were anesthetized with isoflurane and kept on a heating pad during the whole procedure. Then a mid-abdominal incision was performed and the spleen was prepared for injection. The lower pole of the spleen was injected with the three different cell types—oval cells, cHP and the HybHP re-suspended in DMEM 15% FBS. Closing of the abdominal muscle layer was performed with 4-0 silk sutures, and the skin was stapled. NTBC was immediately withdrawn in a stepwise gradation with each step lasting a day (25%, 12%, 6% and 3% of 7.5 mg/ml colony maintenance concentration). After three weeks of the first cycle, the mice were put back on 100% NTBC containing water (7.5 mg/ml) for one week and then returned to 0% NTBC as described earlier in daily steps. The second cycle on regular water was continued for 4 weeks after which tissues were collected.

For the survival study, animals were intrasplenically transplanted with 14000-40000 of the two cell types HybHP and cHP as described above. The animals went through two cycles of NTBC withdrawal (each comprising of 3 weeks on water followed by one week on NTBC) at the end of which they were maintained only on regular water (starting post-op day 68). The periods on NTBC and on regular water are schematically depicted in the FIG. 6E. Animals were monitored during this period and were euthanized as they approached the clinical end points of the study. The study was terminated roughly 4 months after the transplantation at which point a Kaplan-Meir survival curve was generated.

Example 2

Periportal Hepatocytes with High Regenerative Capacity

Since the portal area may be the organizing center for liver repair, harboring putative stem cell niches (Kuwahara et al., 2008), we aimed to analyze the regenerative capacity of cells in this region using transgenic mice expressing GFP from the Sox9 promoter, which is primarily active in bile duct cells and bipotential hepatobilliary progenitors (Gong et al., 2003). Immunofluorescence (IF) analysis indicated that bile duct cells (CK19$^+$) showed high GFP expression (FIG. 1A,B). However, other cells located in the limiting plate around the bile duct and the portal vein, expressed low amounts of GFP (FIG. 1B,C). These cells were negative for the bile duct marker CK19 (FIG. 1B) and positive for the hepatocyte marker HNF4α (FIG. 1C), suggesting that they are hepatocytes. These periportal hepatocytes comprise 4.53%±0.24% of all hepatocytes (FIG. 1A, based on 7,390 GFP$^+$ hepatocytes out of 163,292 total hepatocytes, n=3). Periportal hepatocytes are present in both males and females throughout their lifetime (FIG. 8A).

Figure 1H:
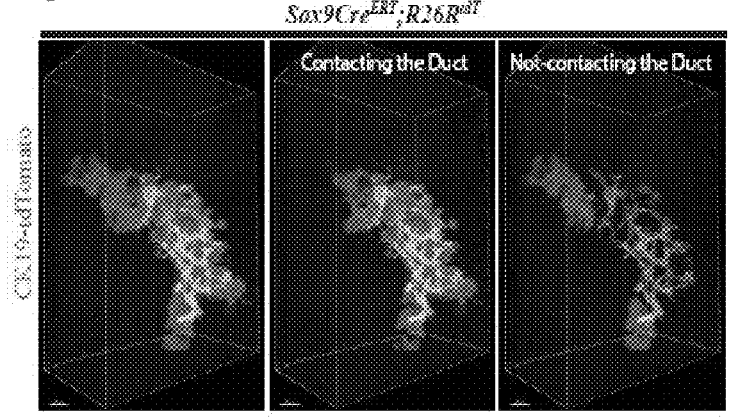

To examine the regenerative and differentiative capacity of Sox9$^+$ periportal hepatocytes and determine whether they differ from other hepatocytes that are Sox9-GFP negative, we used a Sox9-Cre$^{ERT}$ transgenic line suitable for labeling low Sox9 expressing cells (see Experimental Procedures). When expressed in combination with a R26R$^{YFP}$ reporter line and treated with tamoxifen, the Cre$^{ERT}$ protein enters the nucleus and excises the STOP cassette that prevents YFP expression only in Sox9 expressing cells. Once recombination occurs, the cell and its progeny are permanently YFP labeled. In Sox9-Cre$^{ERT}$; R26R$^{YFP}$ mice, some ductal cells (CK19$^+$ HNF4α$^-$) were labeled with YFP prior to tamoxifen administration (FIG. 1D), suggesting leaky Cre$^{ERT}$ nuclear translocation in high Sox9 expressing cells. Importantly, however, almost no hepatocytes (CK19$^-$ HNF4α$^+$) were YFP$^+$ in the absence of tamoxifen (FIG. 1D; 1427 CK19$^+$/ YFP$^+$ out of 1434 YFP$^+$ cells, n=2). YFP-labeled CK19$^-$ HNF4α$^+$ periportal hepatocytes appeared after a single 5 mg/kg tamoxifen dose at P10 (FIG. 1E), but their number increased after 100 mg/kg tamoxifen treatment, resulting in labeling of 2.3%±0.15% of total hepatocytes with an estimated efficiency of 51.4% (FIG. 1F; 4,968 YFP$^+$ hepatocytes out of 217,975 hepatocytes, n=3), mirroring what was observed with the Sox9-GFP transgene (FIGS. 1A-C) and inconsistent with the Sox9 expression pattern in WT mice given high doses of tamoxifen (Carpentier et al., 2011). The labelling efficiency for ductal cells with a single 100 mg/kg tamoxifen injection at P10 was 95.4% (FIG. 1F, 5,321/5,577 cells, n=3). The age at which mice were tamoxifen-treated did not affect the number of YFP$^+$ periportal hepatocytes, whose population remained stable for at least 9 months (FIG. 8B). Given that these periportal hepatocytes display elevated basal Sox9 promoter activity and other ductal markers (see below), we named them Hybrid Hepatocytes (HybHP). To determine the exact location of HybHP within the portal tract and relative to the canals of Hering, we performed CLARITY analysis (Chung et al., 2013). Since the endogenous Sox9-GFP and R26R$^{YFP}$ fluorescent signals were too dim, we chose R26tdTomato due to its brightness (FIG. 8C). Clarified livers from tamoxifen-treated Sox9-Cre$^{ERT}$; R26R$^{tdTomato}$ mice were stained with CK19 antibody to delineate the ductal tree and imaged. HybHP were found to wrap around the portal vein and contact the intricate mesh formed by the bile ducts and their terminal branches, which form the canals of Hering (FIGS. 1G and 8D). Interestingly, HybHP were not exclusively attached to bile duct cells (FIG. 1H).

Figure 9A:
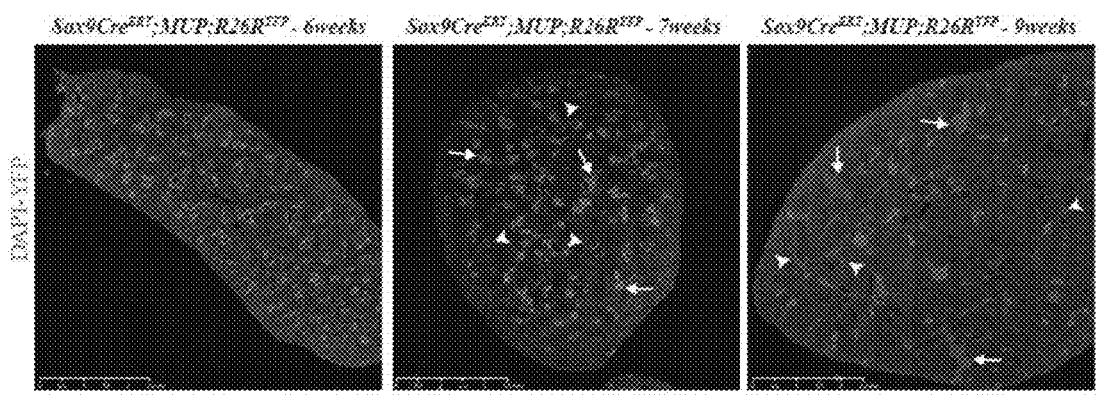
FIG. 9. New hepatocytes generated from HybHP acquire metabolic zonation after expansion. Related to FIG. 2. (A) Whole slide scans of liver sections from tamoxifen treated Sox9-Cre$^{ERT}$; MUP; R26R$^{YFP}$ mice at 6, 7 and 9 weeks of age stained with GFP antibodies (green). Arrows indicate expanding HybHP clones whereas arrowheads indicate portal tracts devoid of HybHP but with an oval cell response. (B) Immunostaining for YFP (green) and glutamine synthetase (GS, red) of liver sections from the Sox9-Cre$^{ERT}$; R26R$^{YFP}$; MUP-uPA tamoxifen treated mice shown in FIG.
Figure 9B:
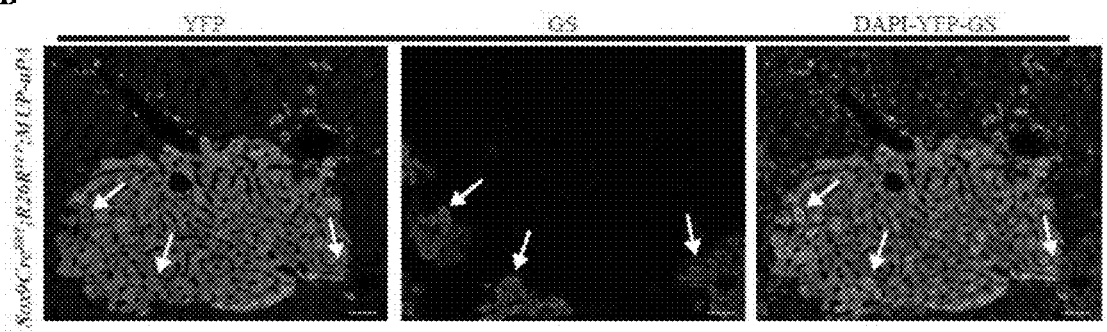
Figure 9C:
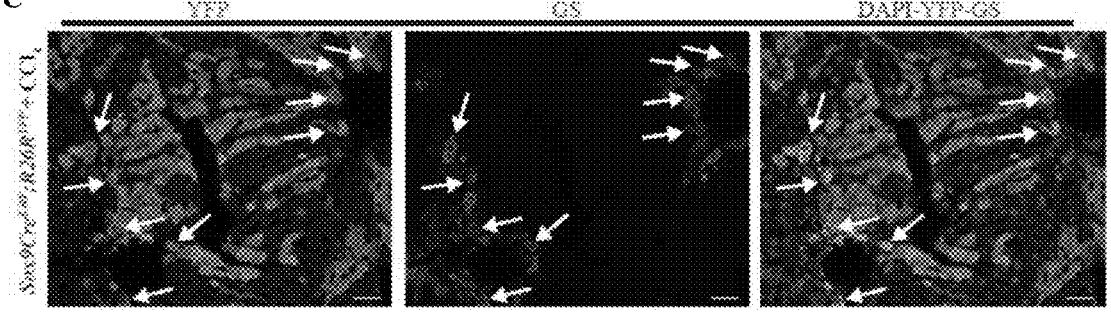

Next, we analyzed the behavior of YFP$^+$ HybHP during the regeneration period that follows different types of liver injury. First, we examined MUP-uPA transgenic mice, which undergo liver damage due to ER stress induced by expression of urokinase-type plasminogen activator (uPA) in hepatocytes (Nakagawa et al., 2014b; Weglarz et al., 2000). MUP-uPA mice first display liver damage at 3 weeks of age, and after peaking at 5 weeks the damage dissipates by 13 weeks (Weglarz et al., 2000). Without tamoxifen treatment, 99.9% YFP$^+$ cells were also CK19$^+$ in 9 weeks old Sox9-Cre$^{ERT}$; MUP-uPA; R26R$^{YFP}$ mice (6 weeks after damage onset; FIG. 2A, 4,838 CK19$^+$/YFP$^+$ cells out of 4,842 YFP$^+$ cells, n=3), suggesting that neither ductal nor oval cells produce new hepatocytes in this model. However, after administration of 100 mg/kg tamoxifen at P10, YFP$^+$ HybHP showed a strong contribution to newly produced hepatocytes, forming clones that expanded out of all portal areas and represented 20% of hepatocytes at 5-6 weeks of age (FIGS. 2B and 9A). In mice analyzed 5-6 weeks later, numerous YFP$^+$ labeled clones had disappeared and were replaced by ductular reactions, but the surviving clones were larger and contained approximately 200 hepatocytes each (FIGS. 2C and 9A). Expanding YFP$^+$ hepatocytes that reached the central vein expressed glutamine synthetase (GS), a marker of zone 3 hepatocytes, indicating that HybHP produce fully differentiated and functional hepatocytes, whose metabolic profile matches their location along the portal-central axis (FIG. 9B).

We also used repetitive CCl$_4$ administration which causes pericentral damage that eventually gives rise to fibrosis (Wong et al., 1998) as an independent model of chronic liver injury. No oval cell expansion takes place and new hepatocytes are not derived from ductal cells in this model (Español-Suñer et al., 2012; Grompe, 2014; Rodrigo-Torres et al., 2014; Tarlow et al., 2014a; Yanger et al., 2014). After twice-weekly CCl$_4$ administration for 6 weeks, 34.5%±2.2 of hepatocytes in Sox9-Cre$^{ERT}$; R26R$^{YFP}$ mice previously treated with 100 mg/kg tamoxifen were YFP$^+$, and hence derived from HybHP, with most cells extending along the hepatic cords, from the periportal region to the central vein (FIG. 2D; 5,213 YFP$^+$ out of 14,947 total hepatocytes from 41 independent areas, n=2). Given an estimated labeling efficiency of 52.8%, the contribution of HybHP to new hepatocytes is 65.4%. Littermates not receiving CCl$_4$ did not show YFP$^+$ HybHP expansion (FIG. 2E), while acute CCl$_4$ treatment produced minor HybHP expansion (FIG. 2F; 10,654 HybHP out of 239,888 total hepatocytes, or 8.3%, n=3). Newly labeled hepatocytes reaching the central vein after chronic CCl$_4$ challenge, expressed GS (FIG. 9C) as observed in the MUP-uPA model.

We confirmed the contribution of HybHP to newly produced hepatocytes using an independent genetic tool. We reasoned that by labeling hepatocytes sparsely, we could compare the clonal behavior of HybHP to that of parenchymal hepatocytes. We found that the TTR-Cre$^{ERT}$ driver (Tannour-Louet et al., 2002) can be used to randomly label hepatocytes in undamaged liver (FIG. 10A,D). In TTR-Cre$^{ERT}$; R26R$^{YFP}$; MUP-uPA mice treated with 100 mg/kg tamoxifen at P10 and analyzed 4 weeks later, some labeled hepatocytes produced proliferative YFP$^+$ clones, but most of the original YFP$^+$ hepatocytes were eliminated by ongoing liver damage (FIG. 10B). Nonetheless, some clones of YFP$^+$ hepatocytes appeared at the portal area and increased in size with time, confirming what was seen with the Sox9-Cre$^{ERT}$ driver (FIG. 10C). We also subjected TTR-Cre$^{ER}$; R26R$^{YFP}$ mice to chronic CCl$_4$ treatment. The observed pattern of expanding clones with some contacting the portal tract was consistent with our previous observations (FIG. 10E,F). The absence of new hepatocytes derived from oval cells in MUP-uPA mice was confirmed using the CK19-Cre$^{ERT}$ driver, which specifically labels bile duct and oval cells (Means et al., 2008) (FIG. 11A,B; 1,333 CK19$^+$/YFP$^+$ out of 1,333 YFP$^+$ cells, n=3).

Example 3

Clonally Labeled HybHP Produce New Hepatocytes and Transdifferentiate into Duct Cells To further examine the role of HybHP in regeneration after chronic liver damage, we used a system in which only HybHP are specifically and clonally labeled without a strict dependence on tamoxifen. We crossed Sox9-Cre$^{ERT}$ and NZG mice (Yamamoto et al., 2009), which contain a loxP-flanked STOP cassette upstream of a nuclear targeted LacZ marker as well as a downstream GFP marker whose expression is prevented by the LacZ cassette, which is flanked by Frt sites (FIG. 3A). Tamoxifen administration to heterozygous mice labeled Sox9-expressing cells (duct cells and HybHP) with nuclear LacZ (FIG. 3B). To specifically label HybHP we took advantage of the fact that adenovirus (Nakagawa et al., 2014a) or AAV-TBG only target hepatocytes (Yanger et al., 2013). Infection of Sox9-Cre$^{ERT}$; NZG mice, previously treated with tamoxifen, with either adenoviruses or AAV expressing FLPo recombinase that excises the LacZ cassette, resulted in GFP labeling of some HybHP (FIG. 3C) that were all CK19$^-$ (551 cells, n=3) and HNF4α$^+$ (323 cells, n=3), confirming labeling specificity (FIGS. 3D,E and 4). Three weeks after viral infection and 5 weeks after initial tamoxifen injection, different groups of animals were established to determine the clonal behavior of HybHP after CCl$_4$ treatment. While no response was observed in animals treated with an acute or a single CCl$_4$ dose, in which clones mainly consisting of a single hepatocyte were observed, multicellular clones that expanded from the portal tract were observed after 6 CCl$_4$ doses. After 6 more injections, clones containing >5 hepatocytes were readily detected, with several clones having more than 20 cells (FIG. 3F,G), confirming what was observed with the single reporter system and further establishing the role of HybHP in repopulating the liver after chronic damage.

Biphenotypic hepatocytes expressing ductal markers were reported in different mouse models of cholestatic liver injury (Sekiya and Suzuki, 2014; Tanimizu et al., 2014; Tarlow et al., 2014b; Yanger et al., 2013). These cells are thought to descend from mature hepatocytes during cholestatic liver damage. Virus-mediated hepatocyte labeling or transplantation of labeled hepatocytes into damaged livers (Tanimizu et al., 2014; Tarlow et al., 2014b; Yanger et al., 2013) showed that a few hepatocytes can trans-differentiate into duct cells. Other studies have shown that almost all duct cells arose from biphenotypic hepatocytes (Sekiya and Suzuki, 2014), but another report ruled out transdifferentiation of mature hepatocytes into ductal cells in the same cholestatic injury models (Malato et al., 2011). We reasoned that transdifferentiation of HybHP during cholestatic liver injury may explain the above discrepancy. We tested this possibility with the NZG dual recombinase system that specifically labels HybHP and triggered cholestatic injury with 3,5-dicarbethoxy-1,4-dihydrocollidine (DDC) diet (Preisegger et al., 1999). After 6 weeks of DDC feeding, most labeled HybHP underwent pronounced morphological changes, with cell and nuclear sizes diminished and acquisition of strong expression of Sox9 and the ductal marker osteopontin (Opn) (FIG. 4). Complete loss of the hepatocyte phenotype with undetectable HNF4α expression was observed in 10% of HybHP, 2.5% of which incorporated into bile ducts with strong expression of CK19 (FIG. 4). These results are consistent with reports showing that in cholestatic injuries preexisting ductal cells generate most of the oval cells, but also suggest that a minor proportion of oval cells arise from trans-differentiating HybHP and not from parenchymal biphenotypic hepatocytes as previously reported (Sekiya and Suzuki, 2014). Congruently, we found that tamoxifen-treated Alb-Cre$^{ERT2}$; R26R$^{YFP}$ mice consistently contained YFP$^+$ duct cells in the absence of any damage (FIG. 11C), indicating that the hypothesis that DDC-induced oval cells arise mainly from mature hepatocytes (Sekiya and Suzuki, 2014) should be re-evaluated.

Example 4

HybHP Exhibit a Unique Transcriptome

Figure 5A:
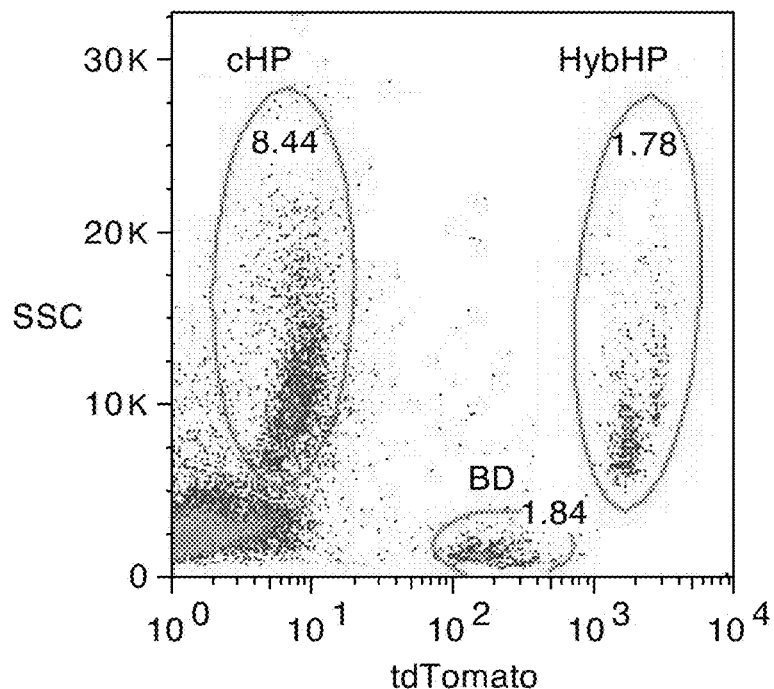
FIG. 5. The HybHP transcriptome confirms their hybrid character. (A) Conventional hepatocytes (cHP), bile duct cells (BD) and Hybrid Hepatocytes (HybHP) from a liver collagenase digest were FACS separated after exclusion of dead cells and cell doublets and gating based on size/granularity (FCS/SSC) and tdTomato expression. (B) Total cellular RNA was extracted (3 independent isolations) and deep sequenced. Shown is a heatmap of genes that were differentially expressed in HybHP relative to cHP. (C) Proportion of genes that are differentially expressed in HybHP vs. cHP that show the same differential expression trend in BD vs. cHP. (D) Normalized expression values (in reads per kilobase per million) of the indicated genes in HybHP, cHP and BD. (E) IF analysis using Tyramide Signal Amplification (TSA) of Sox9-GFP transgenic mouse liver sections stained for Sox9 and Opn. White arrows: HybHP with weak Sox9 and Opn expression. (F) Normal human liver sections stained for Sox9 and Opn. Black arrows: periportal hepatocytes with weak expression of either marker. White arrows: ductal cells. Scale bars, 20 μm.
Figure 5B:
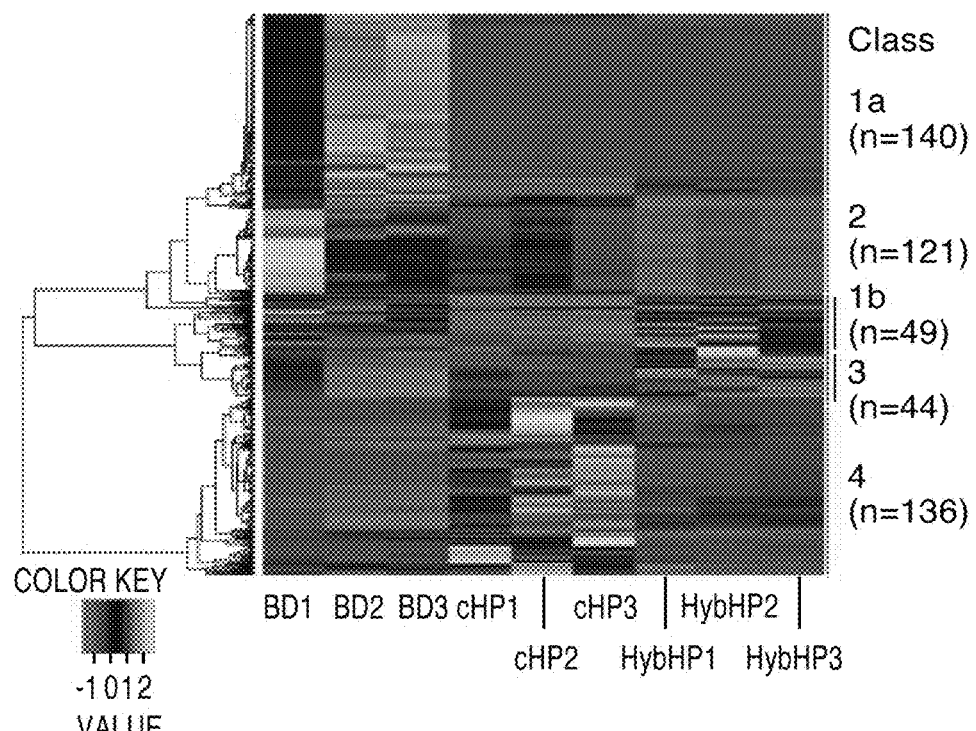
Figure 5C:
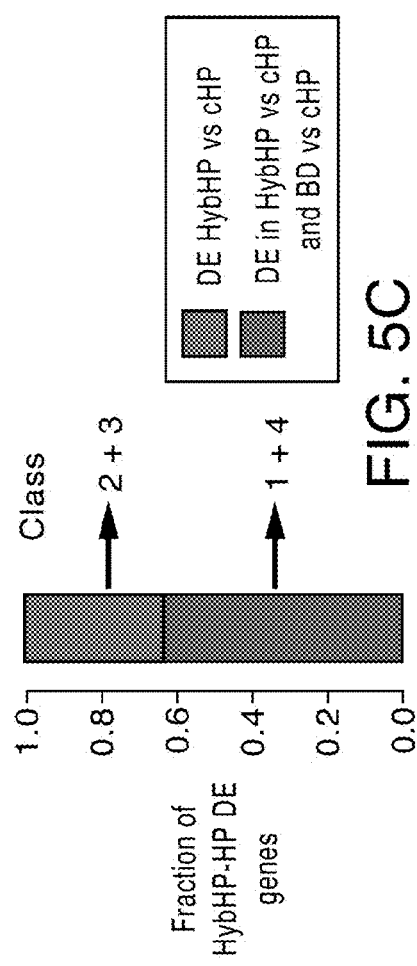
Figure 5D:
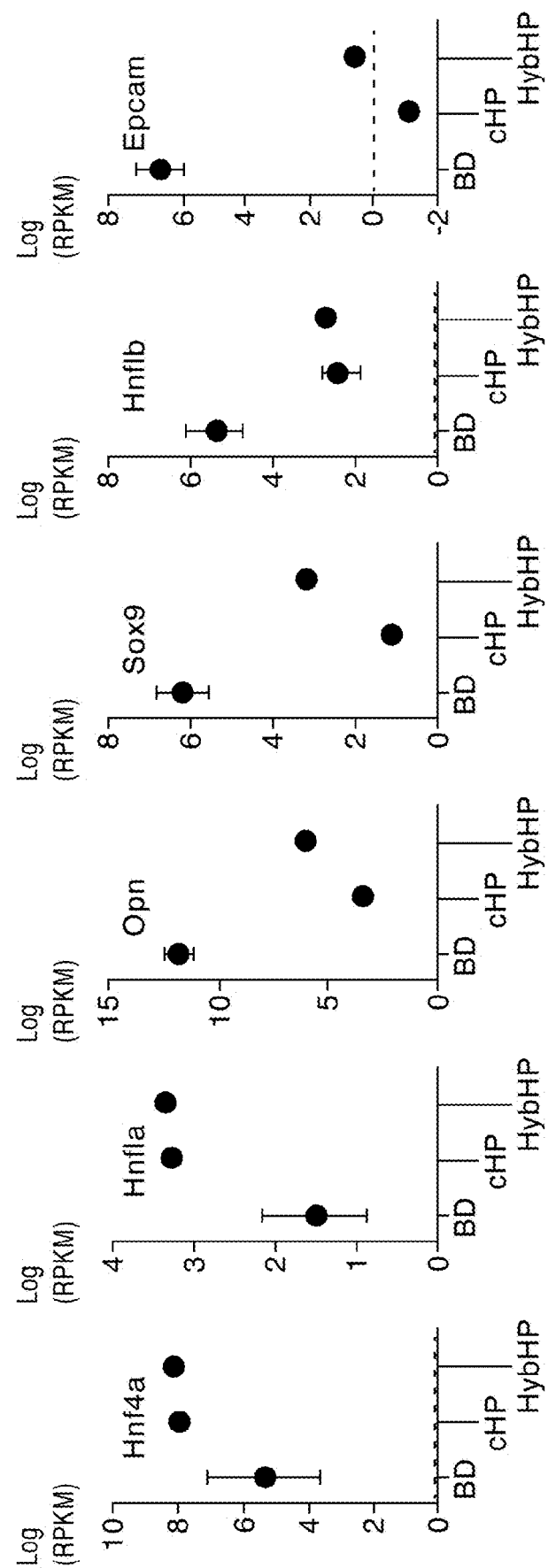
Figure 12A:
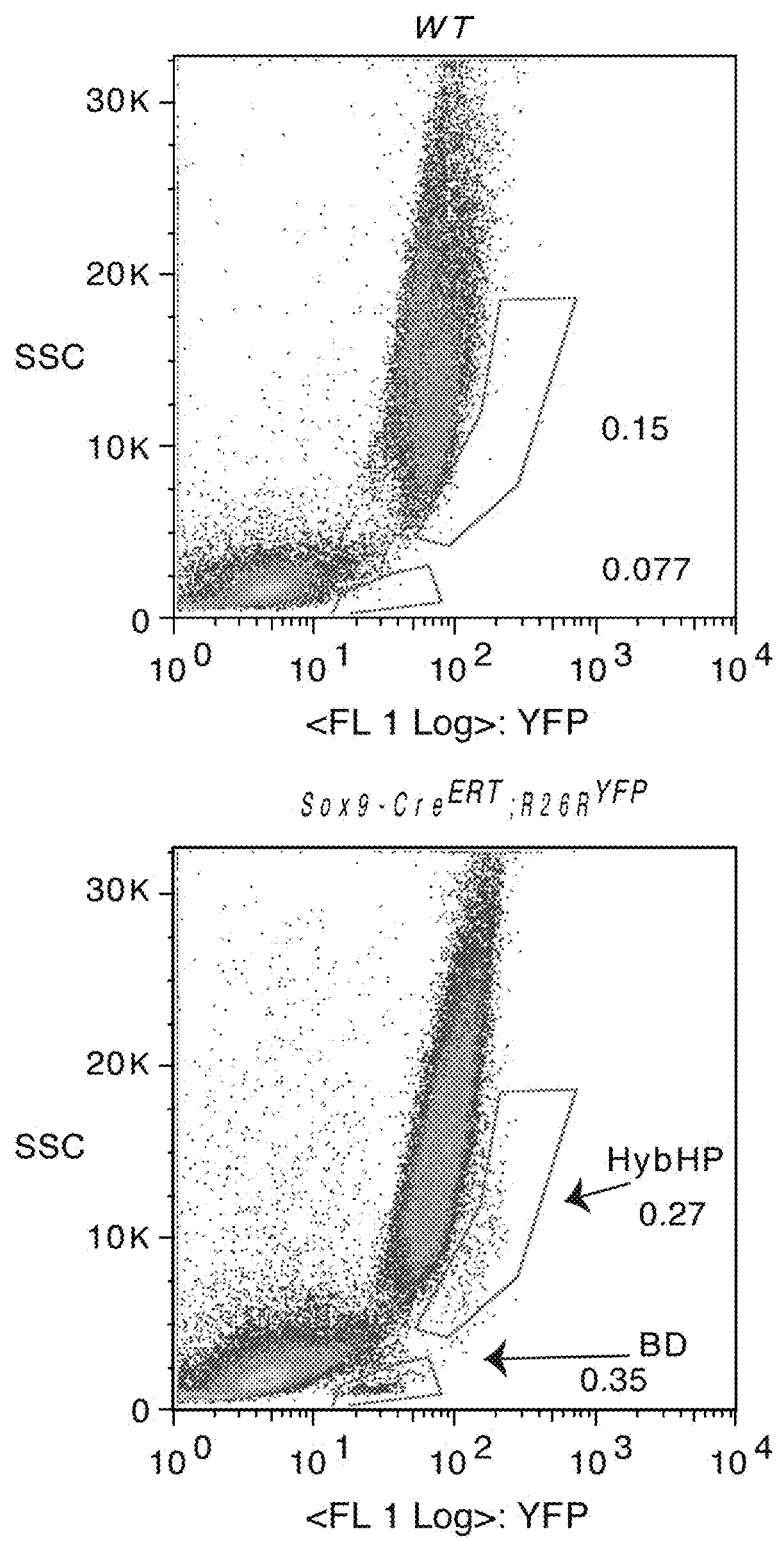
Figure 12B:
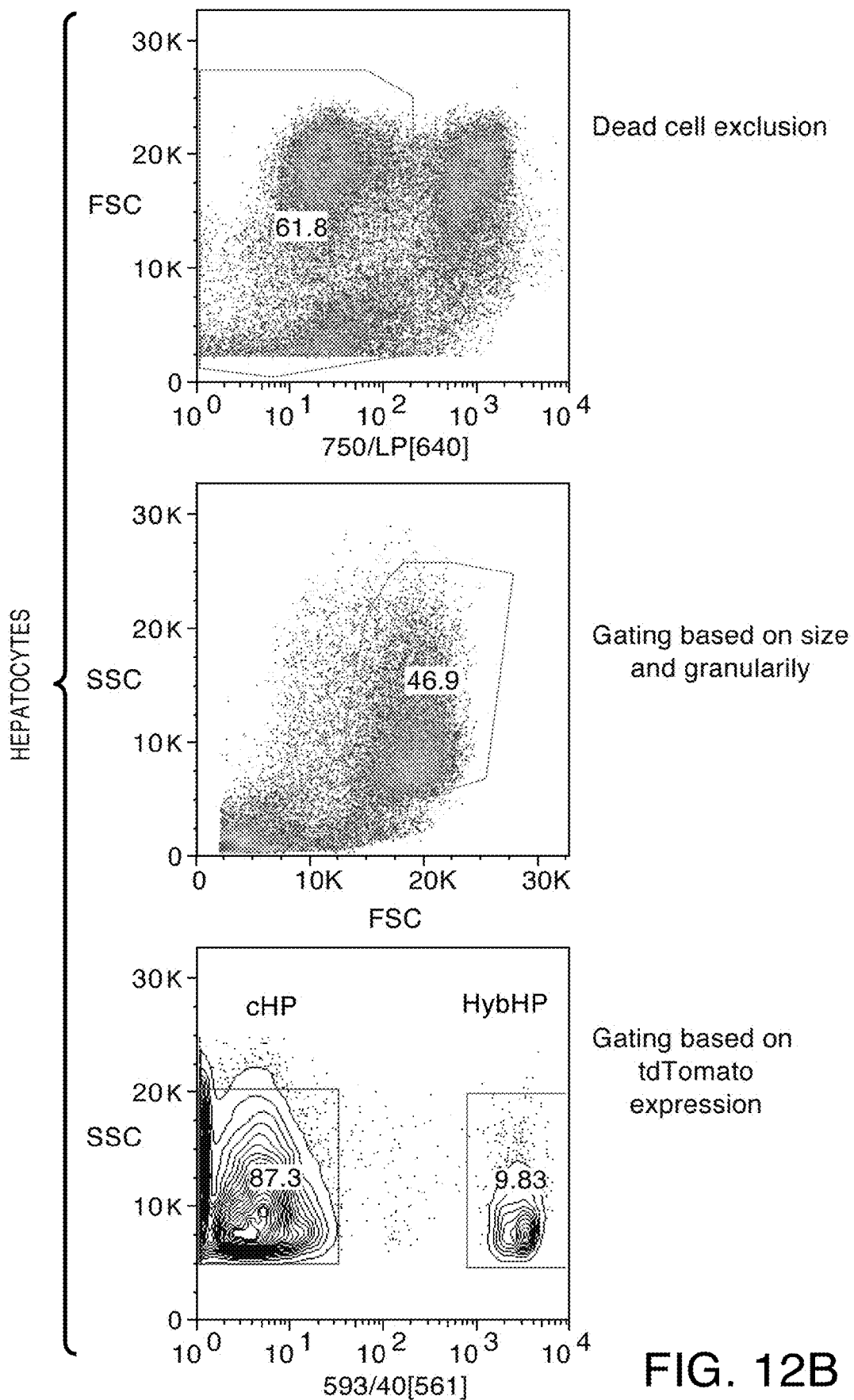
Figure 12C:
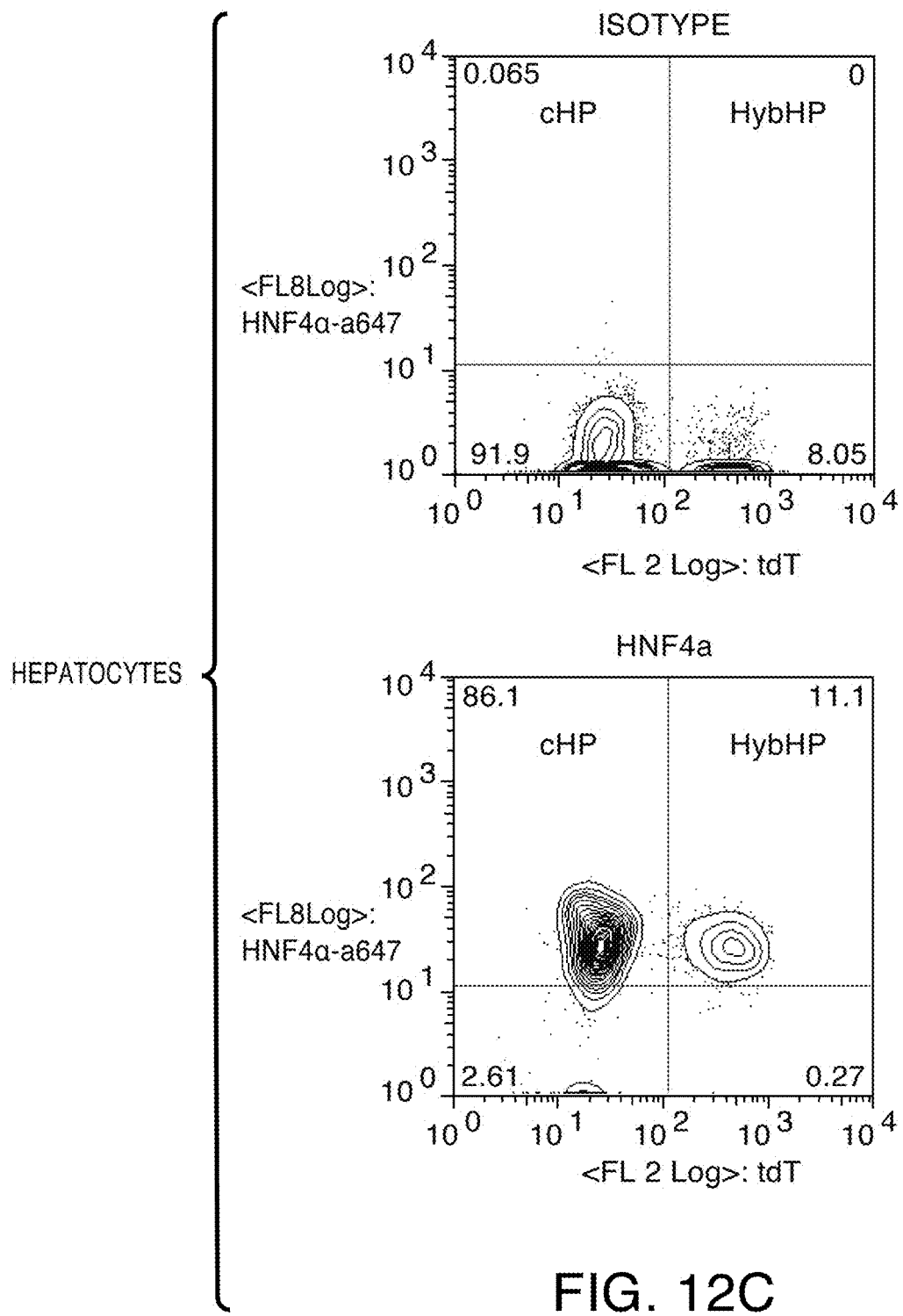
Figure 12D:
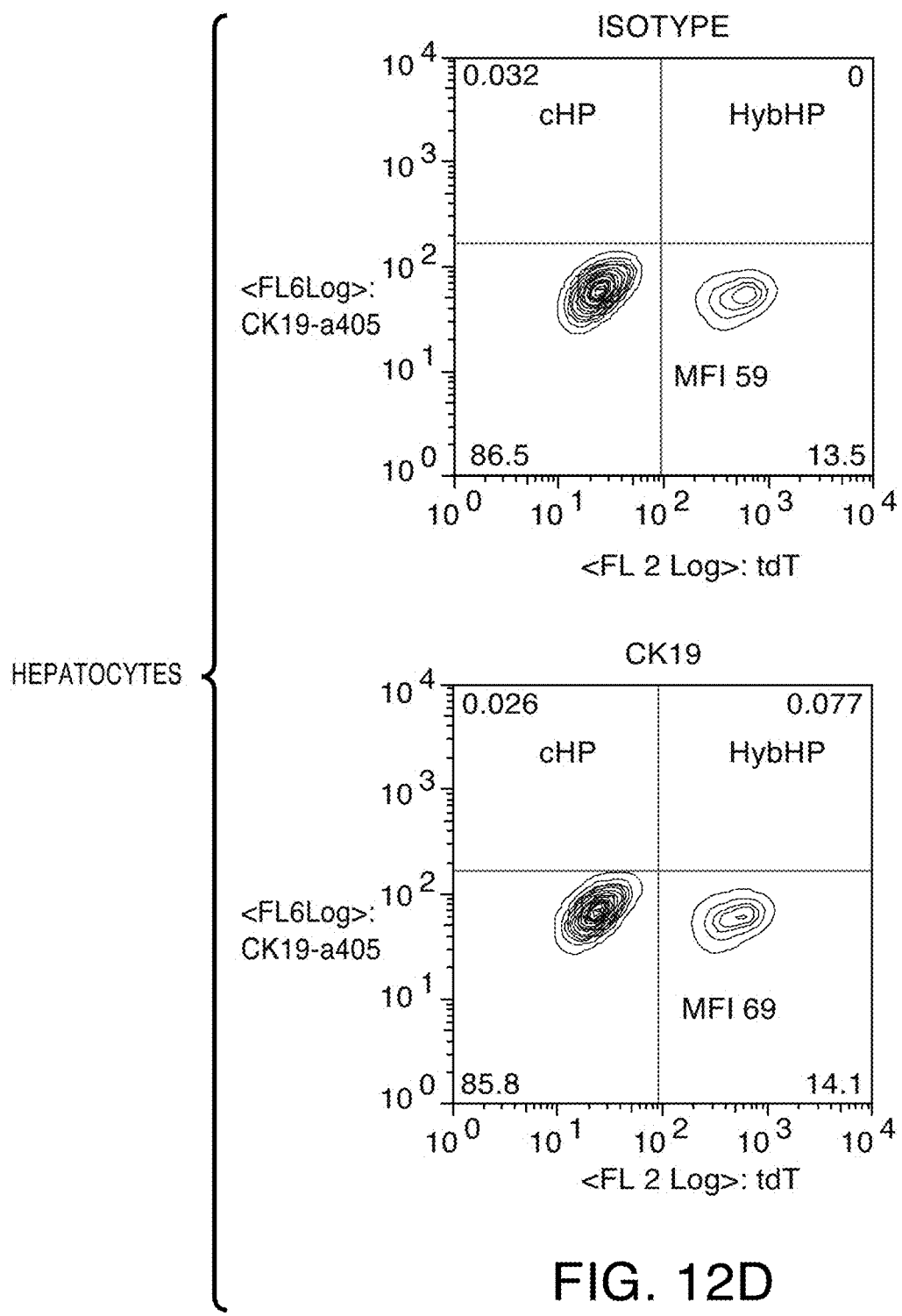
Figure 12E:
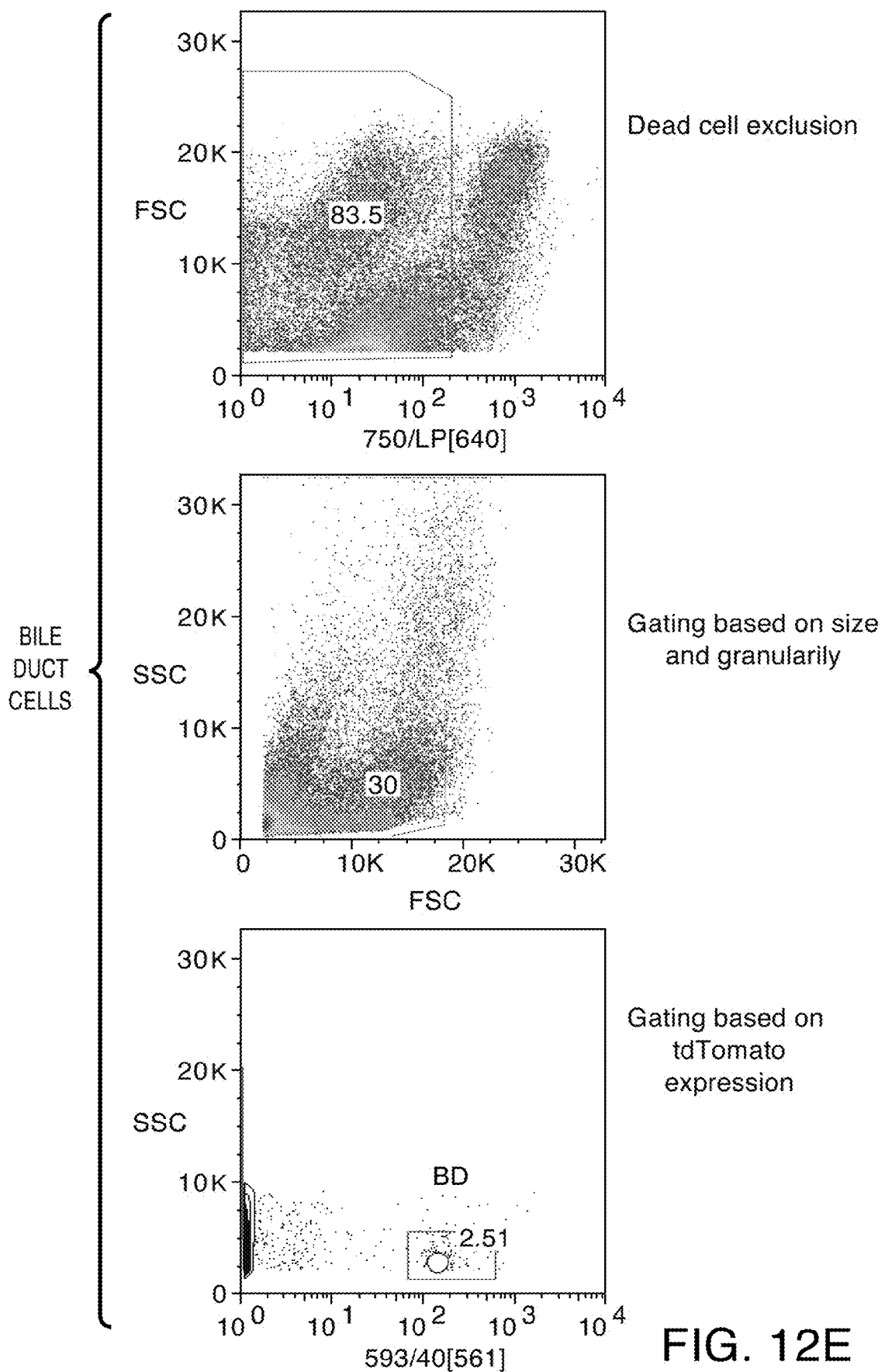
Figure 12F:
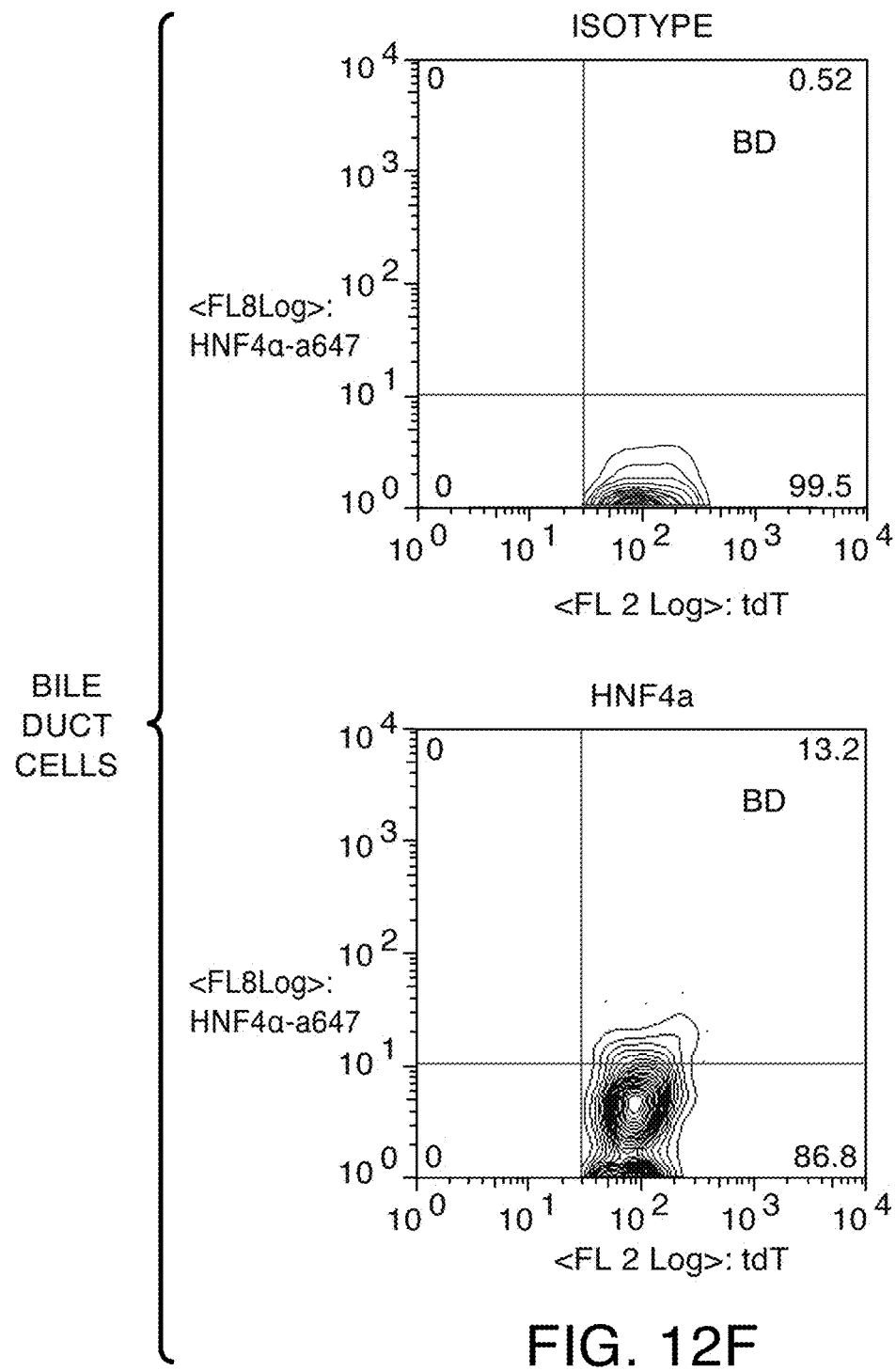
Figure 12G:
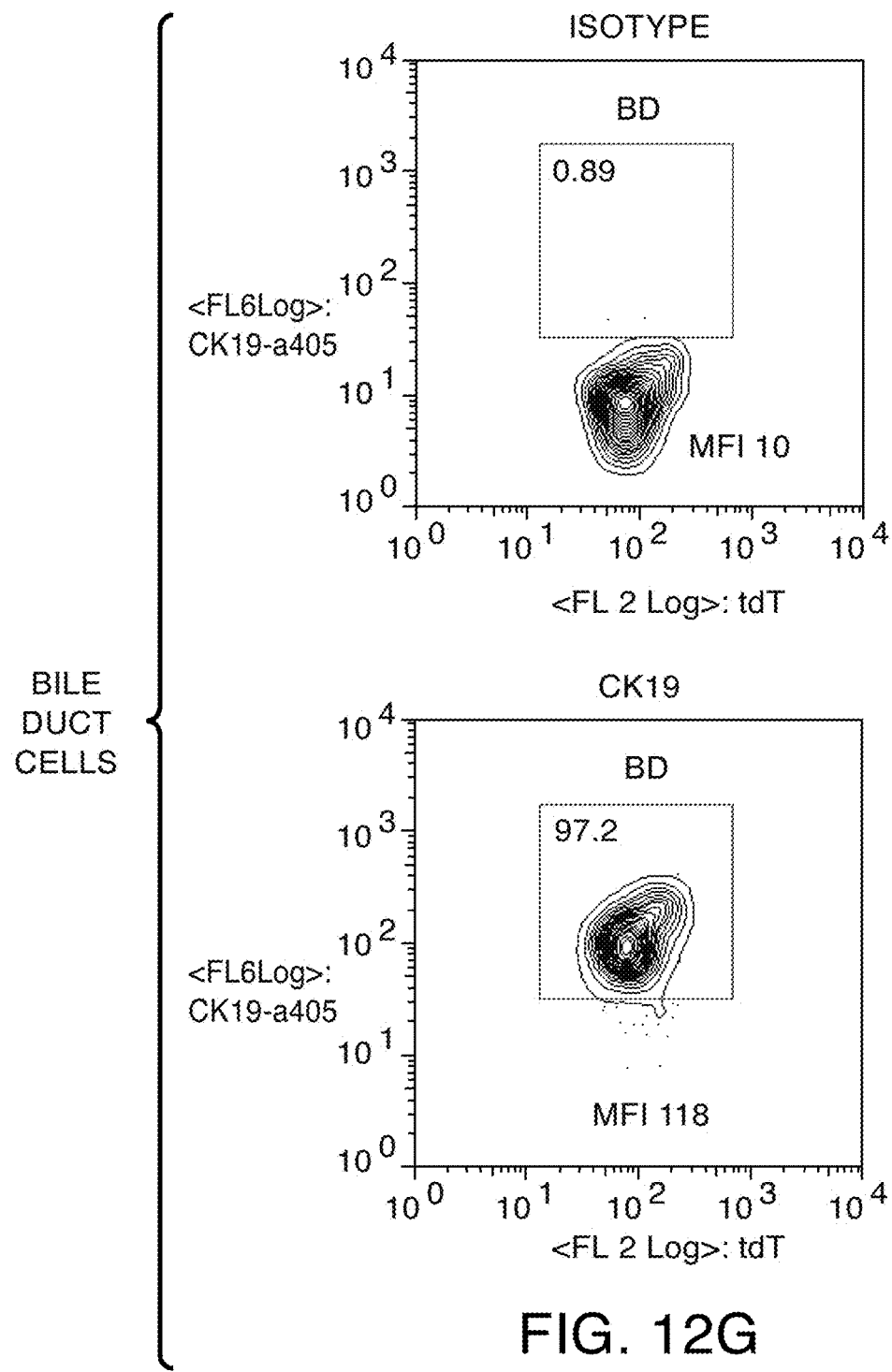

To compare the molecular characteristics of HybHP to those of conventional hepatocytes (cHP) and bile duct cells (BD), we isolated the three populations by sorting collagenase liver digests from tamoxifen (100 mg/kg)-treated Sox9-Cre$^{ERT}$; R26R$^{tdTomato}$ mice given an additional tamoxifen dose (20 mg/kg) 10 days later to maximize HybHP labeling (FIGS. 5A, 8C). Sox9-Cre$^{ERT}$; R26R$^{YFP}$ mice were unsuitable for these experiments because YFP was insufficiently bright to separate labeled cells from autofluorescent unlabeled cells (FIG. 12A). RNA was isolated and subjected to RNAseq analysis. Clustering of samples according to transcript expression data indicated that the HybHP transcriptome was similar to the cHP transcriptome and that both cHP and HybHP differed extensively from BD (FIG. 13A). However, HybHP diverged from cHP by 490 genes, of which 233 were upregulated and 257 were downregulated (FIG. 5B). To rule out that the observed differences are the result of noise, we conducted detailed statistical analysis and found that it was highly unlikely that the differential expression patterns could originate from biological or technical noise (P-value<0.001; Example 7; FIGS. 5 and 15). The 490 genes that were differentially expressed between HybHP and cHP were subdivided into 4 general classes: 1) genes that are upregulated in both HybHP and BD relative to cHP; 2) genes whose expression is lower in HybHP than in cHP or BD; 3) genes whose expression is higher in HybHP than in cHP or BD; and 4) genes that are downregulated in both HybHP and BD relative to cHP (FIG. 5B). Classes 1 and 4, where differential expression relative to cHP follows the same trend in both HybHP and BD, comprise 64% of differentially expressed genes (FIG. 5C). The probability of obtaining such results by mere chance is negligible ($p<10^{-49}$), supporting the notion that HybHP are distinct hepatocytes with some BD characteristics. Inspection of lineage-specific markers confirmed that HybHP express ductal markers, including Sox9 and Opn, which are barely expressed by cHP (FIG. 5D). Coincidentally, major hepatocyte fate determinants, such as HNF1$\alpha$ and HNF4$\alpha$, were equally expressed in HybHP and cHP, but other BD markers such as HNF1$\beta$ and EpCam were hardly upregulated (FIG. 5D). Classification of genes differentially expressed in HybHP versus cHP according to function, revealed that genes belonging to class 1, which are upregulated in both HybHP and BD relative to cHP, are mostly involved in cell adhesion, interactions with the extracellular matrix (ECM) and processes related to morphogenesis and tube formation typical of duct cells (FIG. 13B). The intimate interaction between HybHP and BD in the portal areas at the canals of Hering may require homotypic interactions mediated by such adhesion molecules which are expressed at very low levels in cHP. Immunofluorescence analysis of Sox9-GFP liver sections revealed that HybHP express low levels of Sox9 and Opn (FIG. 5E). Similar signals were detected in liver sections from WT mice (FIG. 13C).

It was previously shown that normal human liver contains periportal hepatocytes with simultaneous HNF4$\alpha$ and HNF1$\beta$ expression (Isse et al., 2013). We also detected hSox9 and hOpn in some periportal hepatocytes in human liver sections (FIG. 5F), suggesting that HybHP also exist in human liver.

Furthermore, we conducted a simulation study to determine whether HybHP-specific signals, could be due to BD contamination. The simulation identified a group of genes with large differences in expression between HybHP and cHP, which are extremely unlikely to have originated from a mixture of BD+cHP (P-value<0.001; Example 7; FIGS. 5 and 15), further supporting the hypothesis that the HybHP signal is specific and that a substantial portion of the differentially expressed genes are BD genes. Class 4 genes, which are downregulated in both HybHP and BD relative to cHP, are mainly involved in oxidative drug metabolism (FIG. 13B). These genes are expressed at high levels in cHP, and their downregulation may explain why HybHP are less sensitive to damage caused by metabolic activation of toxic compounds. For instance, $CCl_4$ is mainly metabolized by Cyp2E, which is expressed in zone 3 hepatocytes, the cells that preferentially succumb to $CCl_4$ injury (Wong et al., 1998). Finally, class 2 and 3 genes are those with the lowest and highest expression in HybHP relative to the other populations, respectively. Class 3 genes did not show enrichment for any specific functional category, suggesting that these genes are involved in many diverse functions. Immunofluorescence analysis of the proteins expressed by 2 such genes, Agxt2l1 and Aqp4, revealed that they are expressed by zone 1 hepatocytes (FIG. 13D). Since our analysis compared HybHP to bulk hepatocytes depleted of HybHP, it should be expected that genes that are highly expressed by zone 1 hepatocytes would appear upregulated in the HybHP population. Intriguingly, class 2 genes exhibit statistically significant enrichment for processes related to adaptive and innate immune responses, as well as inflammatory responses (FIG. 13B), implying that HybHP are less likely to respond to Damage-Associated Molecular Patterns (DAMPs), Pathogen-Associated Molecular Patterns (PAMPs) and other inflammatory stimuli that act on cHP to activate the acute phase response. For this specific class of genes, contamination of cHP with Kupffer cells could lead to their presence in the cHP fraction. Although the purity of cHP is very high (>97%), a small number of $CD45^+$ cells was present in this population (data not shown). Whether this can explain the observed variations in class 2 genes is difficult to assess. However, some of these genes, for instance Tlr5 and Tlr8, are not expressed in Kupffer cells (Lavin et al., 2014). Altogether, these data suggest that the HybHP transcriptome is a hybrid of the HP and BD transcriptomes with a few immune response genes that are downregulated relative to cHP (FIG. 13E).

Example 5

Transplanted HybHP Display High Regenerative Capacity

The high regenerative potential and plasticity of HybHP make them attractive candidates for liver disease cell therapy. We therefore performed transplantation experiments using $Fah^{-/-}$ mice, which due to FAH (fumarylacetoacetate hydrolase) deficiency, undergo spontaneous liver damage upon withdrawal of NTBC (2-nitro-4-trifluoromethylbenzoyl-1,3-cyclo-hexanedione), and if left untreated succumb to fatal liver failure within 1-2 months (Grompe et al., 1995). We isolated HybHP ($tdTomato^+$) and cHP ($tdTomato^-$) from tamoxifen-treated Sox9-$Cre^{ERT}$; $R26R^{tdTomato}$ mice and oval cells ($tdTomato^+$) from CDE diet-fed animals of the same genotype. Although it was reported that DDC-induced oval cells can repopulate the $Fah^{-/-}$ liver (Wang et al., 2003), considering the ability of HybHP to transdifferentiate into duct cells in DDC-fed mice (FIG. 4), it is plausible that in previous studies, HybHP were inadvertently transplanted along with oval cells leading to $Fah^{-/-}$ liver repopulation. We therefore reasoned that CDE diet-induced oval cells are more suitable for such experiments because they are less likely to be contaminated with HybHP. We transplanted 45,000 sorted cells of each type into spleens of $Fah^{-/-}$; $Rag2^{-/-}$; $Il2rg^{-/-}$ recipient mice (Bissig et al., 2007), which were subsequently withdrawn from NTBC for 3 weeks followed by one week on NTBC and 4 more weeks without NTBC. As shown in FIG. 6A, oval cells generated very few $tdTomato^+$ clones, with a scattered tdTomato signal across the liver surface. In clear contrast, HybHP-transplanted mice showed numerous $tdTomato^+$ clones in all liver lobules covering a large part of the surface. Due to higher autofluorescence of cHP relative to the $Fah^{-/-}$ background, we could detect clones derived from these cells by examination of the intact liver, but very few oval cells ($tdTomato^+$) were detected in the transplanted liver. These oval cells retained ductal morphology and were not $FAH^+$ (FIG. 6B). HybHP clones consisted of $FAH^+/tdTomato^+$ hepatocytes, whereas cHP-generated clones were $FAH^+/tdTomato^-$ on the $Fah^{-/-}$ background (FIG. 6B). Surface clonal area measurement showed that HybHP were superior to cHP, generating clones that were 2-times larger, (FIG. 6C upper graph). Measurement of histologic clone areas yielded similar results, with HybHP-generated clones being 2.5-fold larger than cHP-generated clones (FIG. 6C lower graph). Of note, human cirrhotic livers lose metabolic zonation resulting in diffuse GS expression throughout the parenchyma instead of zone 3 restricted expression (Fleming and Wanless, 2013). GS staining of liver sections from HybHP transplanted mice showed that expanding clones exhibit normal zonal expression; few HybHP expressed GS at the central vein and the remaining cells were devoid of GS expression in clear contrast to the surrounding damaged parenchyma (FIG. 6D). These results underscore the higher repopulation potential of HybHP, and as seen in other injury models (FIG. 9B, C), HybHP progeny acquire the correct metabolic profile according to their location along the portal-central axis. To further assess the therapeutic potential of HybHP, we transplanted another cohort of mice for a long term survival study, comparing three independent groups: non-transplanted, cHP and HybHP transplanted. Due to the limited number of HybHP that were available for these experiments, we transplanted 14,000-50,000 cells, much less than the 500,000-1,000,000 cells commonly used in such studies. At the end of the study, we found that all HybHP transplanted animals were still alive when 90% of control animals and more than 50% of cHP-transplanted mice had died, consistent with a higher regenerative capacity with improved survival rate (FIG. 6E).

Example 6

Neither HybHP Nor Oval Cells Give Rise to HCC

In many experimental models of hepatic carcinogenesis, oval cell responses precede the emergence of neoplasia, as has been observed in humans where ductular reactions precede cancer in cirrhotic livers (Roskams, 2006). Such observations led to the suggestion that oval cells could be the origin of a large fraction of liver cancers (Alison et al., 2009). Given the important role of liver damage and compensatory proliferation in liver tumorigenesis (Kuraishy et al., 2011; Maeda et al., 2005), the relationship between cell proliferation and cancer risk (Tomasetti and Vogelstein, 2015) and the high proliferation rate of HybHP during chronic liver injury, we examined the potential contribution of both oval cells and HybHP to hepatic carcinogenesis. We traced HybHPs and oval cells in three independent mouse models of HCC: DEN-induced HCC (Maeda et al., 2005), MUP-uPA mice fed with high fat diet (HFD) (Nakagawa et al., 2014b) and the STAM model of diabetes-promoted HCC (Fujii et al., 2013), using Sox9-Cre$^{ERT}$; R26R$^{YFP}$ mice and the same labeling conditions as above. Whereas DEN is metabolically activated in pericentral/zone 3 hepatocytes and does not induce oval cell expansion, consumption of HFD, which induces liver damage and compensatory proliferation in both MUP-uPA and STAM mice, gives rise to substantial oval cell proliferation (FIG. 14) and is thought to induce a similar course of HCC development as in NASH-driven human HCC. Cell labeling in all 3 cases was conducted prior to induction of any cellular damage or carcinogenic insult using 100 mg/kg tamoxifen (FIG. 7A), which labels HybHP and duct cells with 51% and 95% efficiency, respectively. After searching for YFP$^+$ cells in well-developed tumor nodules and hyperproliferative lesions, no YFP$^+$ neoplastic cells were detected (FIG. 7B-D, n=106 HCC nodules from 9 DEN-treated mice, n=79 HCC nodules in 7 MUP-uPA+HFD mice and n=62 HCC nodules in 5 STAM mice). The corresponding binomial distributions suggest that it is extremely unlikely that HybHP or ductal cells are the exclusive or preferential origins for HCC in these models (p<10E-10). Notably, we computed 95% Credibility Intervals (Beta (1,1) prior distribution) for the expected percentage of HybHP- or ductal cells-derived tumors still compatible with the experimental data obtained. For HybHP, the obtained C.I. (DEN, 0-5.3%; MUP-uPA+HFD, 0-7.2% and STAM, 0-9%) suggest that even if HybHP were considered as a potential source for HCC, the majority of tumors (>91%) would not originate from them. Due to the higher labeling efficiencies for duct cells, the obtained C.I. (DEN, 0-2.8%; MUP-uPA+HFD, 0-3.9% and STAM, 0-4.9%) are even more definitive in ruling out ductal cells as the HCC origin. These results confirm that HCC most likely is derived from differentiated hepatocytes.

Figure 14A:
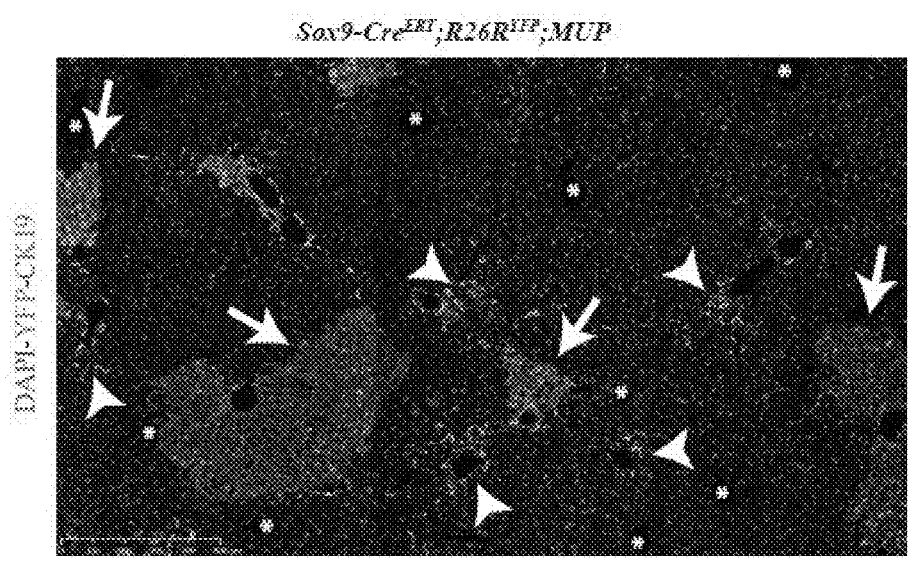
Figure 14B:
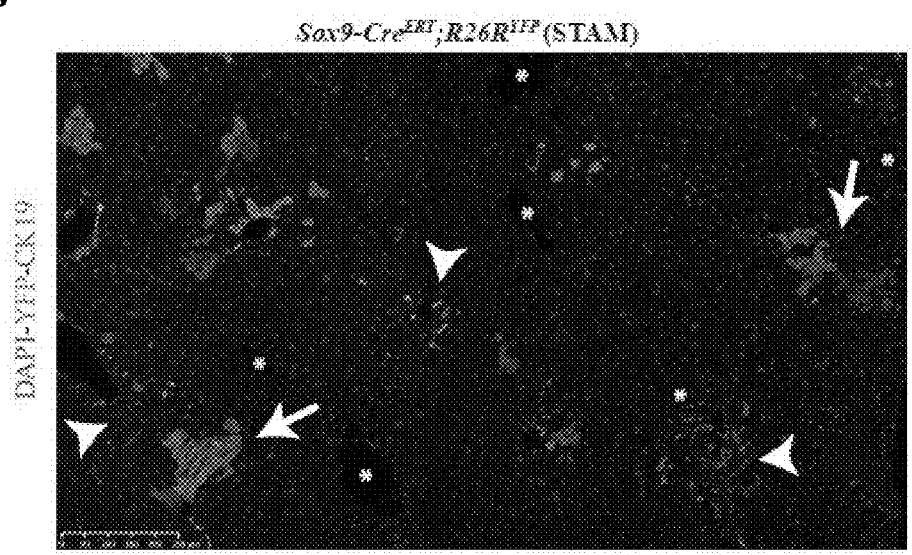
Figure 14C:
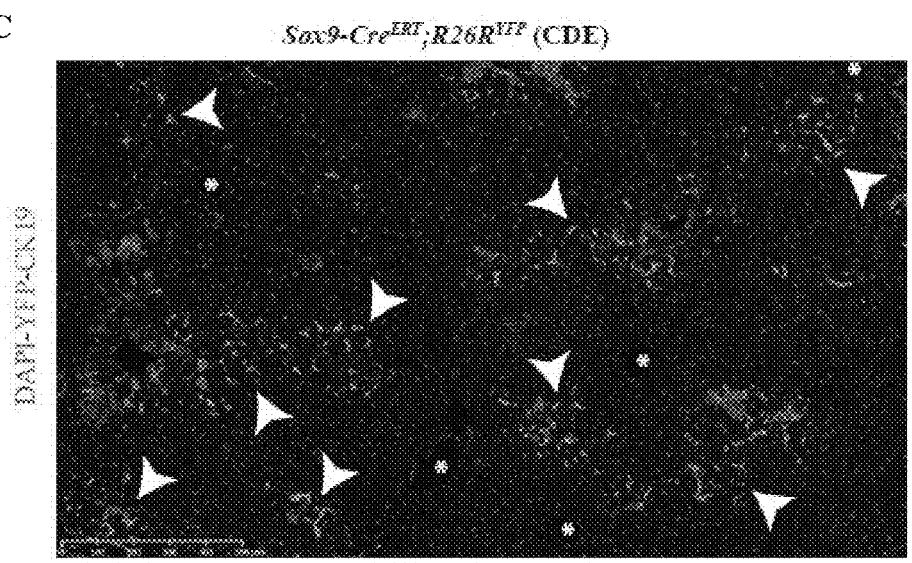

We next analyzed the relationship between HybHP and the oval cell response. Whole slide scans of Sox9-Cre$^{ERT}$; R26R$^{YFP}$; MUP-uPA livers revealed that in the portal tracts where HybHP are expanding, only a few oval cells were present (FIG. 14A). Similar results were obtained in STAM livers at 5 months of age (FIG. 14B). To further corroborate this negative correlation, we fed tamoxifen (100 mg/kg)-injected Sox9-Cre$^{ERT}$; R26R$^{YFP}$ mice with CDE diet, which leads to extensive damage of the liver parenchyma with high mortality (Akhurst et al., 2001). In these mice, most HybHP were destroyed and vast oval cell expansion was seen (FIG. 14C), suggesting a reciprocal relationship between oval cells and HybHP.

Example 7

Statistical Analysis

1. Data Pre-Processing and Model Goodness-of-Fit Assessment

In order to simulate expression data for the HybHP under various hypothesized relationships with cHP and BD, we considered five probability models (Poisson, Negative Binomial, Tweedie, Normal, Gamma) and assessed the degree to which they captured the nature of the observed RNA-seq data. For these analyses we used the 13,827 genes that had at least 100 read counts across all samples, in order to consider genes with relatively precise gene expression measurements.

The first three models focus on the gene-level read counts, assuming that these arise from Poisson, Negative Binomial or Tweedie distributions (respectively). Esnaola et al (2013) pointed that, although commonly used for the analysis of RNA-seq data, the Poisson and Negative Binomial are often an inadequate description of RNA-seq counts and that a generalization based on the Tweedie distribution is needed. As suggested by the authors we used function gofTest from R package TweeDEseq to produce quantile-quantile plots (FIG. 15A,B, respectively), where the departure of the observed quantiles from the straight line confirmed the poor fit of the Poisson and Negative Binomial (respectively).

Figure 15A:
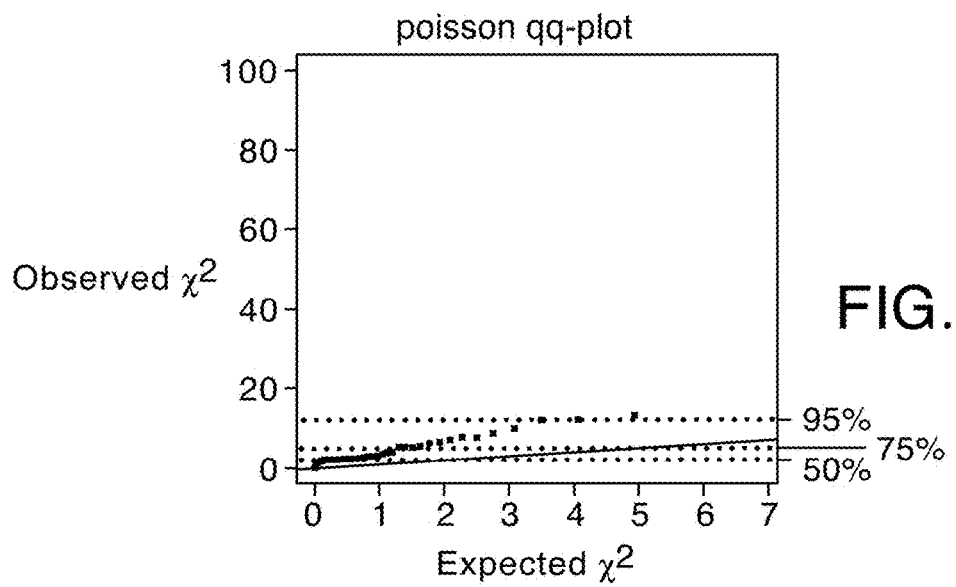
Figure 15B:
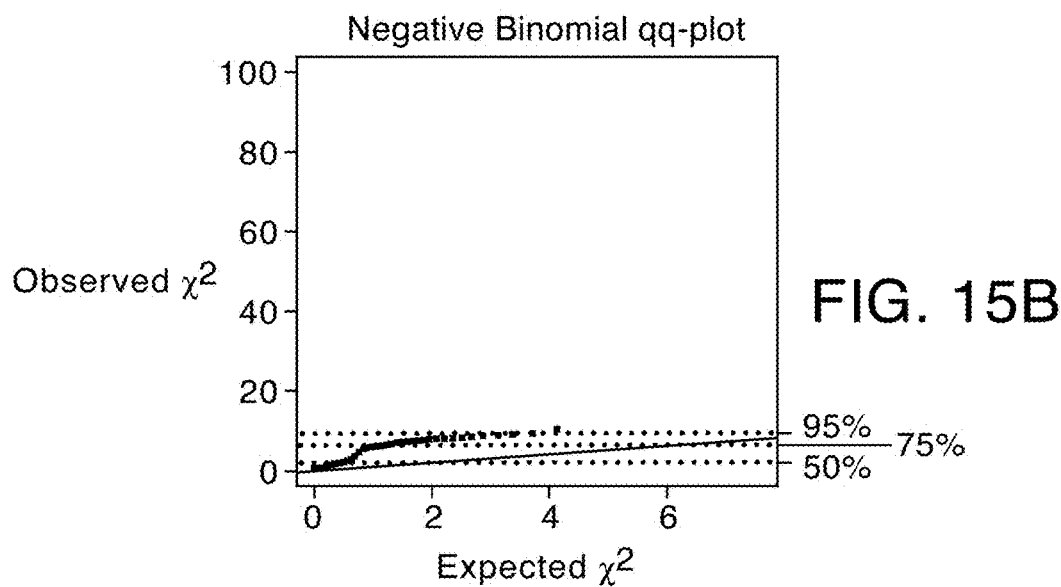
Figure 15C:
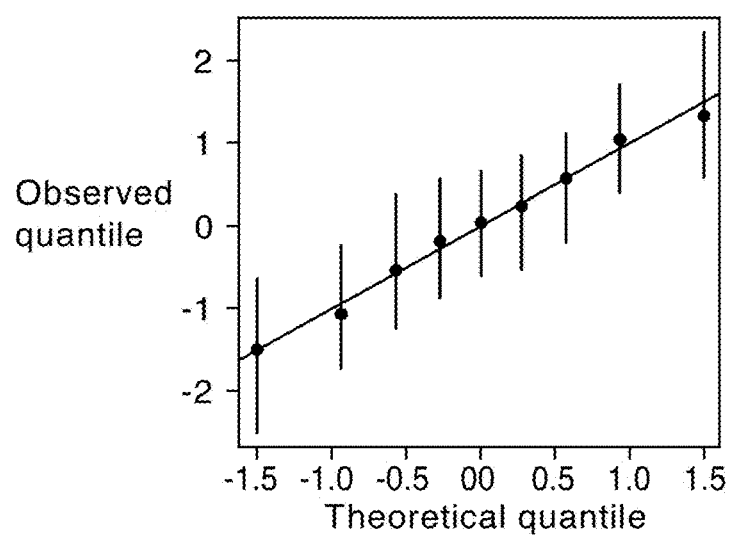
Figure 15D:
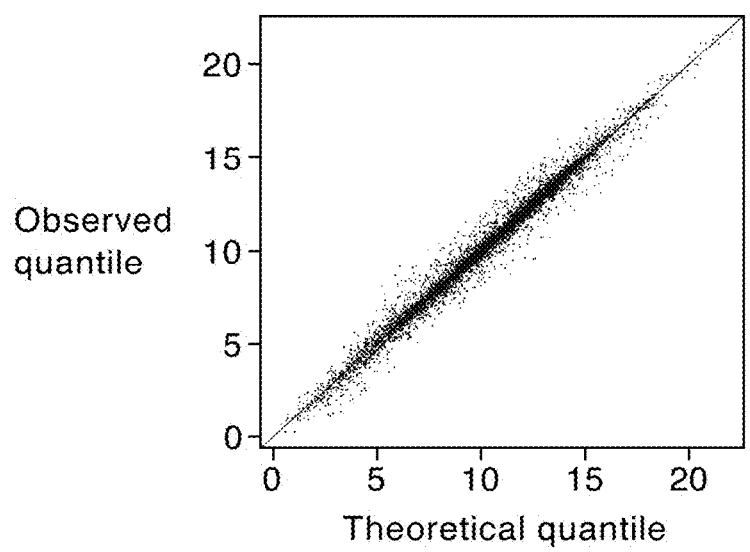
Figure 15E:
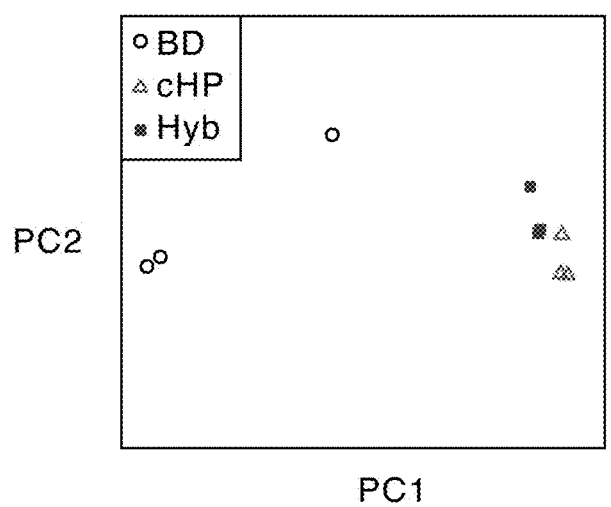
Figure 15F:
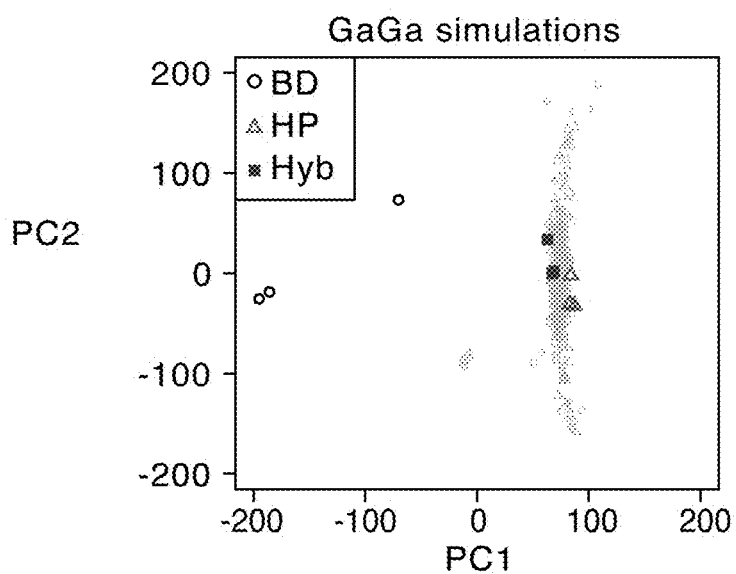
Figure 15G:
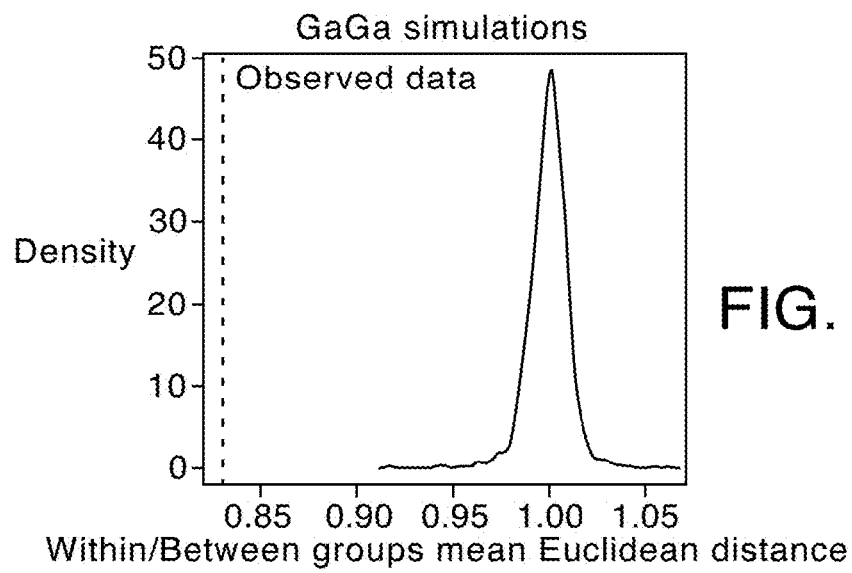

As an alternative, the Normal and Gamma models assume a continuous distribution for gene expression. As these would be inadequate for read counts, we computed log 2 reads per kilobase per million (RPKM) and applied quantile normalization to remove systematic biases across samples. We assessed goodness-of-fit of the Normal model using function qqnormGenomeWide from R package casper (Rossell et al., 2014), observing a departure from Normality (FIG. 15C), whereas the Gamma model provided a more accurate fit (FIG. 15D).

2. Testing the Hypothesis that HybHP Arises as Noise from cHP

We conducted an analysis to confirm that HybHP expression cannot be explained as simply a noisy version of cHP expression, i.e. we considered the null hypothesis that for all genes there are truly no differences between the HybHP and cHP groups.

HybHP samples clustered separately from cHP samples both in a Principal Components (FIG. 15E) and a hierarchical clustering analysis with Euclidean distance and complete linkage (FIG. 15A), suggesting the existence of systematic differences in expression between the two groups. To numerically assess these differences, we computed the ratio of the mean distance within the HybHP and cHP groups divided by the mean between-groups distances. We denote this ratio by rdist. In the absence of HybHP vs. cHP differences the ratio should be 1, but we observed rdist=0.83, suggesting the existence of systematic differences between HybHP and cHP. As a further numerical assessment, we used the GaGa model on the log 2-RPKM expressions (Rossell, 2009) to estimate the proportion of genes following each of the following expression patterns.

Pattern 0: BD=cHP=HybHP
Pattern 1: cHP=HybHP≠BD
Pattern 2: BD=HybHP≠HP
Pattern 3: BD=cHP≠HybHP
Pattern 4: BD≠HP≠HybHP GaGa estimated that 0.3% genes arose from Patterns 2-4, which correspond to configurations under which there truly are differences in expression between HybHP and cHP.

To conduct a formal statistical test we simulated 1,000 genome-wide datasets under the null hypothesis (no differences between HybHP and cHP for any gene) and assuming that the data are either Gamma (for log 2-RPKM) or Tweedie (for read counts) distributed. For the Gamma simulations we relabeled HybHP and cHP samples as belonging to a single group and generated new samples from the posterior predictive distribution of the GaGa model (Rossell, 2009), as implemented in function simnewsamples in the R package gaga. For the Tweedie simulations we adapted the rPT function in R package TweeDEseq. Given that the numerical optimizer in rPT to find parameter estimates may fail to converge for certain genes, whenever this happened we used the Negative Binomial distribution instead.

Figure 15H:
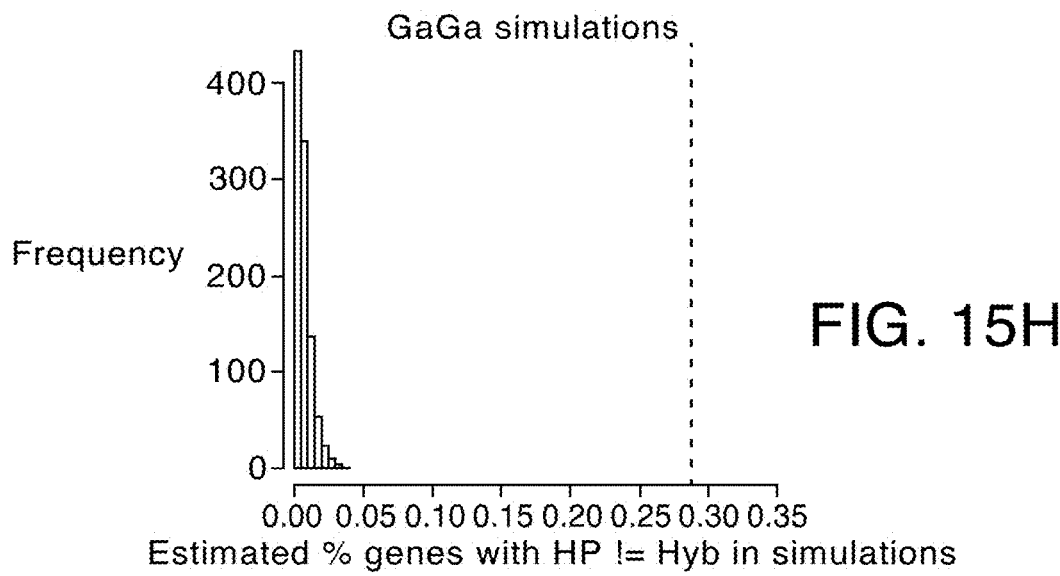
Figure 15I:
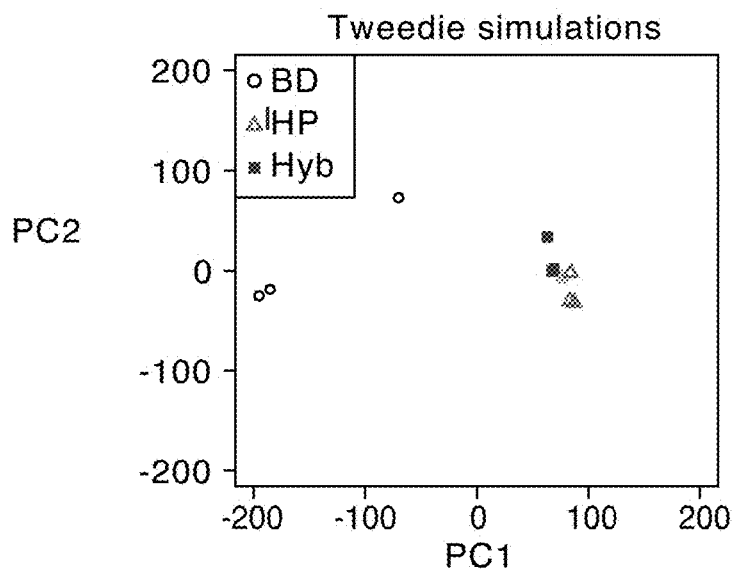
Figure 15J:
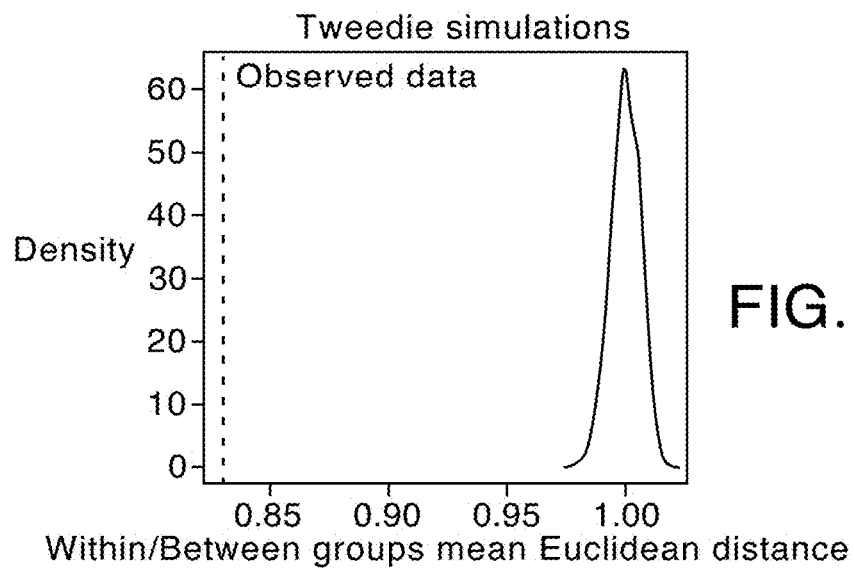
Figure 15K:
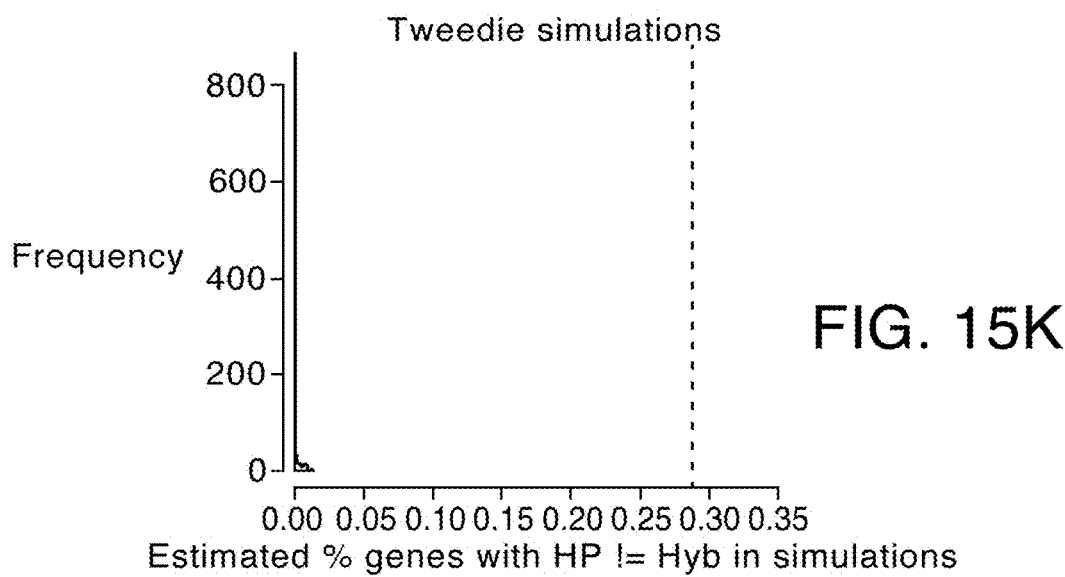

We produced a Principal Components plot showing the observed and simulated data (FIG. 15F,I) which revealed that the GaGa model captured the within-groups variability more adequately than the Tweedie model, which tended to under-estimate it. Both the GaGa and Tweedie simulations assign strong statistical significance (P-value<0.001) to the observed rdist=0.83 (FIG. 15G,J) and also to the estimated 0.3% genes arising from Patterns 2-4 (FIG. 15H,K). Overall, these results provided strong evidence against the hypothesis of no differences in expression between cHP and HybHP.

3. Testing the Hypothesis that HybHP is a Mixture of cHP and BD

We performed an analysis to rule out the hypothesis that the HybHP samples were generated by a mixture of cHP cells contaminated by a small fraction of BD cells. Under this hypothesis, the expression for any gene g should follow the pattern $HybHP_g = w\ BD_g + (1-w)\ cHP_g$, where w is the proportion of contaminating BD cells (common across all genes), or equivalently the linear model $HybHP_g/cHP_g = w\ BD_g/cHP_g + 1 - w$. The common parameter w was estimated using robust linear regression as implemented in function rlm from R package MASS (Hampel et al., 1986; Venables and Ripley, 2011).

To prevent outliers in the $HybHP_g/cHP_g$ or $BD_g/cHP_g$ fold changes from unduly biasing the estimate, we obtained an estimated w=0.8% with 95% bootstrap confidence intervals [0.1%, 2.8%].

To test the mixture hypothesis we pre-screened candidate genes unlikely to arise from such a mixture by selecting the 770 genes with $HybHP_g/cHP_g$ above 2 in both direction and read count >10 in the cHP group. We then simulated 10,000 datasets under the mixture hypothesis using the GaGa model (Algorithm 1).

Algorithm 1. Simulation of Gene Expression Data Under the Mixture Hypothesis

For b=1, . . . , 10000, do the following steps.
1. Simulate 3 new $cHP^{(b)}$ and $HybHP^{(b)}$ samples from the GaGa model posterior predictive under the pattern HybHP BD for the 770 genes. Center simulated data so that the grand average equals that in the observed data, i.e. $0.5(cHP_g^{(b)} + HybHP_g^{(b)}) = 0.5(cHP_g + HybHP_g)$.
2. Simulate a value of the proportion of BD cells $w^{(b)}$ from a bootstrap rlm fit.
3. Generate 3 new HybHP samples as $HybHP_g^{(b)} = w^{(b)} BD_g^{(b)} + (1-w^{(b)})\ cHP_g^{(b)}$.

Figure 15L:
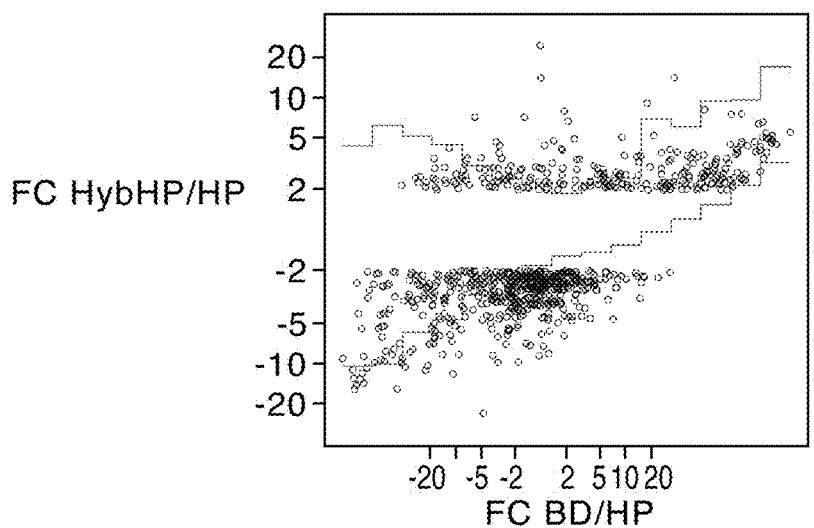

Algorithm 1 incorporates the uncertainty both in the parameter estimates at the gene level and that in w, and uses a Gamma distribution for the observations as it provided a better fit to the observed data that the other four probability models described in Example 7, under the heading "Testing the hypothesis that HybHP arises as noise from cHP." Under the mixture hypothesis, for each gene the proportion $p_g$ of simulated $HybHP_g^{(b)}/cHP_g^{(b)}$ below the observed $HybHP_g/cHP_g$ should follow a Uniform(0,1) distribution. Hence we computed a two-tailed P-value as $\min\{p_g, 1-p_g\}$, and applied Bonferroni's adjustment to determine statistically significant hits. To ensure that no hits were due to Monte Carlo error in the P-value estimate, we grouped the 770 genes into 15 subgroups according to their $BD_g/cHP_g$ values and computed the interval containing 95% of the simulated fold changes (FIG. 15L). Only genes having both Bonferroni adjusted P-value<0.05 and $HybHP_g/cHP_g$ beyond the 95% intervals were deemed significant.

The results of the statistical analysis are shown in FIG. 5, 15, and Tables 1-3 (supra).

Example 8

Culture of Isolated HybHP In Vitro

In practice, the therapeutic potential of HybHP will depend on the ability to maintain and expand them in culture. In recent years, there has been an explosion of three dimensional (3D) cell culture techniques, which have now been applied to a great variety of tissue and cell types. The liver has been no exception, and it was reported that ductal cells can form organoids that can be expanded for extended periods of time without compromising genome stability. Importantly, hepatocytes do not form organoids under the same conditions as ductal cells. Since HybHP retain a ductal character and even transdifferentiate into ductal cells in vivo in the setting of cholestatic injury, when cultured in the 3D culture conditions, HybHP could transdifferentiate and generate ductal organoids allowing their expansion. FIG. 16 shows that isolated ductal cells readily form organoids, while HybHP after a longer period start generating similar organoids. These results show that HybHP are unique hepatocytes with the potential to be expanded ex vivo to obtain enough number of cells to be used clinically.

REFERENCES CITED IN EXAMPLE 1:
EXPERIMENTAL PROCEDURES" AND
EXAMPLE 7: STATISTICAL ANALYSIS

Chung, K., and Deisseroth, K. (2013). CLARITY for mapping the nervous system. Nat Methods 10, 508-513.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Fujii, M., Shibazaki, Y., Wakamatsu, K., Honda, Y., Kawauchi, Y., Suzuki, K., Arumugam, S., Watanabe, K., Ichida, T., Asakura, H., et al. (2013). A murine model for non-alcoholic steatohepatitis showing evidence of association between diabetes and hepatocellular carcinoma. Medical molecular morphology 46, 141-152.

Gong, S., Zheng, C., Doughty, M. L., Losos, K., Didkovsky, N., Schambra, U. B., Nowak, N. J., Joyner, A., Leblanc, G., Hatten, M. E., et al. (2003). A gene expression atlas of the central nervous system based on bacterial artificial chromosomes. Nature 425, 917-925.

Grompe, M., al-Dhalimy, M., Finegold, M., Ou, C. N., Burlingame, T., Kennaway, N. G., and Soriano, P. (1993). Loss of fumarylacetoacetate hydrolase is responsible for the neonatal hepatic dysfunction phenotype of lethal albino mice. Genes & development 7, 2298-2307.

Hampel, F. R., Ronchetti, E. M., Rousseeuw, P. J., and Stahel, W. A. (1986). Robust statistics. The approach based on influence functions, i. edn (New York: John Wiley E Sons).

Heinz, S., Benner, C., Spann, N., Bertolino, E., Lin, Y. C., Laslo, P., Cheng, J. X., Murre, C., Singh, H., and Glass, C. K. (2010). Simple combinations of lineage-determining transcription factors prime cis-regulatory elements required for macrophage and B cell identities. Molecular cell 38, 576-589.

Huang da, W., Sherman, B. T., and Lempicki, R. A. (2009a). Bioinformatics enrichment tools: paths toward the comprehensive functional analysis of large gene lists. Nucleic acids research 37, 1-13.

Huang da, W., Sherman, B. T., and Lempicki, R. A. (2009b). Systematic and integrative analysis of large gene lists using DAVID bioinformatics resources. Nature protocols 4, 44-57.

Kopp, J. L., Dubois, C. L., Schaffer, A. E., Hao, E., Shih, H. P., Seymour, P. A., Ma, J., and Sander, M. (2011). Sox9+ ductal cells are multipotent progenitors throughout development but do not produce new endocrine cells in the normal or injured adult pancreas. Development 138, 653-665.

Maeda, S., Kamata, H., Luo, J. L., Leffert, H., and Karin, M. (2005). IKKbeta couples hepatocyte death to cytokine-driven compensatory proliferation that promotes chemical hepatocarcinogenesis. Cell 121, 977-990.

Means, A. L., Xu, Y., Zhao, A., Ray, K. C., and Gu, G. (2008). A CK19(CreERT) knockin mouse line allows for conditional DNA recombination in epithelial cells in multiple endodermal organs. Genesis 46, 318-323.

Nakagawa, H., Umemura, A., Taniguchi, K., Font-Burgada, J., Dhar, D., Ogata, H., Zhong, Z., Valasek, M. A., Seki, E., Hidalgo, J., et al. (2014). ER Stress Cooperates with Hypernutrition to Trigger TNF-Dependent Spontaneous HCC Development. Cancer cell 26, 331-343.

Ponder, K. P., Gupta, S., Leland, F., Darlington, G., Finegold, M., DeMayo, J., Ledley, F. D., Chowdhury, J. R., and Woo, S. L. (1991). Mouse hepatocytes migrate to liver parenchyma and function indefinitely after intrasplenic transplantation. Proceedings of the National Academy of Sciences of the United States of America 88, 1217-1221.

Robinson, M. D., McCarthy, D. J., and Smyth, G. K. (2010). edgeR: a Bioconductor package for differential expression analysis of digital gene expression data. Bioinformatics 26, 139-140.

Rossell, D. (2009). Gaga: A Parsimonious and Flexible Model for Differential Expression Analysis. Ann Appl Stat 3, 1035-1051.

Rossell, D., Attolini, C. S. O., Kroiss, M., and Stocker, A. (2014). Quantifying Alternative Splicing from Paired-End Rna-Sequencing Data. Ann Appl Stat 8, 309-330.

Schuler, M., Dierich, A., Chambon, P., and Metzger, D. (2004). Efficient temporally controlled targeted somatic mutagenesis in hepatocytes of the mouse. Genesis 39, 167-172.

Tannour-Louet, M., Porteu, A., Vaulont, S., Kahn, A., and Vasseur-Cognet, M. (2002). A tamoxifen-inducible chimeric Cre recombinase specifically effective in the fetal and adult mouse liver. Hepatology 35, 1072-1081.

Venables, W. N., and Ripley, B. D. (2011). Modern applied statistics with S, 4th edn (New York; Berlin; Heidelberg: Springer).

Weglarz, T. C., Degen, J. L., and Sandgren, E. P. (2000). Hepatocyte transplantation into diseased mouse liver. Kinetics of parenchymal repopulation and identification of the proliferative capacity of tetraploid and octaploid hepatocytes. The American journal of pathology 157, 1963-1974.

Yamamoto, M., Shook, N. A., Kanisicak, O., Yamamoto, S., Wosczyna, M. N., Camp, J. R., and Goldhamer, D. J. (2009). A multifunctional reporter mouse line for Cre- and FLP-dependent lineage analysis. Genesis 47, 107-114.

REFERENCES CITED IN THE SPECIFICATION,
OTHER THAN IN EXAMPLE 1:
EXPERIMENTAL PROCEDURES

Akhurst, B., Croager, E. J., Farley-Roche, C. A., Ong, J. K., Dumble, M. L., Knight, B., and Yeoh, G. C. (2001). A modified choline-deficient, ethionine-supplemented diet protocol effectively induces oval cells in mouse liver. Hepatology 34, 519-522.

Alison, M. R., Islam, S., and Lim, S. (2009). Stem cells in liver regeneration, fibrosis and cancer: the good, the bad and the ugly. The Journal of pathology 217, 282-298.

Benhamouche, S., Decaens, T., Godard, C., Chambrey, R., Rickman, D. S., Moinard, C., Vasseur-Cognet, M., Kuo, C. J., Kahn, A., Perret, C., et al. (2006). Apc tumor suppressor gene is the "zonation-keeper" of mouse liver. Developmental cell 10, 759-770.

Bissig, K.-D. D., Le, T. T., Woods, N.-B. B., and Verma, I. M. (2007). Repopulation of adult and neonatal mice with human hepatocytes: a chimeric animal model. Proceedings of the National Academy of Sciences of the United States of America 104, 20507-20511.

Blanpain, C., and Fuchs, E. (2014). Stem cell plasticity. Plasticity of epithelial stem cells in tissue regeneration. Science (New York, N.Y.) 344, 1242281.

Boulter, L., Lu, W.-Y. Y., and Forbes, S. J. (2013). Differentiation of progenitors in the liver: a matter of local choice. The Journal of clinical investigation 123, 1867-1873.

Carpentier, R., Suner, R. E., van Hul, N., Kopp, J. L., Beaudry, J. B., Cordi, S., Antoniou, A., Raynaud, P., Lepreux, S., Jacquemin, P., et al. (2011). Embryonic ductal plate cells give rise to cholangiocytes, periportal hepatocytes, and adult liver progenitor cells. Gastroenterology 141, 1432-1438, 1438 e1431-1434.

Cheung, T. H., and Rando, T. A. (2013). Molecular regulation of stem cell quiescence. Nature reviews Molecular cell biology 14, 329-340.

Chung, K., Wallace, J., Kim, S. Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

Clevers, H. (2013). The intestinal crypt, a prototype stem cell compartment. Cell 154, 274-284.

Dorrell, C., Erker, L., Schug, J., Kopp, J. L., Canaday, P. S., Fox, A. J., Smirnova, O., Duncan, A. W., Finegold, M. J., Sander, M., et al. (2011). Prospective isolation of a bipotential clonogenic liver progenitor cell in adult mice. Genes & development 25, 1193-1203.

Duncan, A. W., Dorrell, C., and Grompe, M. (2009). Stem cells and liver regeneration. Gastroenterology 137, 466-481.

Espanol-Suner, R., Carpentier, R., Van Hul, N., Legry, V., Achouri, Y., Cordi, S., Jacquemin, P., Lemaigre, F., and Leclercq, I. A. (2012). Liver progenitor cells yield functional hepatocytes in response to chronic liver injury in mice. Gastroenterology 143, 1564-1575 e1567.

Fausto, N., Campbell, J. S., and Riehle, K. J. (2006). Liver regeneration. Hepatology (Baltimore, Md.) 43, 53.

Fellous, T. G., Islam, S., Tadrous, P. J., Elia, G., Kocher, H. M., Bhattacharya, S., Mears, L., Turnbull, D. M., Taylor, R. W., Greaves, L. C., et al. (2009). Locating the stem cell niche and tracing hepatocyte lineages in human liver. Hepatology (Baltimore, Md.) 49, 1655-1663.

Fleming, K. E., and Wanless, I. R. (2013). Glutamine synthetase expression in activated hepatocyte progenitor cells and loss of hepatocellular expression in congestion and cirrhosis. Liver international: official journal of the International Association for the Study of the Liver 33, 525-534.

Fujii, M., Shibazaki, Y., Wakamatsu, K., Honda, Y., Kawauchi, Y., Suzuki, K., Arumugam, S., Watanabe, K., Ichida, T., Asakura, H., et al. (2013). A murine model for non-alcoholic steatohepatitis showing evidence of association between diabetes and hepatocellular carcinoma. Medical molecular morphology 46, 141-152.

Furuyama, K., Kawaguchi, Y., Akiyama, H., Horiguchi, M., Kodama, S., Kuhara, T., Hosokawa, S., Elbahrawy, A., Soeda, T., Koizumi, M., et al. (2010). Continuous cell supply from a Sox9-expressing progenitor zone in adult liver, exocrine pancreas and intestine. Nature genetics 43, 34-41.

Gong, S., Zheng, C., Doughty, M. L., Losos, K., Didkovsky, N., Schambra, U. B., Nowak, N. J., Joyner, A., Leblanc, G., Hatten, M. E., et al. (2003). A gene expression atlas of the central nervous system based on bacterial artificial chromosomes. Nature 425, 917-925.

Grompe, M. (2014). Liver stem cells, where art thou? Cell Stem Cell 15, 257-258.

Grompe, M., Lindstedt, S., al-Dhalimy, M., Kennaway, N. G., Papaconstantinou, J., Torres-Ramos, C. A., Ou, C. N., and Finegold, M. (1995). Pharmacological correction of neonatal lethal hepatic dysfunction in a murine model of hereditary tyrosinaemia type I. Nature genetics 10, 453-460.

He, G., Dhar, D., Nakagawa, H., Font-Burgada, J., Ogata, H., Jiang, Y., Shalapour, S., Seki, E., Yost, S. E., Jepsen, K., et al. (2013). Identification of liver cancer progenitors whose malignant progression depends on autocrine IL-6 signaling. Cell 155, 384-396.

Huch, M., Dorrell, C., Boj, S. F., van Es, J. H., Li, V. S., van de Wetering, M., Sato, T., Hamer, K., Sasaki, N., Finegold, M. J., et al. (2013). In vitro expansion of single Lgr5+ liver stem cells induced by Wnt-driven regeneration. Nature 494, 247-250.

Huch, M., Gehart, H., van Boxtel, R., Hamer, K., Blokzijl, F., Verstegen, M. M., Ellis, E., van Wenum, M., Fuchs, S. A., de Ligt, J., et al. (2015). Long-term culture of genome-stable bipotent stem cells from adult human liver. Cell 160, 299-312.

Hui, L., Bakiri, L., Mairhorfer, A., Schweifer, N., Haslinger, C., Kenner, L., Komnenovic, V., Scheuch, H., Beug, H., and Wagner, E. F. (2007). p38alpha suppresses normal and cancer cell proliferation by antagonizing the JNK-c-Jun pathway. Nature genetics 39, 741-749.

Inokuchi, S., Aoyama, T., Miura, K., Osterreicher, C. H., Kodama, Y., Miyai, K., Akira, S., Brenner, D. A., and Seki, E. (2010). Disruption of TAK1 in hepatocytes causes hepatic injury, inflammation, fibrosis, and carcinogenesis. Proceedings of the National Academy of Sciences of the United States of America 107, 844-849.

Isse, K., Lesniak, A., Grama, K., Maier, J., Specht, S., Castillo-Rama, M., Lunz, J., Roysam, B., Michalopoulos, G., and Demetris, A. J. (2013). Preexisting epithelial diversity in normal human livers: a tissue-tethered cytometric analysis in portal/periportal epithelial cells. Hepatology 57, 1632-1643.

Itoh, T., and Miyajima, A. (2014). Liver regeneration by stem/progenitor cells. Hepatology (Baltimore, Md.) 59, 1617-1626.

Jungermann, K., and Katz, N. (1989). Functional specialization of different hepatocyte populations. Physiological reviews 69, 708-764.

Kaneko, K., Kamimoto, K., Miyajima, A., and Itoh, T. (2015). Adaptive remodeling of the biliary architecture underlies liver homeostasis. Hepatology.

Kang, J. S., Wanibuchi, H., Morimura, K., Gonzalez, F. J., and Fukushima, S. (2007). Role of CYP2E1 in diethylnitrosamine-induced hepatocarcinogenesis in vivo. Cancer research 67, 11141-11146.

Karin, M. (2006). Nuclear factor-kappaB in cancer development and progression. Nature 441, 431-436.

Kisseleva, T., Gigante, E., and Brenner, D. A. (2010). Recent advances in liver stem cell therapy. Current opinion in gastroenterology 26, 395-402.

Kuraishy, A., Karin, M., and Grivennikov, S. I. (2011). Tumor promotion via injury- and death-induced inflammation. Immunity 35, 467-477.

Kuwahara, R., Kofman, A. V., Landis, C. S., Swenson, E. S., Barendswaard, E., and Theise, N. D. (2008). The hepatic stem cell niche: identification by label-retaining cell assay. Hepatology 47, 1994-2002.

Lavin, Y., Winter, D., Blecher-Gonen, R., David, E., Keren-Shaul, H., Merad, M., Jung, S., and Amit, I. (2014). Tissue-resident macrophage enhancer landscapes are shaped by the local microenvironment. Cell 159, 1312-1326.

Luedde, T., Beraza, N., Kotsikoris, V., van Loo, G., Nenci, A., De Vos, R., Roskams, T., Trautwein, C., and Pasparakis, M. (2007). Deletion of NEMO/IKKgamma in liver parenchymal cells causes steatohepatitis and hepatocellular carcinoma. Cancer cell 11, 119-132.

Maeda, S., Kamata, H., Luo, J. L., Leffert, H., and Karin, M. (2005). IKKbeta couples hepatocyte death to cytokine-driven compensatory proliferation that promotes chemical hepatocarcinogenesis. Cell 121, 977-990.

Malato, Y., Naqvi, S., Schurmann, N., Ng, R., Wang, B., Zape, J., Kay, M. A., Grimm, D., and Willenbring, H. (2011). Fate tracing of mature hepatocytes in mouse liver homeostasis and regeneration. J Clin Invest 121, 4850-4860.

Means, A. L., Xu, Y., Zhao, A., Ray, K. C., and Gu, G. (2008). A CK19CreERT knockin mouse line allows for conditional DNA recombination in epithelial cells in multiple endodermal organs. Genesis 46, 318-323.

Michalopoulos, G. K. (2007). Liver regeneration. Journal of cellular physiology 213, 286-300.

Michalopoulos, G. K., Barua, L., and Bowen, W. C. (2005). Transdifferentiation of rat hepatocytes into biliary cells after bile duct ligation and toxic biliary injury. Hepatology (Baltimore, Md.) 41, 535-544.

Miyajima, A., Tanaka, M., and Itoh, T. (2014). Stem/progenitor cells in liver development, homeostasis, regeneration, and reprogramming. Cell Stem Cell 14, 561-574.

Nakagawa, H., Hikiba, Y., Hirata, Y., Font-Burgada, J., Sakamoto, K., Hayakawa, Y., Taniguchi, K., Umemura, A., Kinoshita, H., Sakitani, K., et al. (2014a). Loss of liver E-cadherin induces sclerosing cholangitis and promotes carcinogenesis. Proc Natl Acad Sci USA 111, 1090-1095.

Nakagawa, H., Umemura, A., Taniguchi, K., Font-Burgada, J., Dhar, D., Ogata, H., Zhong, Z., Valasek, M. A., Seki, E., Hidalgo, J., et al. (2014b). ER Stress Cooperates with Hypernutrition to Trigger TNF-Dependent Spontaneous HCC Development. Cancer cell 26, 331-343.

Preisegger, K. H., Factor, V. M., Fuchsbichler, A., Stumptner, C., Denk, H., and Thorgeirsson, S. S. (1999). Atypical ductular proliferation and its inhibition by transforming growth factor beta1 in the 3,5-diethoxycarbonyl-1,4-dihydrocollidine mouse model for chronic alcoholic liver disease. Laboratory investigation; a journal of technical methods and pathology 79, 103-109.

Richardson, M. M., Jonsson, J. R., Powell, E. E., Brunt, E. M., Neuschwander-Tetri, B. A., Bhathal, P. S., Dixon, J. B., Weltman, M. D., Tilg, H., Moschen, A. R., et al. (2007). Progressive fibrosis in nonalcoholic steatohepatitis: association with altered regeneration and a ductular reaction. Gastroenterology 133, 80-90.

Rodrigo-Torres, D., Affo, S., Coll, M., Morales-Ibanez, O., Millan, C., Blaya, D., Alvarez-Guaita, A., Rentero, C., Lozano, J. J., Maestro, M. A., et al. (2014). The biliary epithelium gives rise to liver progenitor cells. Hepatology.

Roskams, T. (2006). Liver stem cells and their implication in hepatocellular and cholangiocarcinoma. Oncogene 25, 3818-3822.

Sakurai, T., He, G., Matsuzawa, A., Yu, G. Y., Maeda, S., Hardiman, G., and Karin, M. (2008). Hepatocyte necrosis induced by oxidative stress and IL-1 alpha release mediate carcinogen-induced compensatory proliferation and liver tumorigenesis. Cancer cell 14, 156-165.

Schaub, J. R., Malato, Y., Gormond, C., and Willenbring, H. (2014). Evidence against a Stem Cell Origin of New Hepatocytes in a Common Mouse Model of Chronic Liver Injury. Cell reports 8, 933-939.

Schmelzer, E., Zhang, L., Bruce, A., Wauthier, E., Ludlow, J., Yao, H. L., Moss, N., Melhem, A., McClelland, R., Turner, W., et al. (2007). Human hepatic stem cells from fetal and postnatal donors. The Journal of experimental medicine 204, 1973-1987.

Sekiya, S., and Suzuki, A. (2011). Direct conversion of mouse fibroblasts to hepatocyte-like cells by defined factors. Nature 475, 390-393.

Sekiya, S., and Suzuki, A. (2014). Hepatocytes, rather than cholangiocytes, can be the major source of primitive ductules in the chronically injured mouse liver. The American journal of pathology 184, 1468-1478.

Sell, S., and Leffert, H. L. (2008). Liver cancer stem cells. Journal of clinical oncology: official journal of the American Society of Clinical Oncology 26, 2800-2805.

Si-Tayeb, K., Noto, F. K., Nagaoka, M., Li, J., Battle, M. A., Duris, C., North, P. E., Dalton, S., and Duncan, S. A. (2009). Highly efficient generation of human hepatocyte-like cells from induced pluripotent stem cells. Hepatology (Baltimore, Md.) 51, 297-305.

Slack, J. M. (2007). Metaplasia and transdifferentiation: from pure biology to the clinic. Nature reviews Molecular cell biology 8, 369-378.

Tanimizu, N., Nishikawa, Y., Ichinohe, N., Akiyama, H., and Mitaka, T. (2014). Sry HMG Box Protein 9-positive (Sox9+) Epithelial Cell Adhesion Molecule-negative (EpCAM-) Biphenotypic Cells Derived from Hepatocytes Are Involved in Mouse Liver Regeneration. The Journal of biological chemistry 289, 7589-7598.

Tannour-Louet, M., Porteu, A., Vaulont, S., Kahn, A., and Vasseur-Cognet, M. (2002). A tamoxifen-inducible chimeric Cre recombinase specifically effective in the fetal and adult mouse liver. Hepatology (Baltimore, Md.) 35, 1072-1081.

Tarlow, B. D., Finegold, M. J., and Grompe, M. (2014a). Clonal tracing of Sox9+ liver progenitors in mouse oval cell injury. Hepatology 60, 278-289.

Tarlow, B. D., Pelz, C., Naugler, W. E., Wakefield, L., Wilson, E. M., Finegold, M. J., and Grompe, M. (2014b). Bipotential adult liver progenitors are derived from chronically injured mature hepatocytes. Cell Stem Cell 15, 605-618.

Tomasetti, C., and Vogelstein, B. (2015). Cancer etiology. Variation in cancer risk among tissues can be explained by the number of stem cell divisions. Science 347, 78-81.

Wang, X., Foster, M., Al-Dhalimy, M., Lagasse, E., Finegold, M., and Grompe, M. (2003). The origin and liver repopulating capacity of murine oval cells. Proceedings of the National Academy of Sciences of the United States of America 100 Suppl 1, 11881-11888.

Weglarz, T. C., Degen, J. L., and Sandgren, E. P. (2000). Hepatocyte transplantation into diseased mouse liver. Kinetics of parenchymal repopulation and identification of the proliferative capacity of tetraploid and octaploid hepatocytes. The American journal of pathology 157, 1963-1974.

Wong, F. W., Chan, W. Y., and Lee, S. S. (1998). Resistance to carbon tetrachloride-induced hepatotoxicity in mice which lack CYP2E1 expression. Toxicology and applied pharmacology 153, 109-118.

Yamamoto, M., Shook, N. A., Kanisicak, O., Yamamoto, S., Wosczyna, M. N., Camp, J. R., and Goldhamer, D. J. (2009). A multifunctional reporter mouse line for Cre- and FLP-dependent lineage analysis. Genesis (New York, N.Y.: 2000) 47, 107-114.

Yanger, K., Knigin, D., Zong, Y., Maggs, L., Gu, G., Akiyama, H., Pikarsky, E., and Stanger, B. Z. (2014). Adult hepatocytes are generated by self-duplication rather than stem cell differentiation. Cell Stem Cell 15, 340-349.

Yanger, K., Zong, Y., Maggs, L. R., Shapira, S. N., Maddipati, R., Aiello, N. M., Thung, S. N., Wells, R. G., Greenbaum, L. E., and Stanger, B. Z. (2013). Robust cellular reprogramming occurs spontaneously during liver regeneration. Genes & development 27, 719-724.

Yu, B., He, Z.-Y. Y., You, P., Han, Q.-W. W., Xiang, D., Chen, F., Wang, M.-J. J., Liu, C.-C. C., Lin, X.-W. W., Borjigin, U., et al. (2013). Reprogramming fibroblasts into bipotential hepatic stem cells by defined factors. Cell stem cell 13, 328-340.

Zhou, Q., and Melton, D. A. (2008). Extreme makeover: converting one cell into another. Cell stem cell 3, 382-388.

Zhu, S., Rezvani, M., Harbell, J., Mattis, A. N., Wolfe, A. R., Benet, L. Z., Willenbring, H., and Ding, S. (2014). Mouse liver repopulation with hepatocytes generated from human fibroblasts. Nature 508, 93-97.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A method for purifying a hybrid hepatocyte (HybHP) cell from a normal mammalian liver, said method comprising,
    a) preparing a single-cell suspension from said normal mammalian liver,
    b) combining said single-cell suspension with
        i) at least one first antibody that specifically binds to a plasma membrane first protein marker of liver ductal (DC) cells, and
        ii) at least one second antibody that specifically binds to a second protein marker of conventional hepatocyte (cHP) cells, wherein said second protein marker of cHP cells is underexpressed in said HybHP cells compared to cHP cells,
    wherein said combining is under conditions for specific binding of said at least one first antibody to said first protein marker, and of said at least one second antibody to said second protein marker, and wherein said specific binding produces a first composition that comprises a first antibody-HybHP cell-second antibody conjugate, and
    c) isolating said first antibody-HybHP cell-second antibody conjugate from said single-cell suspension, thereby producing a second composition that comprises a purified HybHP cell.

2. A method for purifying a hybrid hepatocyte (HybHP) cell from a normal mammalian liver, said method comprising,
    a) preparing a single-cell suspension from said normal mammalian liver,
    b) substantially removing ductal cells from said single-cell suspension to obtain a first population of cells that contains conventional hepatocyte (cHP) cells and HybHP cells,
    c) combining said first population of cells with at least one first antibody that specifically binds to a plasma membrane first protein marker of liver ductal (DC) cells, wherein said combining is under conditions for specific binding of said at least one first antibody to said first protein marker, and wherein said specific binding produces a first composition that comprises a first-antibody-HybHP cell conjugate, and
    d) isolating said first antibody-HybHP cell conjugate from said first population of cells, thereby producing a second population of cells that comprises a purified HybHP cell.

* * * * *